US009818260B2

(12) United States Patent
Arnone et al.

(10) Patent No.: US 9,818,260 B2
(45) Date of Patent: Nov. 14, 2017

(54) DELAYED WAGERING INTERLEAVED WAGERING SYSTEM

(71) Applicant: Gamblit Gaming, LLC, Glendale, CA (US)

(72) Inventors: Miles Arnone, Sherborn, MA (US); Eric Meyerhofer, Pasadena, CA (US); David Chang, San Gabriel, CA (US)

(73) Assignee: Gamblit Gaming, LLC, Glendale, CA (US)

( * ) Notice: Subject to any disclaimer, the term of this patent is extended or adjusted under 35 U.S.C. 154(b) by 0 days.

(21) Appl. No.: 15/599,590

(22) Filed: May 19, 2017

(65) Prior Publication Data

US 2017/0256130 A1 Sep. 7, 2017

Related U.S. Application Data

(63) Continuation of application No. 14/855,322, filed on Sep. 15, 2015, now Pat. No. 9,659,438.

(60) Provisional application No. 62/050,722, filed on Sep. 15, 2014.

(51) Int. Cl.
*A61F 13/00* (2006.01)
*G07F 17/32* (2006.01)

(52) U.S. Cl.
CPC ...... *G07F 17/3227* (2013.01); *G07F 17/3206* (2013.01); *G07F 17/3225* (2013.01); *G07F 17/3244* (2013.01)

(58) Field of Classification Search
CPC ............. G07F 17/3206; G07F 17/3225; G07F 17/3227; G07F 17/3244
USPC ........................................................... 463/25
See application file for complete search history.

(56) References Cited

U.S. PATENT DOCUMENTS

| | | | |
|---|---|---|---|
| 5,413,357 | A | 5/1995 | Schulze et al. |
| 5,718,429 | A | 2/1998 | Keller |
| 5,785,592 | A | 7/1998 | Jacobsen |
| 5,853,324 | A | 12/1998 | Kami et al. |
| 5,963,745 | A | 10/1999 | Collins et al. |
| 6,050,895 | A | 4/2000 | Luciano |
| 6,165,071 | A | 12/2000 | Weiss |

(Continued)

OTHER PUBLICATIONS

U.S. Appl. No. 14/815,764 Arnone, et al. filed Jul. 31, 2015.

(Continued)

*Primary Examiner* — Allen Chan
(74) *Attorney, Agent, or Firm* — Caitlyn Ross

(57) ABSTRACT

A delayed wager interleaved wagering system is disclosed including an interactive processing device constructed to: provide an interactive application display; request wager actuator data; automatically configure the display to provide a wager actuator; communicate wager actuator activation data; receive wagering telemetry data and application resource data; responsive to receiving the wagering telemetry data, automatically configure the display; a wager server constructed to: receive wager request data; automatically determine and communicate a wager outcome; and the process controller operatively connecting the interactive processing device and the wager server, and constructed to: provide the wager actuator data; communicate the wager actuator data; receive the wager actuator activation data; generate wager request data; communicate the wager request data; receive the wager outcome data; automatically determine and communicate the wagering telemetry data and the application resource data.

20 Claims, 23 Drawing Sheets

(56) References Cited

U.S. PATENT DOCUMENTS 6,227,974 B1 5/2001 Eilat
6,267,669 B1 7/2001 Luciano
6,685,563 B1 2/2004 Meekins et al.
6,712,693 B1 3/2004 Hettinger
6,761,632 B2 7/2004 Bansemer et al.
6,761,633 B2 7/2004 Riendeau
6,764,397 B1 7/2004 Robb
6,811,482 B2 11/2004 Letovsky
7,118,105 B2 10/2006 Benevento
7,294,058 B1 11/2007 Slomiany
7,326,115 B2 2/2008 Baerlocher
7,361,091 B2 4/2008 Letovsky
7,517,282 B1 4/2009 Pryor
7,575,517 B2 8/2009 Parham et al.
7,682,239 B2 3/2010 Friedman et al.
7,720,733 B2 5/2010 Jung
7,753,770 B2 7/2010 Walker et al.
7,753,790 B2 7/2010 Nguyen
7,766,742 B2 8/2010 Bennett et al.
7,775,885 B2 8/2010 Van Luchene
7,798,896 B2 9/2010 Katz
7,828,657 B2 11/2010 Booth
7,917,371 B2 3/2011 Jung et al.
7,931,531 B2 4/2011 Oberberger
7,938,727 B1 5/2011 Konkle
7,950,993 B2 5/2011 Oberberger
7,967,674 B2 6/2011 Baerlocher
7,980,948 B2 7/2011 Rowe
7,996,264 B2 8/2011 Kusumoto et al.
8,012,023 B2 9/2011 Gates
8,047,908 B2 11/2011 Walker
8,047,915 B2 11/2011 Lyle
8,060,829 B2 11/2011 Jung et al.
8,075,383 B2 12/2011 Friedman et al.
8,087,999 B2 1/2012 Oberberger
8,113,938 B2 2/2012 Friedman et al.
8,118,654 B1 2/2012 Nicolas
8,128,487 B2 3/2012 Hamilton et al.
8,135,648 B2 3/2012 Oram
8,137,193 B1 3/2012 Kelly et al.
8,142,272 B2 3/2012 Walker
8,157,653 B2 4/2012 Buhr
8,167,699 B2 5/2012 Inamura
8,177,628 B2 5/2012 Manning
8,182,338 B2 5/2012 Thomas
8,182,339 B2 5/2012 Anderson
8,187,068 B2 5/2012 Slomiany
8,206,210 B2 6/2012 Walker
8,308,544 B2 11/2012 Friedman
8,430,735 B2 4/2013 Oberberger
8,475,266 B2 7/2013 Arnone
8,480,470 B2 7/2013 Napolitano et al.
8,622,809 B1 1/2014 Arora et al.
8,864,564 B2 10/2014 Oberberger
9,070,257 B1 6/2015 Scalise
2001/0004609 A1 6/2001 Walker et al.
2001/0019965 A1 9/2001 Ochi
2002/0022509 A1 2/2002 Nicastro et al.
2002/0090990 A1 7/2002 Joshi et al.
2002/0175471 A1 11/2002 Faith
2003/0060286 A1 3/2003 Walker et al.
2003/0119576 A1 6/2003 McClintic et al.
2003/0139214 A1 7/2003 Wolf et al.
2003/0171149 A1 9/2003 Rothschild
2003/0204565 A1 10/2003 Guo et al.
2003/0211879 A1 11/2003 Englman
2004/0092313 A1 5/2004 Saito et al.
2004/0102238 A1 5/2004 Taylor
2004/0121839 A1 6/2004 Webb
2004/0225387 A1 11/2004 Smith
2005/0003878 A1 1/2005 Updike
2005/0096124 A1 5/2005 Stronach
2005/0116411 A1 6/2005 Herrmann et al.
2005/0192087 A1 9/2005 Friedman et al.
2005/0233791 A1 10/2005 Kane
2005/0233806 A1 10/2005 Kane et al.
2005/0239538 A1 10/2005 Dixon
2005/0269778 A1 12/2005 Samberg
2005/0288101 A1 12/2005 Lockton et al.
2006/0003823 A1 1/2006 Zhang
2006/0003830 A1 1/2006 Walker et al.
2006/0035696 A1 2/2006 Walker
2006/0040735 A1 2/2006 Baerlocher
2006/0068913 A1 3/2006 Walker et al.
2006/0084499 A1 4/2006 Moshal
2006/0084505 A1 4/2006 Yoseloff
2006/0135250 A1 6/2006 Rossides
2006/0154710 A1 7/2006 Serafat
2006/0166729 A1 7/2006 Saffari et al.
2006/0189371 A1 8/2006 Walker et al.
2006/0223611 A1 10/2006 Baerlocher
2006/0234791 A1 10/2006 Nguyen et al.
2006/0240890 A1 10/2006 Walker
2006/0246403 A1 11/2006 Monpouet et al.
2006/0258433 A1 11/2006 Finocchio et al.
2007/0026924 A1 2/2007 Taylor
2007/0035548 A1 2/2007 Jung et al.
2007/0038559 A1 2/2007 Jung et al.
2007/0064074 A1 3/2007 Silverbrook et al.
2007/0087799 A1 4/2007 Van Luchene
2007/0093299 A1 4/2007 Bergeron
2007/0099696 A1 5/2007 Nguyen et al.
2007/0117641 A1 5/2007 Walker et al.
2007/0129149 A1 6/2007 Walker
2007/0142108 A1 6/2007 Linard
2007/0156509 A1 7/2007 Jung et al.
2007/0167212 A1 7/2007 Nguyen
2007/0167239 A1 7/2007 O'Rourke
2007/0173311 A1 7/2007 Morrow et al.
2007/0191104 A1 8/2007 Van Luchene
2007/0202941 A1 8/2007 Miltenberger
2007/0203828 A1 8/2007 Jung et al.
2007/0207847 A1 9/2007 Thomas
2007/0259717 A1 11/2007 Mattice
2007/0293306 A1 12/2007 Nee et al.
2008/0004107 A1 1/2008 Nguyen et al.
2008/0014835 A1 1/2008 Weston et al.
2008/0015004 A1 1/2008 Gatto et al.
2008/0064488 A1 3/2008 Oh
2008/0070659 A1 3/2008 Naicker
2008/0070690 A1 3/2008 Van Luchene
2008/0070702 A1 3/2008 Kaminkow
2008/0096665 A1 4/2008 Cohen
2008/0108406 A1 5/2008 Oberberger
2008/0108425 A1 5/2008 Oberberger
2008/0113704 A1 5/2008 Jackson
2008/0119283 A1 5/2008 Baerlocher
2008/0146308 A1 6/2008 Okada
2008/0161081 A1 7/2008 Berman
2008/0176619 A1 7/2008 Kelly
2008/0191418 A1 8/2008 Lutnick et al.
2008/0195481 A1 8/2008 Lutnick
2008/0248850 A1 10/2008 Schugar
2008/0254893 A1 10/2008 Patel
2008/0274796 A1 11/2008 Lube
2008/0274798 A1 11/2008 Walker et al.
2008/0311980 A1 12/2008 Cannon
2008/0318668 A1 12/2008 Ching
2009/0011827 A1 1/2009 Englman
2009/0023489 A1 1/2009 Toneguzzo
2009/0023492 A1 1/2009 Erfanian
2009/0061974 A1 3/2009 Lutnick et al.
2009/0061975 A1 3/2009 Ditchev
2009/0061991 A1 3/2009 Popovich
2009/0061997 A1 3/2009 Popovich
2009/0061998 A1 3/2009 Popovich
2009/0061999 A1 3/2009 Popovich
2009/0082093 A1 3/2009 Okada
2009/0088239 A1 4/2009 Iddings
2009/0098934 A1 4/2009 Amour
2009/0118006 A1 5/2009 Kelly et al.
2009/0124344 A1 5/2009 Mitchell et al.
2009/0131158 A1 5/2009 Brunet De Courssou et al.
2009/0131175 A1 5/2009 Kelly et al.

(56) References Cited

U.S. PATENT DOCUMENTS

2009/0143141 A1 6/2009 Wells
2009/0149233 A1 6/2009 Strause et al.
2009/0156297 A1 6/2009 Andersson et al.
2009/0176560 A1 7/2009 Herrmann et al.
2009/0176566 A1 7/2009 Kelly
2009/0181777 A1 7/2009 Christiani
2009/0221355 A1 9/2009 Dunaevsky et al.
2009/0239610 A1 9/2009 Olive
2009/0247272 A1 10/2009 Abe
2009/0270164 A1 10/2009 Seelig
2009/0275393 A1 11/2009 Kisenwether
2009/0291755 A1 11/2009 Walker et al.
2009/0309305 A1 12/2009 May
2009/0312093 A1 12/2009 Walker et al.
2009/0325686 A1 12/2009 Davis
2010/0004058 A1 1/2010 Acres
2010/0016056 A1 1/2010 Thomas et al.
2010/0029373 A1 2/2010 Graham et al.
2010/0035674 A1 2/2010 Slomiany
2010/0056247 A1 3/2010 Nicely
2010/0056260 A1 3/2010 Fujimoto
2010/0062836 A1 3/2010 Young
2010/0093420 A1 4/2010 Wright
2010/0093444 A1 4/2010 Biggar et al.
2010/0105454 A1 4/2010 Weber
2010/0120525 A1 5/2010 Baerlocher et al.
2010/0124983 A1 5/2010 Gowin et al.
2010/0137047 A1 6/2010 Englman et al.
2010/0174593 A1 7/2010 Cao
2010/0184509 A1 7/2010 Sylla et al.
2010/0203940 A1 8/2010 Alderucci et al.
2010/0210344 A1 8/2010 Edidin et al.
2010/0227672 A1 9/2010 Amour
2010/0227688 A1 9/2010 Lee
2010/0240436 A1 9/2010 Wilson et al.
2010/0285869 A1 11/2010 Walker
2010/0304825 A1 12/2010 Davis
2010/0304839 A1 12/2010 Johnson
2010/0304842 A1 12/2010 Friedman et al.
2011/0009177 A1 1/2011 Katz
2011/0009178 A1 1/2011 Gerson
2011/0045896 A1 2/2011 Sak et al.
2011/0070945 A1 3/2011 Walker
2011/0077087 A1 3/2011 Walker et al.
2011/0082571 A1 4/2011 Murdock et al.
2011/0105206 A1 5/2011 Rowe et al.
2011/0107239 A1 5/2011 Adoni
2011/0109454 A1 5/2011 McSheffrey
2011/0111820 A1 5/2011 Filipour
2011/0111837 A1 5/2011 Gagner
2011/0111841 A1 5/2011 Tessmer
2011/0118011 A1 5/2011 Filipour et al.
2011/0201413 A1 8/2011 Oberberger
2011/0207523 A1 8/2011 Filipour et al.
2011/0212766 A1 9/2011 Bowers
2011/0212767 A1 9/2011 Barclay
2011/0218028 A1 9/2011 Acres
2011/0218035 A1 9/2011 Thomas
2011/0230258 A1 9/2011 Van Luchene
2011/0230260 A1 9/2011 Morrow et al.
2011/0230267 A1 9/2011 Van Luchene
2011/0244944 A1 10/2011 Baerlocher
2011/0263312 A1 10/2011 De Waal
2011/0269522 A1 11/2011 Nicely et al.
2011/0275440 A1 11/2011 Faktor
2011/0287828 A1 11/2011 Anderson et al.
2011/0287841 A1 11/2011 Watanabe
2011/0312408 A1 12/2011 Okuaki
2011/0319169 A1 12/2011 Lam
2012/0004747 A1 1/2012 Kelly
2012/0028718 A1 2/2012 Barclay et al.
2012/0058814 A1 3/2012 Lutnick
2012/0077569 A1 3/2012 Watkins
2012/0108323 A1 5/2012 Kelly
2012/0135793 A1 5/2012 Antonopoulos
2012/0202587 A1 8/2012 Allen
2012/0302311 A1 11/2012 Luciano
2012/0322545 A1 12/2012 Arnone et al.
2013/0029760 A1 1/2013 Wickett
2013/0131848 A1 5/2013 Arnone et al.
2013/0190074 A1 7/2013 Arnone et al.
2013/0260869 A1 10/2013 Basallo et al.
2014/0087801 A1 3/2014 Nicely et al.
2014/0087808 A1 3/2014 Basallo et al.
2014/0087809 A1 3/2014 Leupp et al.
2014/0357350 A1 12/2014 Weingardt et al.

OTHER PUBLICATIONS

U.S. Appl. No. 14/815,774 Arnone, et al. filed Jul. 31, 2015.
U.S. Appl. No. 14/817,032 Arnone, et al. filed Aug. 3, 2015.
U.S. Appl. No. 14/822,890 Arnone, et al. filed Aug. 10, 2015.
U.S. Appl. No. 14/823,951 Arnone, et al. filed Aug. 11, 2015.
U.S. Appl. No. 14/823,987 Arnone, et al. filed Aug. 11, 2015.
U.S. Appl. No. 14/825,056 Arnone, et al. filed Aug. 12, 2015.
U.S. Appl. No. 14/835,590 Arnone, et al. filed Aug. 25, 2015.
U.S. Appl. No. 14,836,902 Arnone, et al. filed Aug. 26, 2015.
U.S. Appl. No. 14/839,647 Arnone, et al. filed Aug. 28, 2015.
U.S. Appl. No. 14/842,684 Arnone, et al. filed Sep. 1, 2015.
U.S. Appl. No. 14/842,785 Arnone, et al. filed Sep. 1, 2015.
U.S. Appl. No. 14/854,021 Arnone, et al. filed Sep. 14, 2015.
U.S. Appl. No. 14/855,322 Arnone, et al. filed Sep. 15, 2015.
U.S. Appl. No. 14/859,065 Arnone, et al. filed Sep. 18, 2015.
U.S. Appl. No. 14/865,422 Arnone, et al. filed Sep. 25, 2015.
U.S. Appl. No. 14/867,809 Arnone, et al. filed Sep. 28, 2015.
U.S. Appl. No. 14/868,287 Arnone, et al. filed Sep. 28, 2015.
U.S. Appl. No. 14/868,364 Arnone, et al. filed Sep. 28, 2015.
U.S. Appl. No. 14/869,809 Arnone, et al. filed Sep. 29, 2015.
U.S. Appl. No. 14/869,819 Arnone, et al. filed Sep. 29, 2015.
U.S. Appl. No. 14/885,894 Arnone, et al. filed Oct. 16, 2015.
U.S. Appl. No. 14/919,665 Arnone, et al. filed Oct. 21, 2015.
U.S. Appl. No. 14/942,844 Arnone, et al. filed Nov. 16, 2015.
U.S. Appl. No. 14/942,883 Arnone, et al. filed Nov. 16, 2015.
U.S. Appl. No. 14/949,759 Arnone, et al. filed Nov. 23, 2015.
U.S. Appl. No. 14/952,758 Arnone, et al. filed Nov. 25, 2015.
U.S. Appl. No. 14/952,769 Arnone, et al. filed Nov. 25, 2015.
U.S. Appl. No. 14/954,922 Arnone, et al. filed Nov. 30, 2015.
U.S. Appl. No. 14/954,931 Arnone, et al. filed Nov. 30, 2015.
U.S. Appl. No. 14/955,000 Arnone, et al. filed Nov. 30, 2015.
U.S. Appl. No. 14/956,301 Arnone, et al. filed Dec. 1, 2015.
U.S. Appl. No. 14/965,231 Arnone, et al. filed Dec. 10, 2015.
U.S. Appl. No. 14/965,846 Arnone, et al. filed Dec. 10, 2015.
U.S. Appl. No. 14/981,640 Arnone, et al. filed Dec. 28, 2015.
U.S. Appl. No. 14/981,775 Arnone, et al. filed Dec. 28, 2015.
U.S. Appl. No. 14/984,943 Arnone, et al. filed Dec. 30, 2015.
U.S. Appl. No. 14/984,965 Arnone, et al. filed Dec. 30, 2015.
U.S. Appl. No. 14/984,978 Arnone, et al. filed Dec. 30, 2015.
U.S. Appl. No. 14/985,107 Arnone, et al. filed Dec. 30, 2015.
U.S. Appl. No. 14/995,151 Arnone, et al. filed Jan. 13, 2016.
U.S. Appl. No. 14/974,432 Arnone, et al. filed Dec. 18, 2015.
U.S. Appl. No. 14/997,413 Arnone, et al. filed Jan. 15, 2016.
U.S. Appl. No. 15/002,233 Arnone, et al. filed Jan. 20, 2016.
U.S. Appl. No. 15/005,944 Arnone, et al. filed Jan. 25, 2016.
U.S. Appl. No. 15/011,322 Arnone, et al. filed Jan. 29, 2016.
U.S. Appl. No. 15/051,535 Arnone, et al. filed Feb. 23, 2016.
U.S. Appl. No. 15/053,236 Arnone, et al. filed Feb. 25, 2016.
U.S. Appl. No. 15/057,095 Arnone, et al. filed Feb. 29, 2016.
U.S. Appl. No. 15/060,502 Arnone, et al. filed Mar. 3, 2016.
U.S. Appl. No. 15/063,365 Arnone, et al. filed Mar. 7, 2016.
U.S. Appl. No. 15/063,496 Arnone, et al. filed Mar. 7, 2016.
U.S. Appl. No. 15/073,602 Arnone, et al. filed Mar. 17, 2016.
U.S. Appl. No. 15/074,999 Arnone, et al. filed Mar. 18, 2016.
U.S. Appl. No. 15/077,574 Arnone, et al. filed Mar. 22, 2016.
U.S. Appl. No. 15/083,284 Arnone, et al. filed Mar. 28, 2016.
U.S. Appl. No. 15/091,395 Arnone, et al. filed Apr. 5, 2016.
U.S. Appl. No. 15/093,685 Arnone, et al. filed Apr. 7, 2016.
U.S. Appl. No. 15/098,287 Arnone, et al. filed Apr. 13, 2016.
U.S. Appl. No. 15/098,313 Arnone, et al. filed Apr. 13, 2016.

(56) References Cited

OTHER PUBLICATIONS

U.S. Appl. No. 15/130,101 Arnone, et al. filed Apr. 15, 2016.
U.S. Appl. No. 15/133,624 Arnone, et al. filed Apr. 20, 2016.
U.S. Appl. No. 15/134,852 Arnone, et al. filed Apr. 21, 2016.
U.S. Appl. No. 15/139,148 Arnone, et al. filed Apr. 26, 2016.
U.S. Appl. No. 15/141,784 Arnone, et al. filed Apr. 29, 2016.
U.S. Appl. No. 15/155,107 Arnone, et al. filed May 16, 2016.
U.S. Appl. No. 15/156,222 Arnone, et al. filed May 16, 2016.
U.S. Appl. No. 15/158,530 Arnone, et al. filed May 18, 2016.
U.S. Appl. No. 15/161,174 Arnone, et al. filed May 20, 2016.
U.S. Appl. No. 15/170,773 Arnone, et al. filed Jun. 1, 2016.
U.S. Appl. No. 15/174,995 Arnone, et al. filed Jun. 6, 2016.
U.S. Appl. No. 15/179,940 Arnone, et al. filed Jun. 10, 2016.
U.S. Appl. No. 15/189,797 Arnone, et al. filed Jun. 22, 2016.
U.S. Appl. No. 15/190,745 Arnone, et al. filed Jun. 23, 2016.
U.S. Appl. No. 15/191,050 Arnone, et al. filed Jun. 23, 2016.
U.S. Appl. No. 15/219,257 Arnone, et al. filed Jul. 25, 2016.
U.S. Appl. No. 15/227,881 Arnone, et al. filed Aug. 3, 2016.
U.S. Appl. No. 15/241,683 Arnone, et al. filed Aug. 19, 2016.
U.S. Appl. No. 15/245,040 Arnone, et al. filed Aug. 23, 2016.
U.S. Appl. No. 15/233,294 Arnone, et al. filed Aug. 24, 2016.
U.S. Appl. No. 15/252,190 Arnone, et al. filed Aug. 30, 2016.
U.S. Appl. No. 15/255,789 Arnone, et al. filed Sep. 2, 2016.
U.S. Appl. No. 15/261,858 Arnone, et al. filed Sep. 9, 2016.
U.S. Appl. No. 15/264,521 Arnone, et al. filed Sep. 13, 2016.
U.S. Appl. No. 15/264,557 Arnone, et al. filed Sep. 13, 2016.
U.S. Appl. No. 15/271,214 Arnone, et al. filed Sep. 20, 2016.
U.S. Appl. No. 15/272,318 Arnone, et al. filed Sep. 21, 2016.
U.S. Appl. No. 15/273,260 Arnone, et al. filed Sep. 22, 2016.
U.S. Appl. No. 15/276,469 Arnone, et al. filed Sep. 26, 2016.
U.S. Appl. No. 15/280,255 Arnone, et al. filed Sep. 29, 2016.
U.S. Appl. No. 15/286,922 Arnone, et al. filed Oct. 6, 2016.
U.S. Appl. No. 151287,129 Arnone, et al. filed Oct. 6, 2016.
U.S. Appl. No. 15/289,648 Arnone, et al. filed Oct. 10, 2016.
U.S. Appl. No. 15/297,019 Arnone, et al. filed Oct. 18, 2016.
U.S. Appl. No. 15/298,533 Arnone, et al. filed Oct. 20, 2016.
U.S. Appl. No. 15/336,696 Arnone, et al. filed Oct. 27, 2016.
U.S. Appl. No. 15/339,898 Arnone, et al. filed Oct. 31, 2016.
U.S. Appl. No. 15/345,451 Arnone, et al. filed Nov. 7, 2016.
U.S. Appl. No. 14/799,481 Arnone, et al. filed Jul. 14, 2015.
U.S. Appl. No. 15/362,214 Arnone, et al. filed Nov. 28, 2016.
U.S. Appl. No. 14/185,847 Arnone, et al., filed Feb. 20, 2014.
U.S. Appl. No. 14/203,459 Arnone, et al., filed Mar. 10, 2014.
U.S. Appl. No. 14/205,272 Arnone, et al., filed Mar. 11, 2014.
U.S. Appl. No. 13/854,658, Arnone, et al., filed Apr. 1, 2013.
U.S. Appl. No. 13/855,676, Arnone, et al., filed Apr. 2, 2013.
U.S. Appl. No. 13/872,946, Arnone, et al., filed Apr. 29, 2013.
U.S. Appl. No. 13/886,245, Arnone, et al., filed May 2, 2013.
U.S. Appl. No. 13/888,326, Arnone, et al., filed May 6, 2013.
U.S. Appl. No. 13/890,207, Arnone, et al., filed May 8, 2013.
U.S. Appl. No. 13/896,783, Arnone, et al., filed May 17, 2013.
U.S. Appl. No. 13/898,222, Arnone, et al., filed May 20, 2013.
U.S. Appl. No. 13/900,363, Arnone, et al., filed May 22, 2013.
U.S. Appl. No. 13/903,895, Arnone, et al., filed May 28, 2013.
U.S. Appl. No. 13/917,513, Arnone, et al., filed Jun. 13, 2013.
U.S. Appl. No. 13/917,529, Arnone, et al., filed Jun. 13, 2013.
U.S. Appl. No. 13/920,031, Arnone, et al., filed Jun. 17, 2013.
U.S. Appl. No. 13/928,166, Arnone, et al., filed Jun. 26, 2013.
U.S. Appl. No. 13/935,410, Arnone, et al., filed Jul. 3, 2013.
U.S. Appl. No. 13/935,468, Arnone, et al., filed Jul. 3, 2013.
U.S. Appl. No. 13/686,876, Arnone, et al., filed Nov. 27, 2012.
U.S. Appl. No. 13/944,662, Arnone, et al., filed Jul. 17, 2013.
U.S. Appl. No. 13/962,815, Arnone, et al., filed Aug. 8, 2013.
U.S. Appl. No. 13/962,839, Meyerhofer, et al., filed Aug. 8, 2013.
U.S. Appl. No. 14/018,315, Arnone, et al., filed Sep. 4, 2013.
U.S. Appl. No. 14/019,384, Arnone, et al., filed Sep. 5, 2013.
U.S. Appl. No. 14/023,432, Arnone, et al., filed Sep. 10, 2013.
U.S. Appl. No. 13/600,671, Arnone, et al., filed Aug. 31, 2012.
U.S. Appl. No. 13/582,408, Arnone, et al., filed Sep. 26, 2012.
U.S. Appl. No. 13/849,458, Arnone, et al., filed Mar. 22, 2013.
U.S. Appl. No. 14/135,562, Arnone, et al., filed Dec. 19, 2013.
U.S. Appl. No. 14/080,767, Arnone, et al., filed Nov. 14, 2013.
U.S. Appl. No. 14/043,838, Arnone, et al., filed Oct. 1, 2013.
U.S. Appl. No. 14/162,735, Arnone, et al., filed Jan. 23, 2014.
U.S. Appl. No. 14/161,230, Arnone, et al., filed Jan. 22, 2014.
U.S. Appl. No. 14/083,331, Arnone, et al., filed Nov. 18, 2013.
U.S. Appl. No. 14/014,310, Arnone, et al., filed Aug. 29, 2013.
U.S. Appl. No. 14/152,953, Arnone, et al., filed Jan. 10, 2014.
U.S. Appl. No. 14/162,724, Arnone, et al., filed Jan. 23, 2014.
U.S. Appl. No. 14/104,897, Arnone, et al., filed Dec. 12, 2013.
U.S. Appl. No. 14/174,813 Arnone, et al., filed Feb. 6, 2014.
U.S. Appl. No. 14/175,986 Arnone, et al., filed Feb. 7, 2014.
U.S. Appl. No. 14/176,014 Arnone, et al., filed Feb. 7, 2014.
U.S. Appl. No. 14/179,487 Arnone, et al., filed Feb. 12, 2014.
U.S. Appl. No. 14/179,492 Arnone, et al., filed Feb. 12, 2014.
U.S. Appl. No. 14/181,190 Arnone, et al., filed Feb. 14, 2014.
U.S. Appl. No. 14/186,393 Arnone, et al., filed Feb. 21, 2014.
U.S. Appl. No. 14/188,587 Arnone, et al., filed Feb. 24, 2014.
U.S. Appl. No. 14/586,645 Arnone, et al. filed Dec. 30, 2014.
U.S. Appl. No. 14/598,151 Arnone, et al. filed Jan. 15, 2015.
U.S. Appl. No. 14/601,063 Arnone, et al. filed Jan. 20, 2015.
U.S. Appl. No. 14/601,108 Arnone, et al. filed Jan. 20, 2015.
U.S. Appl. No. 14/608,000 Arnone, et al. filed Jan. 28, 2015.
U.S. Appl. No. 14/608,087 Arnone, et al. filed Jan. 28, 2015.
U.S. Appl. No. 14/608,093 Arnone, et al. filed Jan. 28, 2015.
U.S. Appl. No. 14/610,897 Arnone, et al. filed Jan. 30, 2015.
U.S. Appl. No. 14/611,077 Arnone, et al. filed Jan. 30, 2015.
U.S. Appl. No. 14/604,629 Arnone, et al. filed Jan. 23, 2015.
U.S. Appl. No. 14/625,475 Arnone, et al. filed Feb. 18, 2015.
U.S. Appl. No. 14/617,852 Arnone, et al. filed Feb. 9, 2015.
U.S. Appl. No. 14/627,428 Arnone, et al. filed Feb. 20, 2015.
U.S. Appl. No. 14/642,427 Arnone, et al. filed Mar. 9, 2015.
U.S. Appl. No. 14/665,991 Arnone, et al. filed Mar. 23, 2015.
U.S. Appl. No. 14/666,010 Arnone, et al. filed Mar. 23, 2015.
U.S. Appl. No. 14/666,022 Arnone, et al. filed Mar. 23, 2015.
U.S. Appl. No. 14/642,623 Arnone, et al. filed Mar. 9, 2015.
U.S. Appl. No. 14/663,337 Arnone, et al. filed Mar. 19, 2015.
U.S. Appl. No. 14/666,284 Arnone, et al. filed Mar. 23, 2015.
U.S. Appl. No. 14/679,885 Arnone, et al. filed Apr. 6, 2015.
U.S. Appl. No. 14/685,378 Arnone, et al. filed Apr. 13, 2015.
U.S. Appl. No. 14/686,675 Arnone, et al. filed Apr. 14, 2015.
U.S. Appl. No. 14/686,678 Arnone, et al. filed Apr. 14, 2015.
U.S. Appl. No. 14/701,430 Arnone, et al. filed Apr. 30, 2015.
U.S. Appl. No. 14/703,721 Arnone, et al. filed May 4, 2015.
U.S. Appl. No. 14/708,138 Arnone, et al. filed May 8, 2015.
U.S. Appl. No. 14/708,141 Arnone, et al. filed May 8, 2015.
U.S. Appl. No. 14/708,160 Arnone, et al. filed May 8, 2015.
U.S. Appl. No. 14/708,161 Arnone, et al. filed May 8, 2015.
U.S. Appl. No. 14/708,162 Arnone, et al. filed May 8, 2015.
U.S. Appl. No. 14/710,483 Arnone, et al. filed May 12, 2015.
U.S. Appl. No. 14/714,084 Arnone, et al. filed May 15, 2015.
U.S. Appl. No. 14/715,463 Arnone, et al. filed May 18, 2015.
U.S. Appl. No. 14/720,620 Arnone, et al. filed May 22, 2015.
U.S. Appl. No. 14/720,624 Arnone, et al. filed May 22, 2015.
U.S. Appl. No. 14/720,626 Arnone, et al. filed May 22, 2015.
U.S. Appl. No. 14/727,726 Arnone, et al. filed Jun. 1, 2015.
U.S. Appl. No. 14/730,183 Arnone, et al. filed Jun. 3, 2015.
U.S. Appl. No. 14/731,321 Arnone, et al. filed Jun. 4, 2015.
U.S. Appl. No. 14/740,078 Arnone, et al. filed Jun. 15, 2015.
U.S. Appl. No. 14/742,517 Arnone, et al. filed Jun. 17, 2015.
U.S. Appl. No. 14/743,708 Arnone, et al. filed Jun. 18, 2015.
U.S. Appl. No. 14/746,731 Arnone, et al. filed Jun. 22, 2015.
U.S. Appl. No. 14/748,122 Arnone, et al. filed Jun. 23, 2015.
U.S. Appl. No. 14/788,581 Arnone, et al. filed Jun. 30, 2015.
U.S. Appl. No. 14/793,685 Arnone, et al. filed Jul. 7, 2015.
U.S. Appl. No. 14/793,704 Arnone, et al. filed Jul. 7, 2015.
U.S. Appl. No. 14/797,016 Arnone, et al. filed Jul. 10, 2015.
U.S. Appl. No. 14/205,303 Arnone, et al., filed Mar. 11, 2014.
U.S. Appl. No. 14/205,306 Arnone, et al., filed Mar. 11, 2014.
U.S. Appl. No. 14/209,485 Arnone, et al., filed Mar. 13, 2014.
U.S. Appl. No. 14/214,310 Arnone, et al., filed Mar. 14, 2014.
U.S. Appl. No. 14/222,520 Arnone, et al., filed Mar. 21, 2014.
U.S. Appl. No. 14/253,813 Arnone, et al., filed Apr. 15, 2014.

(56) References Cited

OTHER PUBLICATIONS

U.S. Appl. No. 14/255,253 Arnone, et al., filed Apr. 17, 2014.
U.S. Appl. No. 14/255,919 Arnone, et al. filed Apr. 17, 2014.
U.S. Appl. No. 14/263,988 Arnone, et al. filed Apr. 28, 2014.
U.S. Appl. No. 14/270,335 Arnone, et al. filed May 5, 2014.
U.S. Appl. No. 14/271,360 Arnone, et al. filed May 6, 2014.
U.S. Appl. No. 13/961,849 Arnone, et al. filed Aug. 7, 2013.
U.S. Appl. No. 13/746,850 Arnone, et al. filed Jan. 22, 2013.
U.S. Appl. No. 14/288,169 Arnone, et al. filed May 27, 2014.
U.S. Appl. No. 14/304,027 Arnone, et al. filed Jun. 13, 2014.
U.S. Appl. No. 14/306,187 Arnone, et al. filed Jun. 16, 2014.
U.S. Appl. No. 14/312,623 Arnone, et al. filed Jun. 23, 2014.
U.S. Appl. No. 14/330,249 Arnone, et al. filed Jul. 14, 2014.
U.S. Appl. No. 14/339,142 Arnone, et al. filed Jul. 23, 2014.
U.S. Appl. No. 14/458,206 Arnone, et al. filed Aug. 12, 2014.
U.S. Appl. No. 14/461,344 Arnone, et al. filed Aug. 15, 2014.
U.S. Appl. No. 14/462,516 Arnone, et al. filed Aug. 18, 2014.
U.S. Appl. No. 14/467,646 Meyerhofer, et al. filed Aug. 25, 2014.
U.S. Appl. No. 14/474,023 Arnone, et al. filed Aug. 29, 2014.
U.S. Appl. No. 14/486,895 Arnone, et al. filed Sep. 15, 2014.
U.S. Appl. No. 14/507,206 Arnone, et al. filed Oct. 6, 2014.
U.S. Appl. No. 14/521,338 Arnone, et al. filed Oct. 22, 2014.
U.S. Appl. No. 14/535,808 Arnone, et al. filed Nov. 7, 2014.
U.S. Appl. No. 14/535,816 Arnone, et al. filed Nov. 7, 2014.
U.S. Appl. No. 14/536,231 Arnone, et al. filed Nov. 7, 2014.
U.S. Appl. No. 14/536,280 Arnone, et al. filed Nov. 7, 2014.
U.S. Appl. No. 14/549,137 Arnone, et al. filed Nov. 20, 2014.
U.S. Appl. No. 14/550,802 Arnone, et al. filed Nov. 21, 2014.
U.S. Appl. No. 14/555,401 Arnone, et al. filed Nov. 26, 2014.
U.S. Appl. No. 14/559,840 Arnone, et al. filed Dec. 3, 2014.
U.S. Appl. No. 14/564,834 Arnone, et al. filed Dec. 9, 2014.
U.S. Appl. No. 14/570,746 Arnone, et al. filed Dec. 15, 2014.
U.S. Appl. No. 14/570,857 Arnone, et al. filed Dec. 15, 2014.
U.S. Appl. No. 14/586,626 Arnone, et al. filed Dec. 30, 2014.
U.S. Appl. No. 14/586,639 Arnone, et al. filed Dec. 30, 2014.
U.S. Appl. No. 15/362,660 Arnone, et al. filed Nov. 28, 2016.
U.S. Appl. No. 15/365,628 Arnone, et al. filed Nov. 30, 2016.
U.S. Appl. No. 15/367,541 Arnone, et al. filed Dec. 2, 2016.
U.S. Appl. No. 15/369,394 Arnone, et al. filed Dec. 5, 2016.
U.S. Appl. No. 15/370,425 Arnone, et al. filed Dec. 6, 2016.
U.S. Appl. No. 15/375,711 Arnone, et al. filed Dec. 12, 2016.
U.S. Appl. No. 15/387,117 Arnone, et al. filed Dec. 21, 2016.
U.S. Appl. No. 15/392,887 Arnone, et al. filed Dec. 28, 2016.
U.S. Appl. No. 15/393,212 Arnone, et al. filed Dec. 28, 2016.
U.S. Appl. No. 15/394,257 Arnone, et al. filed Dec. 29, 2016.
U.S. Appl. No. 15/396,352 Arnone, et al. filed Dec. 30, 2016.
U.S. Appl. No. 15/396,354 Arnone, et al. filed Dec. 30, 2016.
U.S. Appl. No. 15/396,365 Arnone, et al. filed Dec. 30, 2016.
U.S. Appl. No. 15/406,474 Arnone, et al. filed Jan. 13, 2017.
U.S. Appl. No. 15/413,322 Arnone, et al. filed Jan. 23, 2017.
U.S. Appl. No. 15/415,833 Arnone, et al. filed Jan. 25, 2017.
U.S. Appl. No. 15/417,030 Arnone, et al. filed Jan. 26, 2017.
U.S. Appl. No. 15/422,453 Arnone, et al. filed Feb. 1, 2017.
U.S. Appl. No. 15/431,631 Arnone, et al. filed Feb. 13, 2017.
U.S. Appl. No. 15/434,843 Arnone, et al. filed Feb. 16, 2017.
U.S. Appl. No. 15/439,499 Arnone, et al. filed Feb. 22, 2017.
U.S. Appl. No. 15/449,249 Arnone, et al. filed Mar. 3, 2017.
U.S. Appl. No. 15/449,256 Arnone, et al. filed Mar. 3, 2017.
U.S. Appl. No. 15/450,287 Arnone, et al. filed Mar. 6, 2017.
U.S. Appl. No. 15/456,079 Arnone, et al. filed Mar. 10, 2017.
U.S. Appl. No. 15/457,827 Arnone, et al. filed Mar. 13, 2017.
U.S. Appl. No. 15/458,490 Arnone, et al. filed Mar. 14, 2017.
U.S. Appl. No. 15/460,195 Arnone, et al. filed Mar. 15, 2017.
U.S. Appl. No. 15/463,725 Arnone, et al. filed Mar. 20, 2017.
U.S. Appl. No. 15/464,282 Arnone, et al. filed Mar. 20, 2017.
U.S. Appl. No. 15/465,521 Arnone, et al. filed Mar. 21, 2017.
U.S. Appl. No. 15/470,869 Arnone, et al. filed Mar. 27, 2017.
U.S. Appl. No. 15/473,523 Arnone, et al. filed Mar. 29, 2017.
U.S. Appl. No. 15/483,773 Arnone, et al. filed Apr. 10, 2017.
U.S. Appl. No. 15/489,343 Arnone, et al. filed Apr. 17, 2017.
U.S. Appl. No. 15/491,617 Arnone, et al. filed Apr. 19, 2017.

DELAYED WAGERING INTERLEAVED WAGERING SYSTEM

CROSS REFERENCE TO RELATED APPLICATIONS

The present application is a continuation of U.S. patent application Ser. No. 14/855,322, filed Sep. 15, 2015, which claims priority to and the benefit of U.S. Provisional Patent Application No. 62/050,722, filed Sep. 15, 2014, the disclosure of which is incorporated by reference herein in its entirety.

FIELD OF THE INVENTION

Embodiments of the present invention are generally related to communications within data processing systems. More particularly, the present invention relates to the communication and processing of wagering data.

BACKGROUND

The gaming industry has traditionally developed electronic gaming machines (EGMs) that implement simple wagering propositions. The communication and processing needs for these simple wagering propositions are easily met using conventional EGMs.

For example, U.S. Pat. No. 6,905,405 to McClintic describes a conventional gaming device provided with a central processor (CPU) operably coupled to input logic circuitry and output logic circuitry. The input logic circuitry is employed to operably couple the CPU to input devices such as, for example, a touch screen segment or physical button, a coin acceptor, a bill acceptor, a user tracking card reader or a credit/debit card reader. The output logic circuitry is employed to operably couple the CPU with output devices such as, for example, a hopper, a video monitor, meter displays, and a printer. The CPU is also operably coupled to controlling software memory, which includes assigned memory locations storing game software and system software. Such controlling software memory dictates when selected graphics or messages are displayed to a user, as well as when play sequences begin and end and management of wager input and award output. The CPU is also operably coupled to a second memory, which is employed to store data indicative of game statistics, number of plays, number of wins, etc. Controlling software memory, a second memory, or other, ancillary memory store data indicative of winning results, such as data representative of one or more symbol combinations, including winning combinations. Second memory may also be used, for example, to store a bit map of the symbol pattern depicted as a matrix display on video monitor. In operation of the gaming device the CPU carries out instructions of the system software to implement an initial display pattern on the video monitor and to enable the input devices. After a wager is received a user activates an initiator interactive element such as a handle, the physical button or the touch screen to initiate a play sequence. At this point, the game software, in conjunction with a random number generator, generates a random symbol configuration at for a random final outcome comprised of a pattern of symbols for depiction on video monitor. System software then animates the video monitor by simulating the movement of visible representations of symbol carriers including symbols thereon so that the user perceives symbol carrier rotational "movement" of each symbol carrier as well as, optionally, rotational movement of the entire group of symbol carriers about a common axis. Once the visible representations of the symbol carriers have stopped, all of the generated, displayed symbols comprising a winning combination or combinations in the matrix display are identified or flagged. The displayed results (pattern of symbols depicted on the video monitor, which may include symbols received from a remote location, is compared with data stored in game software representing winning combinations to determine if any displayed combination on an active pay line is a winning combination. Any identified winning combination or combinations of symbols are then associated with winnings to be distributed to the user according to a paytable of the game software associated with the various possible winning combinations. The various pay line configurations and required combinations of the various indicia for a winning combination within each pay line reside within the game software and are retrieved for comparison to the randomly generated pattern of indicia depicted on the video monitor.

Operation of another conventional computer gaming system is described in U.S. Pat. No. 6,409,602 issued to Wiltshire et al. A game program is executed on server/host computer. It is then determined whether an image is to be displayed on a screen of a client/terminal computer. If so, an image is sent from the server/host computer to client/terminal computer. The image may include any type of graphical information including a bitmap, a JPEG file, a TIFF file or even an encoded audio/video stream such as a compressed video MPEG stream. The image is generated by game computer program and passed to server/host interface program. In turn, the image is transferred over communication pathways to client/terminal computer via the network services provided by server operating system. The image is received by a client/terminal program executing on the client/terminal computer via the network services provided by client operating system. The client/terminal program then causes the image to be displayed on a screen of the client/terminal computer. It is then determined whether an input command has been entered by the patron using the client/terminal computer. The input command may be a keystroke, movement or clicking of the mouse, a voice activated command or even the clicking of a "virtual button" on a touch screen. The client/terminal program causes the input command to be transmitted back to server/host computer via communication pathways, again using network services provided by the client operating system on one end and server operating system on the other. The command is thus received by the server/host interface program, that, in turn, passes the command back to the game program. The game program processes the input command and updates the state of the game accordingly.

However, more complicated wagering processes need communication and processing systems that are better suited for implementing these more complicated wagering processes. Various aspects of embodiments of the present invention meet such a need.

SUMMARY OF THE INVENTION

Systems and methods in accordance with embodiments of the invention provide a communication and data processing system constructed for a delayed wager interleaved wagering system.

An embodiment includes an interactive processing device constructed to: provide an interactive application display associated with an interactive application provided by the interactive processing device; request, from the process controller, wager actuator data; responsive to receiving the wager actuator data, automatically configure the display to provide a wager actuator; communicate, to the process controller, wager actuator activation data based on detection of an indication to activate the wager actuator; receive, from the process controller, wagering telemetry data and application resource data; responsive to receiving the wagering telemetry data, automatically configure the display based on the wagering telemetry data; and automatically incorporate the application resource data into the interactive application; a wager server constructed to: continuously monitor the process controller for wager request data; responsive to receiving the wager request data, automatically determine a wager outcome based on the wager request data; and communicate, to the process controller, wager outcome data; and the process controller operatively connecting the interactive processing device and the wager server, the process controller constructed to: receive, from the interactive processing device, the wager actuator activation data; generate the wager actuator data; scan the wager actuator activation data to determine whether to trigger a wager request; when the wager request is triggered, generate wager request data; receive, from the wager server, the wager outcome data; responsive to receiving the data, scan the wager outcome data; automatically determine the wagering telemetry data and the application resource data based on the wager outcome data; and communicate, to the interactive processing device, the wagering telemetry data and the application resource data.

In a further embodiment, the interactive processing device and the process controller are constructed from the same device, and the process controller is operatively connected to the wager server using a communication link.

In a further embodiment, the wager server and the process controller are constructed from the same device, and the process controller is operatively connected to the interactive processing device using a communication link.

In a further embodiment, the interactive processing device is further constructed to detect an indication to activate the wager actuator.

In a further embodiment, the wager actuator is displayed with one or more other previously generated wager actuators.

In a further embodiment, the wager actuator data comprises a wager amount, and a size of the wager actuator displayed is based on the wager amount.

In a further embodiment, the process controller continuously monitors for application telemetry data.

A further embodiment includes a credit processing controller; and an enclosure constructed to mount: a user input device operatively connected to the interactive controller; a user output device operatively connected to the interactive controller; a credit input device operatively connected to the credit processing controller; and a credit output device operatively connected to the credit processing controller.

An embodiment includes a wager server of the delayed wager interleaved wagering system, the wager server constructed to: continuously monitor the process controller for wager request data; responsive to receiving the wager request data, automatically determine a wager outcome based on the wager request data; and communicate, to the process controller, wager outcome data; and the process controller of the delayed wager interleaved wagering system operatively connecting the wager server to an interactive processing device using a communication link, the process controller constructed to: receive, from the interactive processing device, wager actuator activation data; generate wager actuator data; scan the wager actuator activation data to determine whether to trigger a wager request; when the wager request is triggered, generate wager request data; receive, from the wager server, the wager outcome data; responsive to receiving the data, scan the wager outcome data; automatically determine the wagering telemetry data and the application resource data based on the wager outcome data; and communicate, to the interactive processing device, the wagering telemetry data and the application resource data.

An embodiment includes an interactive processing device constructed to: provide an interactive application display associated with an interactive application provided by the interactive processing device; request, from the process controller, wager actuator data; responsive to receiving the wager actuator data, automatically configure the display to provide a wager actuator; communicate, to the process controller, wager actuator activation data based on detection of an indication to activate the wager actuator; receive, from the process controller, wagering telemetry data and application resource data; responsive to receiving the wagering telemetry data, automatically configure the display using the wagering telemetry data; and automatically incorporate the application resource data into the interactive application; and the process controller of the delayed wager interleaved wagering system operatively connecting the interactive processing device to a wager server, the process controller constructed to: receive, from the interactive processing device, the request for the wager actuator data; generate the wager actuator data; communicate, to the interactive processing device, the wager actuator data; receive, from the interactive processing device, the wager actuator activation data; scan the wager actuator activation data to determine whether to trigger a wager request; when the wager request is triggered, generate wager request data; receive, from the wager server, the wager outcome data; responsive to receiving the data, scan the wager outcome data; automatically determine the wagering telemetry data and the application resource data based on the wager outcome data; and communicate, to the interactive processing device, the wagering telemetry data and the application resource data.

DETAILED DESCRIPTION

Figure 1A:
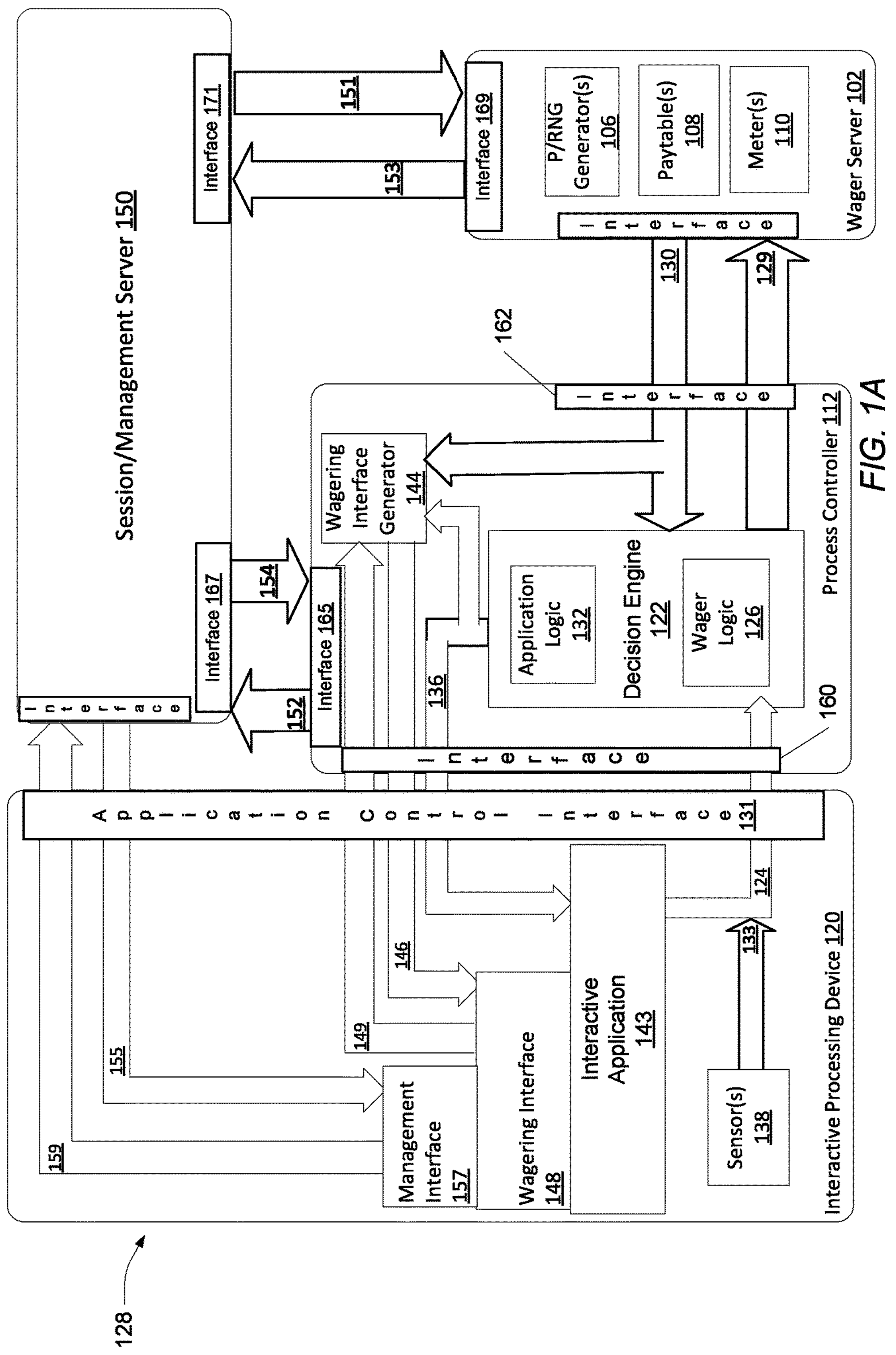
FIG. 1A is a diagram of a structure of a delayed wager interleaved wagering system in accordance with various embodiments of the invention.

A delayed wager interleaved wagering system interleaves wagering with non-wagering activities. In some embodiments of a delayed wager interleaved wagering system, an interactive application executed by an interactive processing device provides non-wagering interactive components of the delayed wager interleaved wagering system. The interactive processing device is operatively connected to a process controller that manages and configures the interactive processing device and the interactive application, and determines when wagers should be interleaved with the operations of the interactive application. The process controller is further operatively connected to a wager server that provides one or more wagering propositions for one or more wagers.

In some embodiments, the interactive processing device also provides a wagering interface that is used to receive commands and display data for a wagering process, including but not limited to a wager outcome of a wager made in accordance with a wagering proposition. The content of the wagering interface is controlled by the process controller and includes content provided by the wager server.

In various embodiments, the interactive processing device provides a management interface used to manage a user profile including an electronic wallet for deposit and withdrawals of credits used for wagering.

Many different types of interactive applications may be utilized with the delayed wager interleaved wagering system. In some embodiments, the interactive application reacts to the physical activity of a user. In these embodiments, the interactive application senses user interactions with the interactive application through one or more sensors that monitor the user's physical activities. Such sensors may include, but are not limited to, physiological sensors that monitor the physiology of the user, environmental sensors that monitor the physical environment of the interactive processing device, accelerometers that monitor changes in motion of the interactive processing device, and location sensors that monitor the location of the interactive processing device such as global positioning sensors.

In some embodiments, the interactive application is skill-based and interacts with the user by sensing skillful interactions with an interactive display generated by the interactive application.

In some embodiments, the interactive application is a tool used to achieve some useful goal.

In operation, the interactive application generates various types of interactive elements in an interactive application environment. In some embodiments, these interactive elements are interactive application resources utilized within the interactive application environment to provide an interactive experience for a user. Wagers of credits or interactive elements are made in accordance with a wagering proposition as automatically triggered by interaction with one or more of the interactive elements of the interactive application. Wager outcomes of wagers of credits or interactive elements made in accordance with the wagering proposition can cause consumption, loss or accrual of credits or interactive elements.

In accordance with some embodiments, wager outcomes of wagering events can influence interactive elements in the interactive application environment such as, but not limited to, automatically providing one or more new interactive elements, automatically restoring one or more consumed interactive elements, automatically causing the loss of one or more interactive elements, and automatic restoration or placement of one or more fixed interactive elements.

In various embodiments, the wagers may be made using one or more credits (Cr).

In some embodiments, Cr can be one or more credits that are purchased using, and redeemed in, a real world currency having a real world value.

In many embodiments, Cr can be one or more credits in a virtual currency. Virtual currency is an alternate currency that can be acquired, purchased or transferred by or to a user, but does not necessarily directly correlate to a real world currency. In many such embodiments, Cr in a virtual currency are allowed to be purchased using a real world currency but are prevented from being redeemed in a real world currency having a real world value.

In several embodiments, interaction with the interactive elements of the interactive application, application environment credit (AC) can be optionally consumed and/or accrued within the interactive application as a result of interaction with the interactive elements. AC can be in the form of, but is not limited to, application environment credits, experience points, and points generally.

In various embodiments, AC is awarded on the basis of skillful interactions with the interactive elements of a skill-based interactive application. The skill-based interactive application can have one or more scoring criteria, embedded within a process controller and/or an interactive processing device that provides the skill-based interactive application, that can be used to determine performance against one or more goals of the skill-based interactive application.

In many embodiments, AC can be used to purchase in-application items, including but not limited to, application interactive elements that have particular properties, power ups for existing items, and other item enhancements.

In some embodiments, AC may be used to earn entrance into a sweepstakes drawing, to earn entrance in a tournament with prizes, to score in the tournament, and/or to participate and/or score in any other game event.

In several embodiments, AC can be stored on a user-tracking card or in a network-based user tracking system where the AC is attributed to a specific user.

In many embodiments, a wagering proposition includes a wager of AC for a wager outcome of a randomly generated payout of interactive application AC, interactive elements, and/or interactive application objects in accordance with a wagering proposition.

In a number of embodiments, a wager of an amount of Cr results in a wager outcome of a payout of AC, interactive elements, and/or interactive application objects that have a Cr value if cashed out.

In some embodiments, such as when an interactive application is a skill-based interactive application, interactive application objects include in-application objects that may be utilized to enhance interactions with the skill-based interactive application. Such objects include, but are not limited to, power-ups, enhanced in-application items, and the like. In some embodiments, the interactive application objects include objects that are detrimental to interactions with the skill-based interactive application such as, but not limited to, obstructions in the skill-based interactive application space, a temporary handicap, an enhanced opponent, and the like.

In some embodiments, interactive elements in an interactive application include, but are not limited to, enabling interactive elements (EIE) that are interactive application environment resources utilized during interaction with an interactive application and whose utilization automatically triggers execution of a wager in accordance with a wagering proposition. In some embodiments, interactive elements in an interactive application include, but are not limited to, a reserve enabling interactive element (REIE), that is an interactive element that is automatically converted into one or more enabling interactive elements upon occurrence of a release event during an interactive session of an interactive application. In yet another embodiment, interactive elements in an interactive application include, but are not limited to, an actionable interactive element (AIE) that is an interactive element that is acted upon during a session of the interactive application to automatically trigger a wager in accordance with a wagering proposition and may or may not be restorable during normal interaction with the interactive application. In yet another embodiment, interactive elements in an interactive application include a common enabling interactive element (CEIE) that is an interactive element that the interactive application shares between two or more users and causes a wagering event and associated wager to be automatically triggered in accordance with the wagering proposition when interacted with during a session. In some embodiments, a user can utilize interactive elements during interactions with a controlled entity (CE) provided by an interactive application to a user.

In accordance with some embodiments of a delayed wager interleaved wagering system, the triggering of the wagering event and/or wager can be dependent upon an interactive application environment variable such as, but not limited to, a required object (RO), a required environmental condition (REC), or a controlled entity characteristic (CEC). A RO is a specific interactive application object in an interactive application acted upon for an AE to be completed. A non-limiting example of an RO is a specific key needed to open a door. An REC is an interactive application state present within an interactive application for an AE to be completed. A non-limiting example of an REC is daylight whose presence enables a character to walk through woods. A CEC is a status of a controlled entity (CE) within an interactive application for an AE to be completed. A non-limiting example of a CEC is requirement that a CE have full health points before entering battle. Although various interactive application resources such as, but not limited to, the types of interactive application interactive elements as discussed herein may be used to automatically trigger a wager in accordance with a wagering proposition, one skilled in the art will recognize that any interactive application resource can be utilized in a delayed wager interleaved wagering system to automatically trigger a wager.

In several embodiments, a delayed wager interleaved wagering system can utilize a process controller to continuously monitor use of the interactive application executed by an interactive processing device in order to detect a trigger of a wagering event and automatically trigger a wager based on the wagering event. The trigger for the wagering event can be detected by the process controller from the utilization of the interactive application in accordance with at least one wagering event occurrence rule. The trigger of the wagering event can be communicated to a wager server. In response to notification of the trigger, the wager server executes a wager in accordance with a wagering proposition. In addition, use of an interactive application in a delayed wager interleaved wagering system can be controlled by the process controller based upon the wager outcome.

In several embodiments, a wagering event occurrence can be determined from one or more application environment variables within an interactive application environment that are used to trigger a wager and/or associated wager in accordance with a wagering proposition. Application environment variables can include, but are not limited to, passage of a period of time during delayed wager interleaved wagering system interactive application use, a result from a delayed wager interleaved wagering system interactive application session (such as, but not limited to, achieving a goal or a particular score), consumption of an interactive element, or an interaction that achieves a combination of interactive elements to be associated with a user profile.

In numerous embodiments, an interactive application instruction is an instruction by a process controller to an interactive processing device and/or an interactive application of the interactive processing device to modify a state of an interactive application or modify one or more interactive application resources or interactive elements. In some embodiments, the interactive application commands may be automatically generated by the process controller using one or more of a wager outcome and/or application environment variables. An interactive application instruction can be used by a process controller control many processes of an interactive application, such as, but not limited to, an causing an addition of a period of time available for a current interactive application session for the interactive application, an addition of a period of time available for a future delayed wager interleaved wagering system interactive application session or any other modification to the interactive application interactive elements that can be utilized during an interactive application session. In some embodiments, an interactive application instruction can be used by the process controller to modify a type of interactive element whose consumption triggers a wagering event occurrence. In many embodiments, an interactive application instruction can be used by the process controller to modify a type of interactive element whose consumption is not required in a wagering event occurrence.

In several embodiments, a process controller of a delayed wager interleaved wagering system may provide for a communications interface for asynchronous communications between a wager server and an interactive application provided by an interactive processing device, by operatively connecting the interactive processing device, and thus the interactive processing device's interactive application, with the wager server.

In some embodiments, asynchronous communications provided for by a delayed wager interleaved wagering system may reduce an amount of idle waiting time by an interactive processing device of the delayed wager interleaved wagering system, thus increasing an amount of processing resources that the interactive processing device may provide to an interactive application or other processes of the interactive processing device. In many embodiments, asynchronous communications provided for by a delayed wager interleaved wagering system reduces an amount of idle waiting time by a wager server, thus increasing an amount of processing resources that the wager server may provide to execution of wagers to determine wager outcomes, and other processes provided by the wager server.

In some embodiments, a wager server of a delayed wager interleaved wagering system may be operatively connected to a plurality of interactive processing devices through one or more process controllers and the asynchronous communications provided for by the one or more process controllers allows the wager server to operate more efficiently by providing wager outcomes to a larger number of interactive processing devices than would be achievable without the one or more process controllers of the delayed wager interleaved wagering system.

In some embodiments, a delayed wager interleaved wagering system including a process controller operatively connected to a wager server and operatively connected to an interactive processing device may provide for simplified communication protocols for communications of the interactive processing device as the interactive processing device may communicate interactions with an interactive application provided by the interactive processing device to the process controller without regard to a nature of a wagering proposition to be interleaved with processes of the interactive application.

In various embodiments, a delayed wager interleaved wagering system including a process controller operatively connected to a wager server and operatively connected to an interactive processing device may provide for simplified communication protocols for communications of the wager server as the wager server may receive wager requests and communicate wager outcomes without regard to a nature of an interactive application provided by the interactive processing device.

In some embodiments, a delayed wager interleaved wagering system including a process controller operatively connecting a wager server to an interactive processing device may provide for reduced processing requirement for the interactive processing device by offloading the execution of a pseudo random or random number generator from the interactive processing device to the wager server. In various such embodiments, additional processing resources may be made available to graphics processing or other processing intensive operations by the interactive processing device because of the offloaded random number processing.

In various embodiments, a delayed wager interleaved wagering system including a process controller operatively connecting a wager server to an interactive processing device provides for operation of the interactive processing device in an unsecure location or manner, while providing for operation of the wager server in a secure location or manner.

In some embodiments, a delayed wager interleaved wagering system including a process controller operatively connecting a wager server to an interactive processing device allows the interleaved wagering system to have regulated components coupled to unregulated components in a heterogeneous regulated environment. For example, in several such embodiments, the interactive processing device may be a device that is not regulated by a wagering regulatory agency whereas the wager server is regulated by the wagering regulatory agency. A process controller of a delayed wager interleaved wagering system may provide for isolation of the processing of the interactive processing device from the processing of the wager server. In such a heterogeneous regulatory environment, the process controller may or may not be itself a regulated by the wagering regulatory authority. In addition, components of an interactive application executed by the interactive processing device may be either regulated or unregulated by the wagering regulatory agency.

Delayed Wager Wagering Interleaved Systems

FIG. 1A is a diagram of a structure of a delayed wager interleaved wagering system in accordance with various embodiments of the invention. The delayed wager interleaved wagering system 128 includes an interactive processing device 120, a process controller 112, and a wager server 102. The interactive processing device 120 is operatively connected to, and communicates with, the process controller 112. The process controller 112 is also operatively connected to, and communicates with, the wager server 102.

In several embodiments, the wager server 102 is a controller for providing one or more wagering propositions provided by the delayed wager interleaved wagering system 128 and automatically executes wagers in accordance with the wagering propositions as instructed by the process controller 112. Types of value of a wager can be one or more of several different types. Types of value of a wager can include, but are not limited to, a wager of an amount of Cr corresponding to a real currency or a virtual currency, a wager of an amount of AC earned through interaction with an interactive application, a wager of an amount of interactive elements of an interactive application, and a wager of an amount of objects used in an interactive application. A wager outcome determined for a wager in accordance with a wagering proposition can increase or decrease an amount of the type of value used in the wager, such as, but not limited to, increasing or decreasing an amount of Cr for a wager of Cr. In various embodiments, a wager outcome determined for a wager in accordance with a wagering proposition can increase or decrease an amount of a type of value that is different than a type of value of the wager, such as, but not limited to, increasing an amount of an object of an interactive application for a wager of Cr.

In many embodiments, the wager server 102 includes one or more pseudo random or random number generators (P/RNG) 106 for generating random results, one or more paytables 108 for determining a wager outcome from the random results, and one or more credit or value meters 110 for storing amounts of wagered and won credits.

In operation, the one or more P/RNGs 106 execute processes that generate random or pseudo random results. The one or more paytables 108 are tables that the wager server 102 uses to map the random or pseudo random results to a wager outcome. The wager outcome can included, but is not limited to, an amount of Cr, AC, and/or interactive elements or objects won as a function of multiuser interleaved wagering system use. There can be one or more paytables 108 in the wager server 102. The paytables 108 are used to implement one or more wagering propositions in conjunction with a random output of the one or more P/RNGs. For example, in one embodiment of a wager server, the wager server continuously generates pseudo random numbers using the P/RNGs 106. A most current pseudo random number is stored in a buffer. When the wager server receives a request for a wager outcome, the wager server uses the stored pseudo random number along with a paytable that the wager server selects from the paytables 108. The selected paytable includes a mapping of values in the range of values of the pseudo random number to specified multipliers to be applied to an amount of Cr, AC and/or interactive application objects wagered. The multiplier is applied to the amount of Cr, AC and/or interactive application objects wagered and the resultant outcome is a wagering outcome for a wagering proposition.

In some embodiments, a range of the value of the pseudo random number is mapped to a symbol representing a random element of a traditional wagering proposition, and the mapped to symbol is used in conjunction with the paytable. In one such embodiment, the pseudo random number is mapped to a virtual card of a deck of virtual cards. In another such embodiment, the pseudo random number is mapped to a virtual face of a virtual die. In yet another such embodiment, the pseudo random number is mapped to symbol of a virtual reel strip on a virtual reel slot machine. In yet another such embodiment, the pseudo random number is mapped to a pocket of a virtual roulette wheel. In some embodiments, two or more pseudo numbers are mapped to appropriate symbols to represent a completed wagering proposition. In one such embodiment, two or more pseudo numbers are mapped to faces of two or more virtual dice to simulate a random outcome generated by throwing two or more dice. In another such embodiment, multiple pseudo random numbers are mapped to virtual cards from a virtual deck of cards without replacement. In yet another such embodiment, two or more pseudo random numbers are mapped to two or more virtual reel strips to create stop positions for a virtual multi-reel slot machine.

In some embodiments, a wager server executes a wager in accordance with a wagering proposition by executing wager execution commands that define processes of a wagering proposition where the wager execution commands are formatted in a scripting language. In operation, a decision engine of a process controller generates the wager execution commands in the form of a script written in the scripting language. The script includes the wager execution commands that describe how the wager server is to execute the wagering proposition. The completed script is encoded as wager execution instruction data and communicated to the wager server by the process controller. The wager server receives the wager execution instruction data and parses the script encoded in the wager execution instruction data and executes the commands included in the script to execute the wager.

In some embodiments, a wager server executes a wager in accordance with a wagering proposition by executing wager execution commands that define processes of the wagering interface. In operation, a decision engine of a process controller generates the wager execution commands and encodes the wager execution commands into wager execution instruction data that are communicated to the wager server by the process controller. The wager server receives the wager execution instruction data and executes the commands encoded in the wager execution instruction data to execute the wager.

In various embodiments, the interactive processing device 120 provides an interactive application 143 and provides human input devices (HIDs) and output devices for interacting with a user. The interactive processing device 120 provides for interactions 142 with the interactive application 143 by receiving input from a user through the HIDs and providing outputs such as video, audio and/or other sensory output to the user using the output devices.

The interactive processing device 120 is operatively connected to, and communicates with, the process controller 112. The interactive processing device communicates application telemetry data 124 to the process controller 112 and receives application instruction and resource data 136 from the process controller 112. Via the communication of application instruction and resource data 136, the process controller 112 can control the processing of the interactive processing device by communicating interactive application commands and resources including control parameters to the interactive application 143 during the interactive application's execution by the interactive processing device 120.

In some embodiments, during execution of the interactive application 143 by the interactive processing device 120, the interactive processing device 120 communicates, as application telemetry data, interactions with the interactive application to the process controller 112. The application telemetry data 124 includes, but is not limited to, utilization of the interactive elements in the interactive application 143.

In some embodiments, the interactive application 143 is a skill-based interactive application. In such embodiments, execution of the skill-based interactive application 143 by the interactive processing device 120 is based on a user's skillful interaction with the skill-based interactive application, such as, but not limited to, the user's utilization of the interactive elements of the skill-based interactive application 143 during the user's skillful interaction with the skill-based interactive application 143. In such an embodiment, the process controller 112 communicates with the interactive processing device 120 in order to allow the coupling of the skill-based interactive application 143 to wagers made in accordance with a wagering proposition of the wager controller 102.

In some embodiments, the interactive processing device 120 includes one or more sensors 138 that sense various aspects of the physical environment of the interactive processing device 120. Examples of sensors include, but are not limited to: global positioning sensors (GPSs) for sensing communications from a GPS system to determine a position or location of the interactive processing device; temperature sensors; accelerometers; pressure sensors; and the like. Sensor telemetry data 133 is communicated by the interactive processing device to the process controller 112 as part of the application telemetry data 124. The process controller 112 receives the sensor telemetry data 133 and uses the sensor telemetry data to make wager decisions.

In many embodiments, the interactive processing device 120 includes a wagering interface 148 used to display wagering data.

In various embodiments, an application control interface 131 resident in the interactive processing device 120 provides an interface between the interactive processing device 120 and the process controller 112. In some embodiments, the application control interface 131 implements an interactive processing device to process controller communication protocol employing an interprocess communication protocol so that the interactive processing device and the process controller may be implemented on the same device. In some embodiments, the application control interface 131 implements an interactive processing device to process controller communication protocol employing an interdevice communication protocol so that the interactive processing device and the process controller may be implemented on different devices. In various embodiments, the application control interface 131 implements an interactive processing device to process controller communication protocol employing a networking protocol so that the interactive processing device and the process controller may be implemented on different devices connected by a network.

In some embodiments, the process controller 112 includes an interactive processing device interface 160 to an interactive processing device. The interactive processing device interface 160 provides for the communication of data between the interactive processing device and the process controller, including but not limited to wager telemetry data 146, application commands and resources 136, application telemetry data 124, and sensor telemetry data 133.

In various embodiments, communication of outgoing data is achieved by the process controller encoding outgoing data to be communicated into a signal and transmitting the signal to the interactive processing device. Communication of incoming data is achieved by the process controller receiving from the interactive communication device signals encoding the incoming data. The process controller decodes the signals to obtain the incoming data. In some such embodiments, the interactive processing device interface 160 implements a process controller to interactive processing device communication protocol as an interdevice communication protocol so that the interactive processing device and the process controller may be implemented on different devices. The interdevice protocol may utilize a wired communication bus or wireless connection as a physical layer. In yet other such embodiments, the interactive processing device interface 160 implements a process controller to interactive processing device communication protocol as a networking protocol so that the interactive processing device and the process controller may be implemented on different devices operatively connected by a network. The networking protocol may utilize a wired communication bus or wireless connection as a physical layer. In many such embodiments, the network includes a cellular telephone network or the like and the interactive processing device is a mobile device such as a smartphone or other device capable of using the telephone network.

In some embodiments, communication is achieved by the interactive processing device interface 160 implementing a process controller to interactive processing device communication protocol as an interprocess communication protocol so that the interactive processing device and the process controller may be implemented on the same device.

In some embodiments, the process controller 112 includes a session/management server interface 165 to a session/management server. The session/management server interface 165 provides for communication of data between the process controller 112 and the session/management server, including but not limited to session control data 152 and session telemetry data 154.

In various embodiments, communication of outgoing data is achieved by the process controller encoding outgoing data to be communicated into a signal and transmitting the signal to the session/management server. Communication of incoming data is achieved by the process controller receiving from the session/management server signals encoding the incoming data. The process controller decodes the signals to obtain the incoming data. In some such embodiments, the session/management server interface 165 implements a process controller to session/management communication protocol as an interdevice communication protocol so that the session/management server and the process controller may be implemented on different devices. The interdevice protocol may utilize a wired communication bus or wireless connection as a physical layer. In yet other such embodiments, the session/management server interface 165 implements a process controller to session/management server communication protocol as a networking protocol so that the session/management server and the process controller may be implemented on different devices operatively connected by a network. The networking protocol may utilize a wired communication bus or wireless connection as a physical layer.

In some embodiments, communication is achieved by the session/management server interface 165 implementing a process controller to session/management server communication protocol as an interprocess communication protocol so that the session/management server and the process controller may be implemented on the same device.

In various embodiments, the process controller 112 includes a wager server interface 162 to the wager server 102. The wager server interface 162 provides for communication of data between the process controller 112 and the wager server, including but not limited to wager outcome data 130 and wager execution commands 129.

In various embodiments, communication of outgoing data is achieved by the process controller encoding outgoing data to be communicated into a signal and transmitting the signal to the wager server. Communication of incoming data is achieved by the process controller receiving from the wager server signals encoding the incoming data. The process controller decodes the signals to obtain the incoming data. In some such embodiments, the wager server interface 162 implements a process controller to wager server communication protocol as an interdevice communication protocol so that the session/management server and the process controller may be implemented on different devices. The interdevice protocol may utilize a wired communication bus or wireless connection as a physical layer. In yet other such embodiments, the session/management server interface 165 implements a process controller to session/management server communication protocol as a networking protocol so that the session/management server and the process controller may be implemented on different devices operatively connected by a network. The networking protocol may utilize a wired communication bus or wireless connection as a physical layer.

In some embodiments, communication is achieved by the session/management server interface 165 implementing a process controller to session/management server communication protocol as an interprocess communication protocol so that the session/management server and the process controller may be implemented on the same device.

In many embodiments, process controller 112 provides an interface between the interactive application 143 provided by the interactive processing device 120 and a wagering proposition provided by the wager server 102.

The process controller 112 includes a rule-based decision engine 122 that receives telemetry data, such as application telemetry data 124 and sensor telemetry data 133, from the interactive processing device 120. The rule-based decision engine 122 uses the telemetry data, along with wager logic 126 to generate wager execution commands 129 that are used by the process controller 112 to command the wager server 102 to execute a wager. The wager execution instruction data is communicated by the process controller 112 to the wager server 102. The wager server 102 receives the wager execution instruction data 129 and automatically executes a wager in accordance with the wager execution instruction data 129.

In an embodiment, the application telemetry data 124 used by the decision engine 122 encodes data about the operation of the interactive application 143 executed by the interactive processing device 120. In some embodiments, the application telemetry data 124 encodes interactions of a user, such as a user's interaction with an interactive element of the interactive application 143. In many embodiments, the application telemetry data 124 includes a state of the interactive application 143, such as values of variables that change as the interactive application 143 is executed. The decision engine 122 includes one or more rules as part of wager logic 126 used by the decision engine 122 to determine when a wager should be automatically triggered. Each rule includes one or more variable values constituting a pattern that is to be matched by the process controller 112 using the decision engine 122 to one or more variable values encoded in the application telemetry data 124. Each rule also includes one or more actions that are to be taken if the pattern is matched. Actions can include automatically generating wager execution instruction data 129 and communicating the wager execution instruction data 129 to the wager server 102, thus commanding the wager server to automatically execute a wager as described herein. During operation, the decision engine 122 receives application telemetry data 124 from the interactive processing device 124 via interface 160. The decision engine 122 performs a matching process of matching the variable values encoded in the application telemetry data 124 to one or more variable patterns of one or more rules. If a match between the variable values and a pattern of a rule is determined, then the process controller 112 performs the action of the matched rule.

In some embodiments, the application telemetry data 124 includes, but is not limited to, application environment variables that indicate a state of the interactive application 143, interactive processing device data indicating a state of the interactive processing device 120, and interactions with the interactive application 143 during execution of the interactive application 143 by the interactive processing device 120. The wager execution instruction data 129 may include, but are not limited to, an amount and type of the wager, a trigger of the wager, and a selection of a paytable to be used when executing the wager.

In some embodiments, the process controller 112 receives wager outcome data 130 from the wager server 102. The decision engine 122 uses the wager outcome data 130, in conjunction with the telemetry data 124 and application logic 132, to automatically generate interactive application instruction and resource data 136 that the process controller 112 communicates to the interactive processing device 120 via interfaces 160 and 131.

In an embodiment, the wager outcome data 130 used by a decision engine encodes data about the execution of a wager executed by the wager server 102. In some embodiments, the wager outcome data 130 encodes values of variables including an amount of credits wagered, an amount of credits won and values of credits stored in the one or more meters 110 of the wager server. In many embodiments, the wager outcome data includes a state of the wager server 102, such as values of variables that change as the wager server 102 executes wagers. The decision engine 122 includes one or more rules as part of application logic 132 used by the decision engine 122 to automatically generate the interactive application instruction and resource data 136 that is then communicated to the interactive processing device 120. Each rule includes one or more variable values constituting a pattern that is to be matched to one or more variable values encoded in the wager outcome data 130. Each rule also includes one or more actions that are to be automatically taken by the process controller 112 if the pattern is matched. Actions can include automatically generating interactive application instruction and resource data 136 and using the interactive application instruction and resource data 136 to control the interactive processing device 120 to affect execution of the interactive application 143 as described herein. During operation, the process controller 112 receives the wager outcome data 130 from the wager server 102 via interface 162. The process controller 112 uses the decision engine 122 to match the variable values encoded in the wager outcome data to one or more patterns of one or more rules of the application logic 132. If a match between the variable values and a pattern of a rule is found, then the process controller automatically performs the action of the matched rule. In some embodiments, the process controller 112 uses the application telemetry data 124 received from the interactive processing device 120 in conjunction with the wager outcome data 130 to generate the interactive application instruction and resource data 136.

The interactive processing device receives the interactive application commands and resource data 136 and automatically uses the interactive application instruction and resource data 136 to configure and command the processes of the interactive application 143.

In some embodiments, the interactive application 143 operates utilizing a scripting language. The interactive application 143 parses scripts written in the scripting language and executes commands encoded in the scripts and sets variable values as defined in the scripts. In operation of such embodiments, the process controller 112 automatically generates interactive application instruction and resource data 136 in the form of scripts written in the scripting language that are communicated to the interactive processing device 120 during execution of the interactive application 143. The interactive processing device 120 receives the scripts and passes them to the interactive application 143. The interactive application 143 receives the scripts, parses the scripts and automatically executes the commands and sets the variable values as encoded in the scripts.

In many embodiments, the interactive application 143 automatically performs processes as instructed by commands communicated from the process controller 112. The commands command the interactive application 143 to perform specified operations such as executing specified commands and/or setting the values of variables utilized by the interactive application 143. In operation of such embodiments, the process controller 112 automatically generates commands that are encoded into the interactive application instruction and resource data 136 that are communicated to the interactive processing device 120. The interactive processing device 120 passes the application instruction and resource data 136 to the interactive application 143. The interactive application parses the application instruction and resource data and automatically performs operations in accordance with the commands encoded in the interactive application instruction and resource data 136.

In many embodiments, the process controller 112 includes a pseudo random or random result generator used to generate random results that are used by the decision engine 122 to generate portions of the interactive application instruction and resource data 136.

In various embodiments, the process controller 112 uses the rule-based decision engine 122 to automatically determine an amount of AC to award based at least in part on interactions with the interactive application 143 of the delayed wager interleaved wagering system as determined by the process controller 112 from the application telemetry data 124. In some embodiments, the process controller 112 may also use the wager outcome data 130 to determine the amount of AC that should be awarded.

In numerous embodiments, the interactive application 143 is a skill-based interactive application and the AC is awarded for skillful interaction with the interactive application.

In some embodiments, the interactive application instruction and resource data 136 are communicated to a wagering interface generator 144. The wagering interface generator 144 also receives wager outcome data 130. The process controller uses the wagering interface generator 144, the interactive application instruction and resource data 136 and the wager outcome data 130 to automatically generate wager telemetry commands 146 used by the process controller 112 to command the interactive processing device 120 to automatically generate a wagering interface 148 describing a state of wagering and credit accumulation and loss for the delayed wager interleaved wagering system. In some embodiments, the wager telemetry data 146 may include, but is not limited to, amounts of AC and interactive elements earned, lost or accumulated through interaction with interactive application, and Cr, AC and interactive elements amounts won, lost or accumulated as determined from the wager outcome data 130 and the one or more meters 110.

In some embodiments, the wager outcome data 130 also includes data about one or more game states of a wagering proposition as executed by the wager server 102. In various such embodiments, the wagering interface generator 144 generates a wagering process display and/or wagering state display using the one or more states of the wagering proposition. The wagering process display and/or wagering state display is included in the wager telemetry data 146 that is communicated to the interactive processing device 120. The wagering process display and/or wagering state display is automatically displayed by the interactive processing device 120 using the wagering interface 148. In other such embodiments, the one or more states of the wagering proposition are communicated to the interactive processing device 120 and the interactive processing device 120 is instructed to automatically generate the wagering process display and/or wagering state display of the wagering interface 148 using the one or more states of the wagering proposition for display.

In some embodiments, the wager outcome data 130 includes game state data about execution of the wagering proposition, including but not limited to a final state, intermediate state and/or beginning state of the wagering proposition. For example, in a wagering proposition that is based on slot machine math, the final state of the wagering proposition may be reel positions, in a wagering proposition that is based on roulette wheel math, the final state may be a pocket where a ball may have come to rest, in a wagering proposition that is a based on card math, the beginning, intermediate and final states may represent a sequence of cards being drawn from a deck of cards, etc.

In some embodiments, the interactive processing device 120 generates a wagering interface by executing commands that define processes of the wagering interface where the commands are formatted in a scripting language. In operation, a wagering interface generator of a process controller generates commands in the form of a script written in the scripting language. The script includes commands that describe how the interactive processing device is to display wagering outcome data. The completed script is encoded as wager telemetry data and communicated to the interactive processing device by the process controller. The interactive processing device receives the wager telemetry data and parses the script encoded in the wager telemetry data and executes the commands included in the script to generate the wagering interface.

In many embodiments, an interactive processing device generates a wagering interface based on a document written in a document markup language that includes commands that define processes of the wagering interface. In operation, a wagering interface generator of a process controller generates a document composed in the document markup language. The document includes commands that describe how the interactive processing device is to display wagering outcome data. The completed document is encoded as wager telemetry data and communicated to the interactive processing device by the process controller. The interactive processing device receives the wager telemetry data and parses the document encoded in the wager telemetry data and executes the commands encoded into the document to generate the wagering interface.

In some embodiments, an interactive processing device generates a wagering interface by executing commands that define processes of the wagering interface. In operation, a wagering interface generator of a process controller generates the commands and encodes the commands into wager telemetry data that is communicated to the interactive processing device by the process controller. The interactive processing device receives the wager telemetry data and executes the commands encoded in the wager telemetry data to generate the wagering interface.

In various embodiments, an interactive processing device includes a data store of graphic and audio display resources that the interactive processing device uses to generate a wagering interface as described herein.

In many embodiments, a process controller communicates graphic and audio display resources as part of wager telemetry data to an interactive processing device. The interactive processing device uses the graphic and audio display resources to generate a wagering interface as described herein.

When a user interacts with the wagering interface 148, wagering interface telemetry data 149 is generated by the wagering interface 148 and communicated by the interactive processing device 120 to the process controller 112 using interfaces 131 and 160.

The process controller 112 can further operatively connect to the wager server 102 to determine an amount of credit or interactive elements available and other wagering metrics of a wagering proposition. Thus, the process controller 112 may affect an amount of Cr in play for participation in the wagering events of a wagering proposition provided by the wager server 102 in some embodiments. The process controller 112 may additionally include various audit logs and activity meters. In some embodiments, the process controller 112 can also couple to a centralized session and/or management controller 150 for exchanging various data related to the user and the activities of the user during game play of a delayed wager interleaved wagering system.

In many embodiments, one or more users can be engaged in using the interactive application 143 executed by the interactive processing device 120. In various embodiments, a delayed wager interleaved wagering system can include an interactive application 143 that provides a skill-based interactive application that includes head-to-head play between a single user and a computing device, between two or more users against one another, or multiple users playing against a computer device and/or each other. In some embodiments, the interactive application 143 can be a skill-based interactive application where the user is not skillfully playing against the computer or any other user such as skill-based interactive applications where the user is effectively skillfully playing against himself or herself.

In some embodiments, the operation of the process controller 112 does not affect the provision of a wagering proposition by the wager server 102 except for user choice parameters that are allowable in accordance with the wagering proposition. Examples of user choice parameters include, but are not limited to: wager terms such as but not limited to a wager amount; speed of game play (for example, by pressing a button or pulling a handle of a slot machine); and/or agreement to wager into a bonus round.

In various embodiments, wager outcome data 130 communicated from the wager server 102 can also be used to convey a status operation of the wager server 102.

In a number of embodiments, communication of the wager execution commands 129 between the wager server 102 and the process controller 112 can further be used to communicate various wagering control factors that the wager server 102 uses as input. Examples of wagering control factors include, but are not limited to, an amount of Cr, AC, interactive elements, or objects consumed per wagering event, and/or the user's election to enter a jackpot round.

In some embodiments, the process controller 112 utilizes the wagering interface 148 to communicate certain interactive application data to the user, including but not limited to, club points, user status, control of the selection of choices, and messages which a user can find useful in order to adjust the interactive application experience or understand the wagering status of the user in accordance with the wagering proposition in the wager server 102.

In some embodiments, the process controller 112 utilizes the wagering interface 148 to communicate aspects of a wagering proposition to the user including, but not limited to, odds of certain wager outcomes, amount of Cr, AC, interactive elements, or objects in play, and amounts of Cr, AC, interactive elements, or objects available.

In a number of embodiments, the wager server 102 can accept wager proposition factors from the process controller 112, including, but not limited to, modifications in the amount of Cr, AC, interactive elements, or objects wagered on each individual wagering event, a number of wagering events per minute the wager server 102 can resolve, entrance into a bonus round, and other factors. An example of a varying wager amount that the user can choose can include, but is not limited to, using a more difficult interactive application level associated with an amount of a wager. These factors can increase or decrease an amount wagered per individual wagering proposition in the same manner that a standard slot machine user can decide to wager more or less credits for each pull of the handle. In several embodiments, the wager server 102 can communicate a number of factors back and forth to the process controller 112, via an interface, such that an increase/decrease in a wagered amount can be related to the change in user profile of the user in the interactive application. In this manner, a user can control a wager amount per wagering event in accordance with the wagering proposition with the change mapping to a parameter or component that is applicable to the interactive application experience.

In some embodiments, a session/management server 150 is used to regulate a delayed wager interleaved wagering system session. In such embodiments, the session/management server 150 utilizes an interface 167 to communicate with process controller 112 via an interface 165. The process controller 112 communicates outgoing session data 152 to the session/management server by encoding the session data into a signal that is transmitted to the session/management server. The session/management server receives the signal and decodes the signal to obtain the session data.

In many embodiments, the session data 152, that may include, but is not limited to, user, interactive processing device, process controller and wager server data from the process controller 112. The session/management server 150 uses the user, interactive processing device, process controller and wager server data to regulate a delayed wager interleaved wagering system session.

In some embodiments, the session/management server 150 may also assert control of a delayed wager interleaved wagering system session by communicating session control data 154 to the process controller. The session/management server 150 communicates outgoing session control data 154 to the process controller 112 by encoding the session control data into a signal that is transmitted to the process controller 112. The process controller 112 receives the signal and decodes the signal to obtain the session control data. Such control may include, but is not limited to, commanding the process controller 112 to end a delayed wager interleaved wagering system session, initiating wagering in a delayed wager interleaved wagering system session, ending wagering in a delayed wager interleaved wagering system session but not ending a user's use of the interactive application portion of the delayed wager interleaved wagering system, and changing from real credit wagering in a delayed wager interleaved wagering system to virtual credit wagering, or vice versa.

In many embodiments, the session/management server 150 manages user profiles for a plurality of users. The session/management server 150 stores and manages data about users in order to provide authentication and authorization of users of the delayed wager interleaved wagering system 128. In some embodiments, the session/management server 150 also manages geolocation information to ensure that the delayed wager interleaved wagering system i128 is only used by users in jurisdictions were gaming is approved. In various embodiments, the session/management server 150 stores application credits that are associated with the user's use of the interactive application of the delayed wager interleaved wagering system 128.

In some embodiments, the session/management server 150 communicates user and session management data 155 to the user using a management user interface 157 of the interactive processing device. The user 140 interacts with the management user interface 157 and the management user interface generates management telemetry data 159 that is communicated to the session/management server 150.

In some embodiments, the wager server 102 communicates wager session data 153 to the session/management server 150 using interfaces 169 and 171. To do so, the wager server 102 encodes wager session data into a signal that is transmitted to the session/management server 150. The session/management server 150 receives the signal and decodes the signal to obtain the wager session data.

In various embodiments, the session/management server communicates wager session control data 151 to the wager server 102 using interfaces 171 and 169. To do so, the session/management server 150 encodes wager session control data into a signal that is transmitted to the wager server 102. The wager server 102 receives the signal and decodes the signal to obtain the wager session control data.

In some embodiments, a process controller operates as an interface between an interactive processing device and a wager server. By virtue of this construction, the wager server is isolated from the interactive processing device allowing the interactive processing device to operate in an unregulated environment will allowing the wager server to operate in a regulated environment.

In some embodiments, a single wager server may provide services to two or more interactive processing devices and/or two or more process controllers, thus allowing a delayed wager interleaved wagering system to operate over a large range of scaling.

In various embodiments, multiple types of interactive processing devices using different operating systems may be interfaced to a single type of process controller and/or wager server without requiring customization of the process controller and/or the wager server.

In many embodiments, an interactive processing device may be provided as a user device under control of a user while maintaining the wager server in an environment under the control of a regulated operator of wagering equipment.

In several embodiments, data communicated between the controllers may be encrypted to increase security of the delayed wager interleaved wagering system.

In some embodiments, a process controller isolates wager logic and application logic as unregulated logic from a regulated wager server, thus allowing errors in the application logic and/or wager logic to be corrected, new application logic and/or wager logic to be used, or modifications to be made to the application logic and/or wager logic without a need for regulatory approval.

In various embodiments, an interactive application may require extensive processing resources from an interactive processing device leaving few processing resources for the functions performed by a process controller and/or a wager server. By virtue of the architecture described herein, processing loads may be distributed across multiple devices such that operations of the interactive processing device may be dedicated to the interactive application and the processes of the process controller and/or wager server are not burdened by the requirements of the interactive application.

In many embodiments, a delayed wager interleaved wagering system operates with its components being distributed across multiple devices. These devices can be connected by communication channels including, but not limited to, local area networks, wide area networks, local communication buses, and/or the like. The devices may communicate using various types of protocols, including but not limited to, networking protocols, device-to-device communications protocols, and the like.

In some embodiments, one or more components of a delayed wager interleaved wagering system are distributed in close proximity to each other and communicate using a local area network and/or a communication bus. In several embodiments, an interactive processing device and a process controller of a delayed wager interleaved wagering system are in a common location and communicate with an external wager server. In some embodiments, a process controller and a wager server of a delayed wager interleaved wagering system are in a common location and communicate with an external interactive processing device. In many embodiments, an interactive processing device, a process controller, and a wager server of a delayed wager interleaved wagering system are located in a common location. In some embodiments, a session/management server is located in a common location with a process controller and/or a wager server.

In various embodiments, these multiple devices can be constructed from or configured using a single device or a plurality of devices such that a delayed wager interleaved wagering system is executed as a system in a virtualized space such as, but not limited to, where a wager server and a process controller are large scale centralized servers in the cloud operatively connected to widely distributed interactive processing devices via a wide area network such as the Internet or a local area network. In such embodiments, the components of a delayed wager interleaved wagering system may communicate using a networking protocol or other type of device-to-device communications protocol.

In many embodiments, a centralized wager server is operatively connected to, and communicates with, one or more process controllers using a communication link. The centralized wager server can generate wager outcomes for wagers in accordance with one or more wagering propositions. The centralized wager server can execute a number of simultaneous or pseudo-simultaneous wagers in order to generate wager outcomes for a variety of wagering propositions that one or more distributed delayed wager interleaved wagering systems can use.

In several embodiments, a centralized process controller is operatively connected to one or more interactive processing devices and one or more wager servers using a communication link. The centralized process controller can perform the functionality of a process controller across various delayed wager interleaved wagering systems.

In numerous embodiments, an interactive application server provides a host for managing head-to-head play operating over a network of interactive processing devices connected to the interactive application server using a communication link. The interactive application server provides an environment where users can compete directly with one another and interact with other users.

Figure 1B:
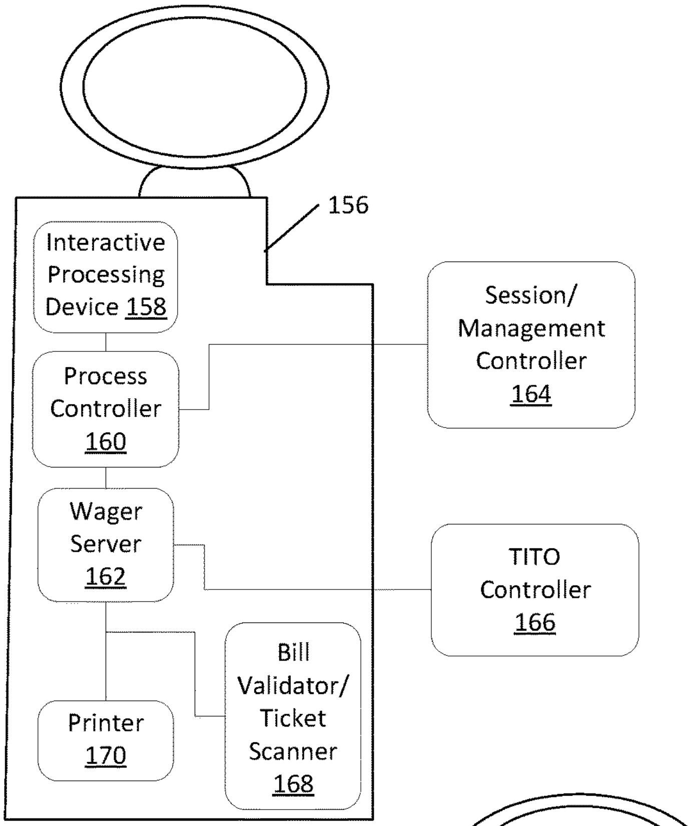
FIG. 1B is a diagram of a land-based configuration of a delayed wager interleaved wagering system in accordance with various embodiments of the invention.

FIG. 1B is a diagram of a land-based configuration of a delayed wager interleaved wagering system in accordance with various embodiments of the invention. A land-based configuration of a delayed wager interleaved wagering system 156 includes an interactive processing device 158, a process controller 160 and a wager server 162 housed in a common enclosure. In many embodiments, the process controller 160 is operatively connected to an external session/management controller 164. In various embodiments, the wager server 162 is operatively connected to a ticket-in-ticket-out (TITO) controller 166 or other type of credit controller. The wager server 162 communicates with the TITO controller 166 to obtain amounts of credits used for wagering. In operation, the wager server 162 uses a bill validator/ticket scanner 168 to scan a TITO ticket having indicia of credit account data of a credit account of the TITO controller 166. The wager server 162 communicates the credit account data to the TITO controller 166. The TITO controller 166 uses the credit account data to determine an amount of credits to transfer to the wager server 162. The TITO controller 166 communicates the amount of credits to the wager server 162. The wager server 162 credits the one or more credit meters with the amount of credits so that the credits can be used when a user makes wagers using the delayed wager interleaved wagering system 156. In addition, the wager server 162 can use the TITO controller 166 along with a ticket printer 170 to generate a TITO ticket for a user. In operation, the wager server 162 communicates an amount of credits for a credit account on the TITO controller 166. The TITO controller 166 receives the amount of credits and creates the credit account and credits the credit account with the amount of credits. The TITO controller 166 generates credit account data for the credit account and communicates the credit account data to the wager server 162. The wager server 162 uses the ticket printer 170 to print indicia of the credit account data onto a TITO ticket.

Figure 1C:
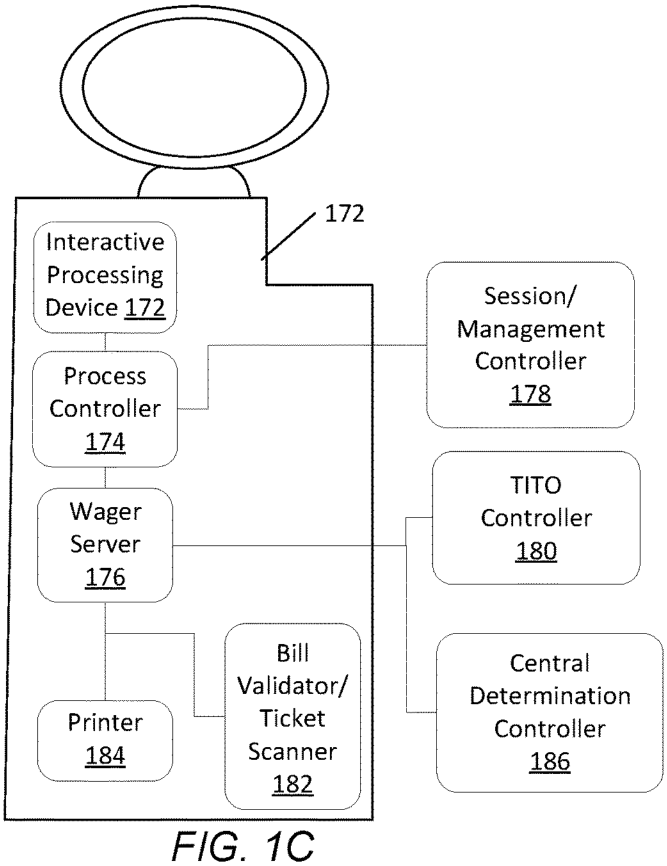
FIG. 1C is another diagram of a land-based configuration of a delayed wager interleaved wagering system in accordance with various embodiments of the invention.

FIG. 1C is a diagram of another land-based configuration of a delayed wager interleaved wagering system in accordance with various embodiments of the invention. A land-based configuration of a delayed wager interleaved wagering system 172 includes an interactive processing device 172, a process controller 174 and a wager server 176 housed in a common enclosure. The process controller 174 is operatively connected to an external session/management controller 178. The wager server 176 is operatively connected to a ticket-in-ticket-out (TITO) controller 180 or other type of credit controller. The wager server 176 communicates with the TITO controller 180 to obtain amounts of credits used for wagering. In operation, the wager server 176 uses a bill validator/ticket scanner 182 to scan a TITO ticket having indicia of credit account data of a credit account of the TITO controller 180. The wager server 176 communicates the credit account data to the TITO controller 180. The TITO controller 180 uses the credit account data to determine an amount of credits to transfer to the wager server 176. The TITO controller 180 communicates the amount of credits to the wager server 176. The wager server 176 receives the amount of credits and credits the one or more credit meters with the amount of credits so that the credits can be used when a user makes wagers using the delayed wager interleaved wagering system 172. In addition, the wager server 176 can use the TITO controller 180 along with a ticket printer 184 to generate a TITO ticket for a user. In operation, the wager server 176 communicates an amount of credits for a credit account on the TITO controller 180. The TITO controller 180 receives the amount of credits and creates the credit account and credits the credit account with the amount of credits. The TITO controller 180 generates credit account data for the credit account and communicates the credit account data to the wager server 176. The wager server 176 uses the ticket printer 184 to print indicia of the credit account data onto a TITO ticket.

The wager server 176 is operatively connected to a central determination controller 186. In operation, when the wager server 176 needs to determine a wager outcome, the wager server communicates a request to the central determination controller 186 for the wager outcome. The central determination controller 186 receives the wager outcome request and generates a wager outcome in response to the wager request. The central determination controller 186 communicates the wager outcome to the wager server 176. The wager server 176 receives the wager outcome and utilizes the wager outcome as described herein. In some embodiments, the wager outcome is drawn from a pool of pre-determined wager outcomes. In some embodiments, the wager outcome is a pseudo random result or random result that is utilized by the wager server along with paytables to determine a wager outcome as described herein.

Figure 1D:
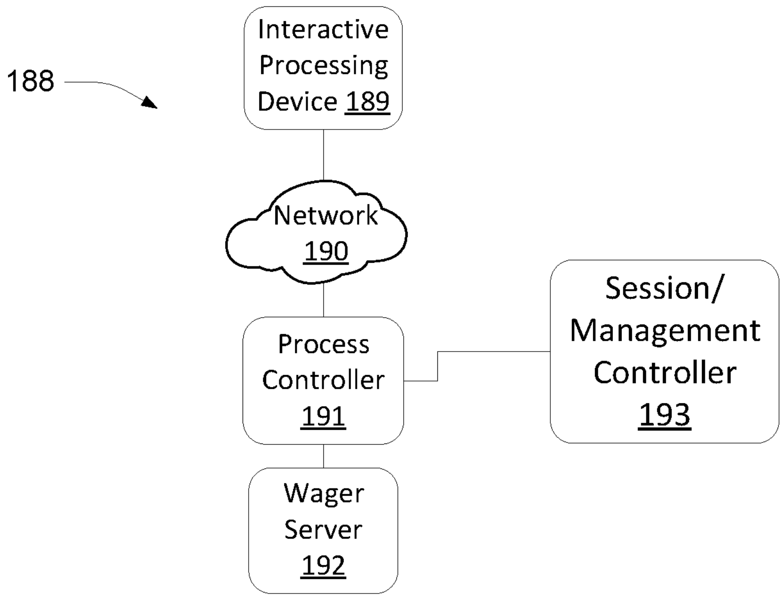
FIG. 1D is a diagram of a network configuration of a delayed wager interleaved wagering system in accordance with various embodiments of the invention.

FIG. 1D is a diagram of an interactive configuration of a delayed wager interleaved wagering system in accordance with various embodiments of the invention. An interactive configuration of a delayed wager interleaved wagering system is useful for deployment over a wide area network such as an internet. An interactive configuration of a delayed wager interleaved wagering system 188 includes an interactive processing device 189 operatively connected by a network 190 to a process controller 191, and a wager server 192. The process controller 191 is operatively connected to a session/management controller 193.

Figure 1E:
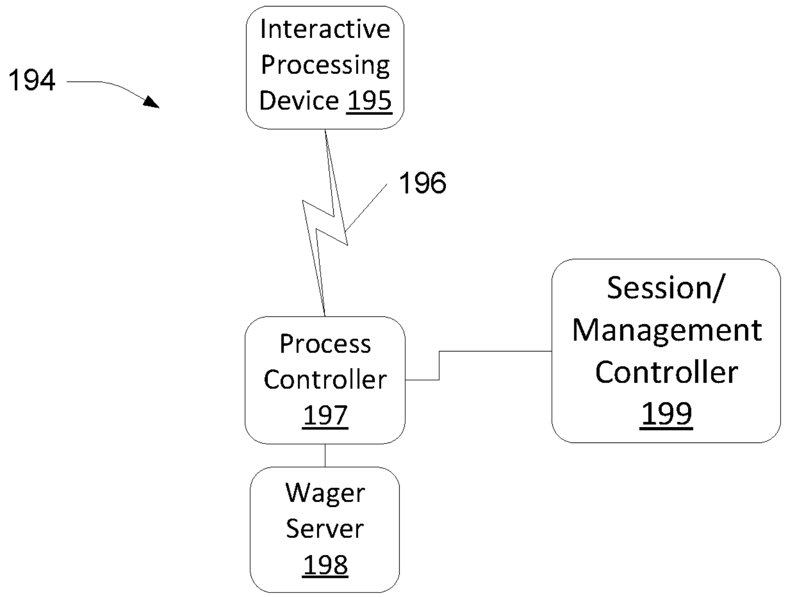
FIG. 1E is a diagram of a mobile configuration of a delayed wager interleaved wagering system in accordance with various embodiments of the invention.

FIG. 1E is a diagram of a mobile configuration of a delayed wager interleaved wagering system in accordance with various embodiments of the invention. A mobile configuration of a delayed wager interleaved wagering system is useful for deployment over wireless communication network, such as a wireless local area network or a wireless telecommunications network. An interactive configuration of a delayed wager interleaved wagering system 194 includes an interactive processing device 195 operatively connected by a wireless network 196 to a process controller 197, and a wager server 198. The process controller 197 is also operatively connected to a session/management controller 199.

FIGS. 2A, 2B, 2C, and 2D are illustrations of interactive processing devices of a delayed wager interleaved wagering system in accordance with various embodiments of the invention. An interactive processing device, such as interactive processing device 120 of FIG. 1A, may be constructed from or configured using one or more processing devices configured to perform the operations of the interactive processing device. An interactive processing device in a delayed wager interleaved wagering system may be constructed from or configured using any processing device having sufficient processing and communication capabilities that may be configured to perform the processes of an interactive processing device in accordance with various embodiments of the invention. In some embodiments, the construction or configuration of the interactive processing device may be achieved through the use of an application control interface, such as application control interface 131 of FIG. 1A, and/or through the use of an interactive application, such as interactive application 143 of FIG. 1A.

Figure 2A:
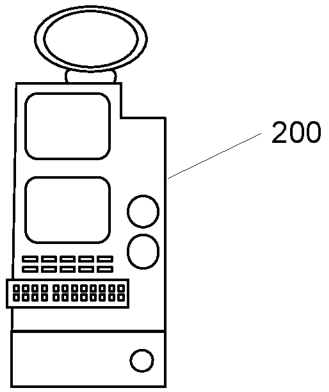
FIGS. 2A, 2B, 2C, and 2D are illustrations of interactive processing devices of a delayed wager interleaved wagering system in accordance with various embodiments of the invention.

In some embodiments, an interactive processing device may be constructed from or configured using an electronic gaming machine 200 as shown in FIG. 2A. The electronic gaming machine 200 may be physically located in various types of gaming establishments.

Figure 2B:
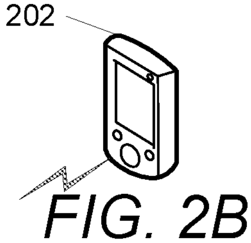

In many embodiments, an interactive processing device may be constructed from or configured using a portable device 202 as shown in FIG. 2B. The portable device 202 is a device that may wirelessly connect to a network. Examples of portable devices include, but are not limited to, a tablet computer, a personal digital assistant, and a smartphone.

Figure 2C:
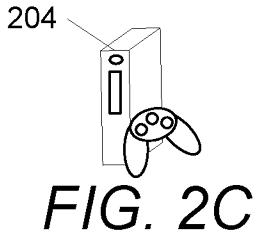

In some embodiments, an interactive processing device may be constructed from or configured using a gaming console 204 as shown in FIG. 2C.

Figure 2D:
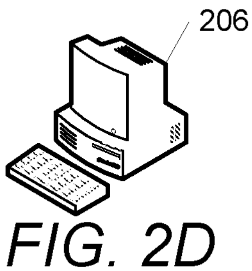

In various embodiments, an interactive processing device may be constructed from or configured using a personal computer 206 as shown in FIG. 2D.

In some embodiments, a device, such as the devices of FIGS. 2A, 2B, 2C, and 2D, may be used to construct a complete delayed wager interleaved wagering system and may be operatively connected using a communication link to a session and/or management controller, such as session and/or management controller 150 of FIG. 1A.

Figure 3A:
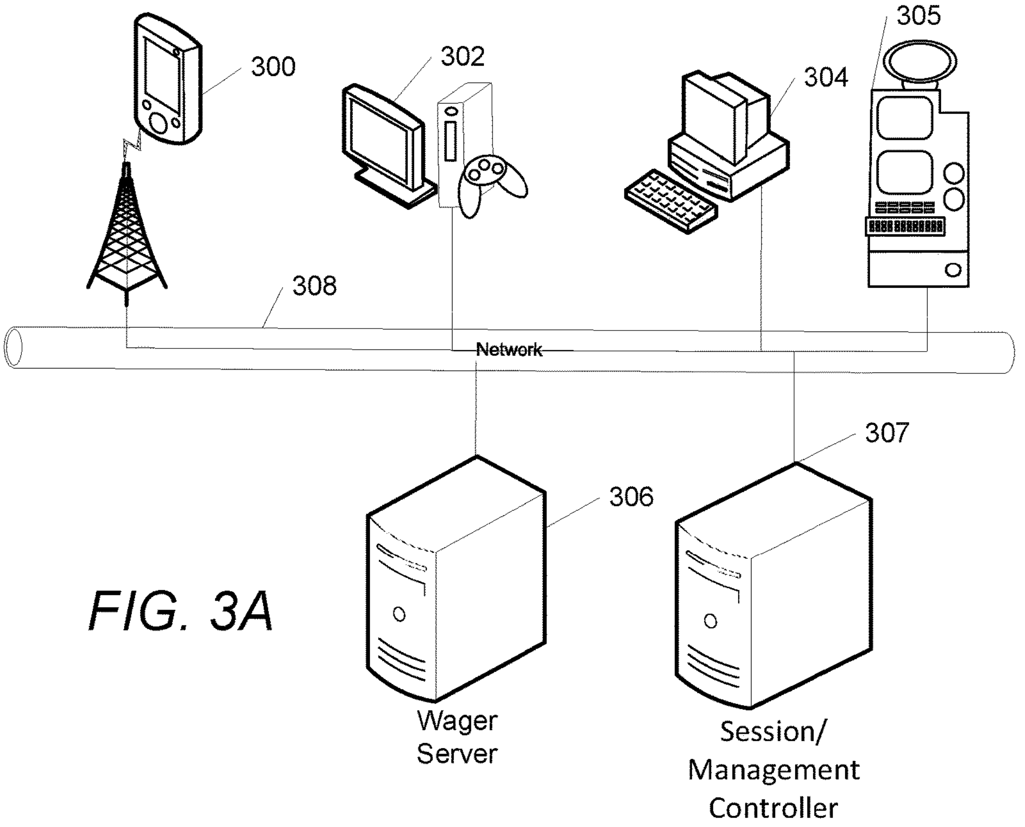
FIGS. 3A, 3B and 3C are diagrams of distributed delayed wager interleaved wagering systems in accordance with various embodiments of the invention.
Figure 3B:
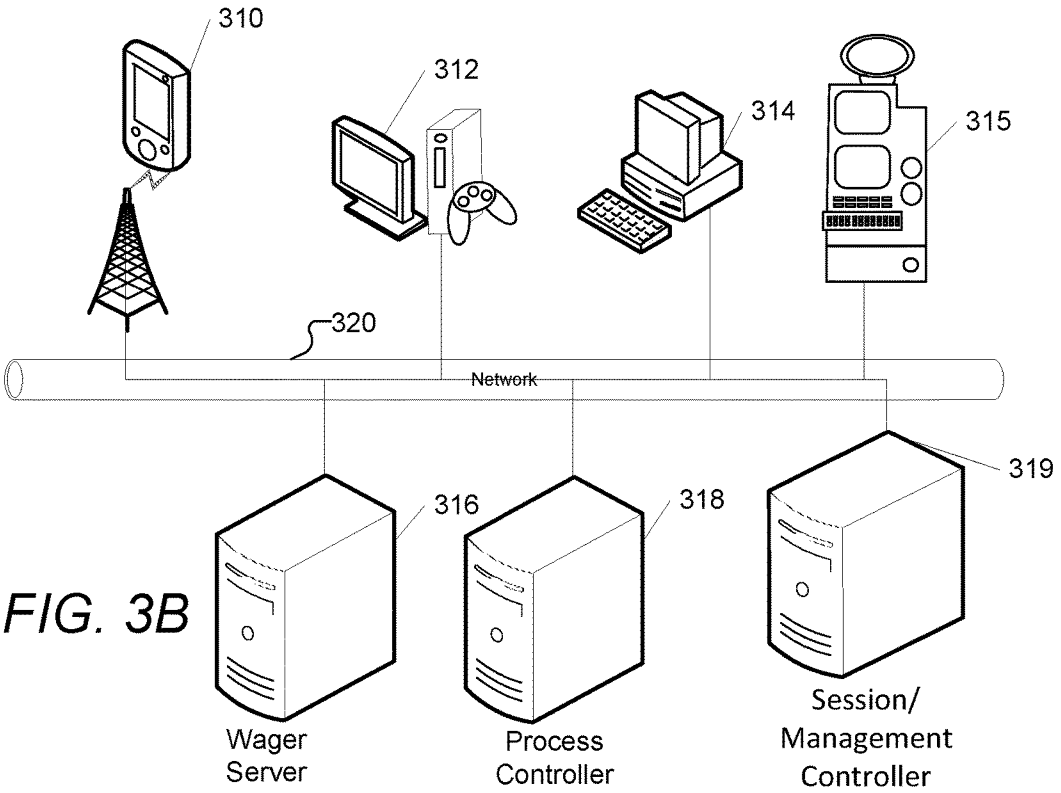
Figure 3C:
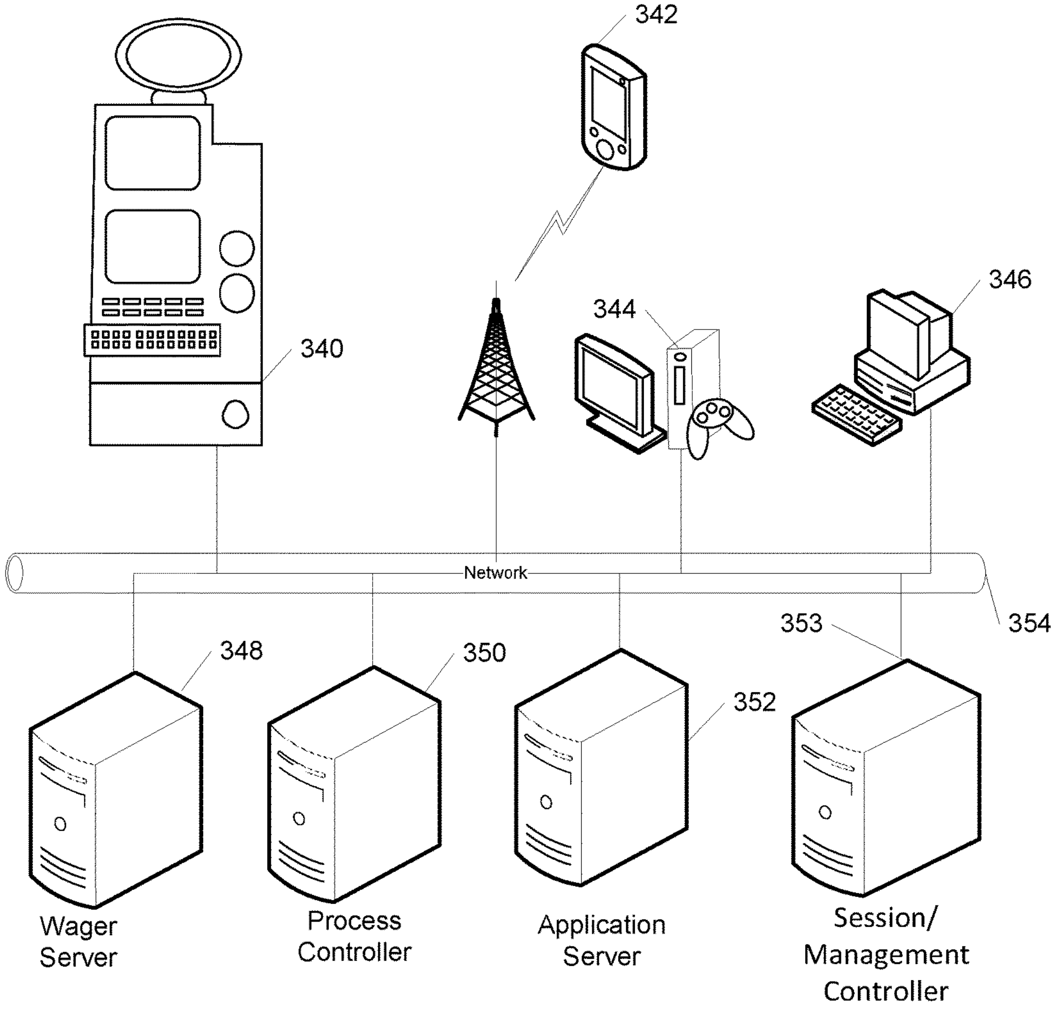

Some delayed wager interleaved wagering systems in accordance with many embodiments of the invention can be distributed across a plurality of devices in various configurations. FIGS. 3A, 3B and 3C are diagrams of distributed delayed wager interleaved wagering systems in accordance with various embodiments of the invention. Turning now to FIG. 3A, one or more interactive processing devices of a distributed delayed wager interleaved wagering system, such as but not limited to, a mobile or wireless device 300, a gaming console 302, a personal computer 304, and an electronic gaming machine 305, are operatively connected with a wager server 306 of a distributed delayed wager interleaved wagering system using a communication link 308. Communication link 308 is a communications link that allows processing systems to communicate with each other and to share data. Examples of the communication link 308 can include, but are not limited to: a wired or wireless interdevice communication link, a serial or parallel interdevice communication bus; a wired or wireless network such as a Local Area Network (LAN), a Wide Area Network (WAN), or the link; or a wired or wireless communication network such as a wireless telecommunications network or plain old telephone system (POTS). In some embodiments, one or more processes of an interactive processing device and a process controller as described herein are executed on the individual interactive processing devices 300, 302, 304 and 305 while one or more processes of a wager server as described herein can be executed by the wager server 306.

In many embodiments, a distributed delayed wager interleaved wagering system and may be operatively connected using a communication link to a session and/or management controller 307, that performs the processes of a session and/or management controller as described herein.

A distributed delayed wager interleaved wagering system in accordance with another embodiment of the invention is illustrated in FIG. 3B. As illustrated, one or more interactive processing devices of a distributed delayed wager interleaved wagering system, such as but not limited to, a mobile or wireless device 310, a gaming console 312, a personal computer 314, and an electronic gaming machine 315, are operatively connected with a wager server 316 and a process controller 318 over a communication link 320. Communication link 320 is a communication link that allows processing systems to communicate and share data. Examples of the communication link 320 can include, but are not limited to: a wired or wireless interdevice communication link, a serial or parallel interdevice communication bus; a wired or wireless network such as a Local Area Network (LAN), a Wide Area Network (WAN), or the link; or a wired or wireless communication network such as a wireless telecommunications network or plain old telephone system (POTS). In some embodiments, the processes of an interactive processing device as described herein are executed on the individual interactive processing devices 310, 312, 314 and 315. One or more processes of a wager server as described herein are executed by the wager server 316, and one or more processes of a process controller as described herein are executed by the process controller 318.

In many embodiments, a distributed delayed wager interleaved wagering system and may be operatively connected using a communication link to a session and/or management controller 319, that performs the processes of a session and/or management controller as described herein.

A distributed delayed wager interleaved wagering systems in accordance with still another embodiment of the invention is illustrated in FIG. 3C. As illustrated, one or more interactive processing devices of a distributed delayed wager interleaved wagering system, such as but not limited to, a mobile device 342, a gaming console 344, a personal computer 346, and an electronic gaming machine 340 are operatively connected with a wager server 348 and a process controller 350, and an interactive application server 352 using a communication link 354. Communication link 354 is a communications link that allows processing systems to communicate and to share data. Examples of the communication link 354 can include, but are not limited to: a wired or wireless interdevice communication link, a serial or parallel interdevice communication bus; a wired or wireless network such as a Local Area Network (LAN), a Wide Area Network (WAN), or the link; or a wired or wireless communication network such as a wireless telecommunications network or plain old telephone system (POTS). In some embodiments, one or more processes of a display and user interface of an interactive processing device as described herein are executed on the individual interactive processing devices 340, 342, 344 and 346. One or more processes of a wager server as described herein can be executed by the wager server 348. One or more processes of a process controller as described herein can be executed by the process controller server 350 and one or more processes of an interactive processing device excluding the display and user interfaces can be executed by the interactive application server 352.

In many embodiments, a distributed delayed wager interleaved wagering system and may be operatively connected using a communication link to a session and/or management controller 353, that performs the processes of a session and/or management controller as described herein.

In various embodiments, a session/management server may be operatively connected to components of a delayed wager interleaved wagering system using a communication link. In other embodiments, a number of other peripheral systems, such as a user management system, a gaming establishment management system, a regulatory system, and/or hosting servers are also operatively connected with the delayed wager interleaved wagering systems using a communication link. Also, other servers can reside outside the bounds of a network within a firewall of the operator to provide additional services for network connected delayed wager interleaved wagering systems.

Although various distributed delayed wager interleaved wagering systems are described herein, delayed wager interleaved wagering systems can be distributed in any configuration as appropriate to the specification of a specific application in accordance with embodiments of the invention. In some embodiments, components of a distributed delayed wager interleaved wagering system, such as a process controller, wager server, interactive processing device, or other servers that perform services for a process controller, wager server and/or interactive processing device, can be distributed in different configurations for a specific distributed delayed wager interleaved wagering system application.

Figure 4A:
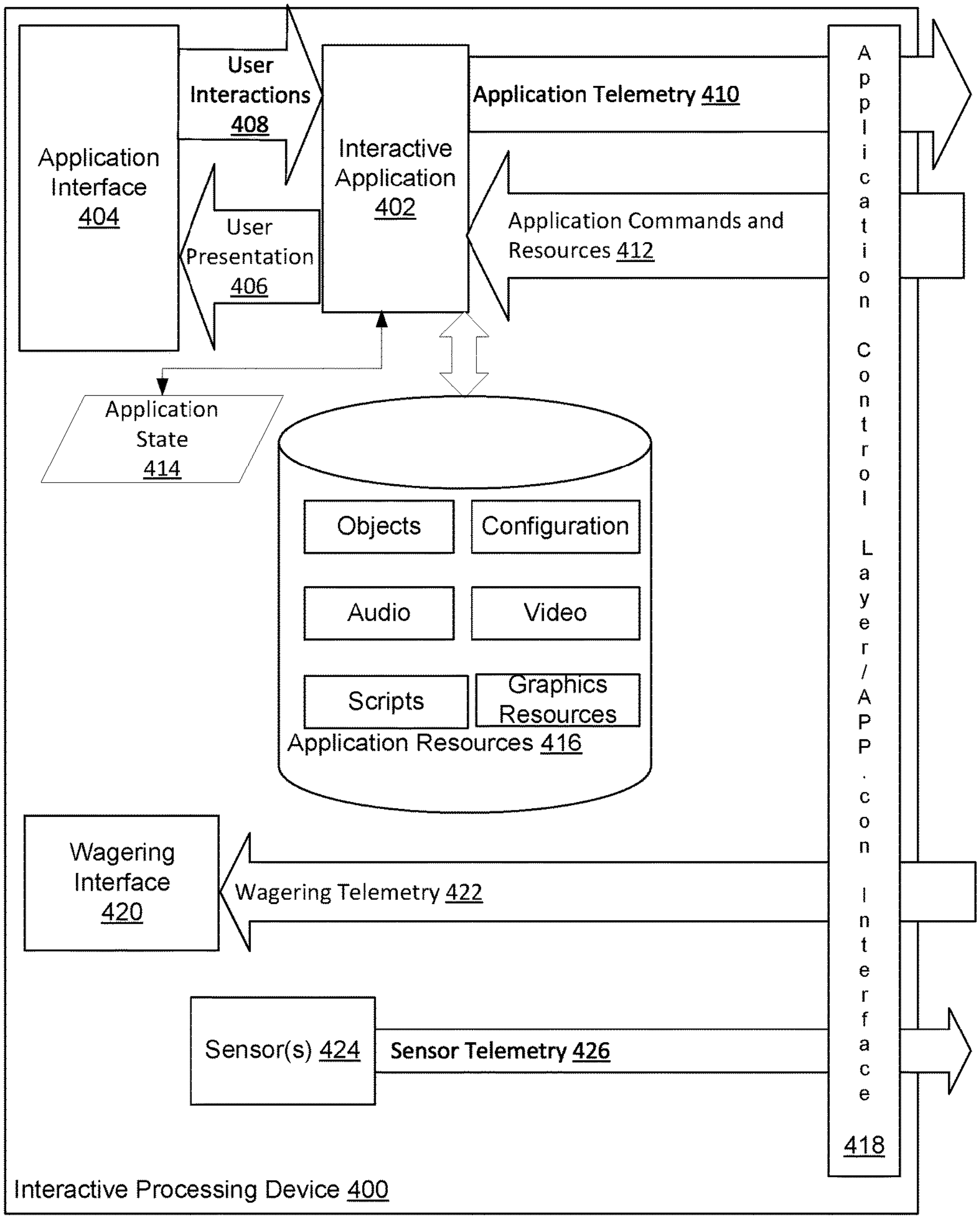
FIGS. 4A and 4B are diagrams of a structure of an interactive processing device of a delayed wager interleaved wagering system in accordance with various embodiments of the invention.
Figure 4B:
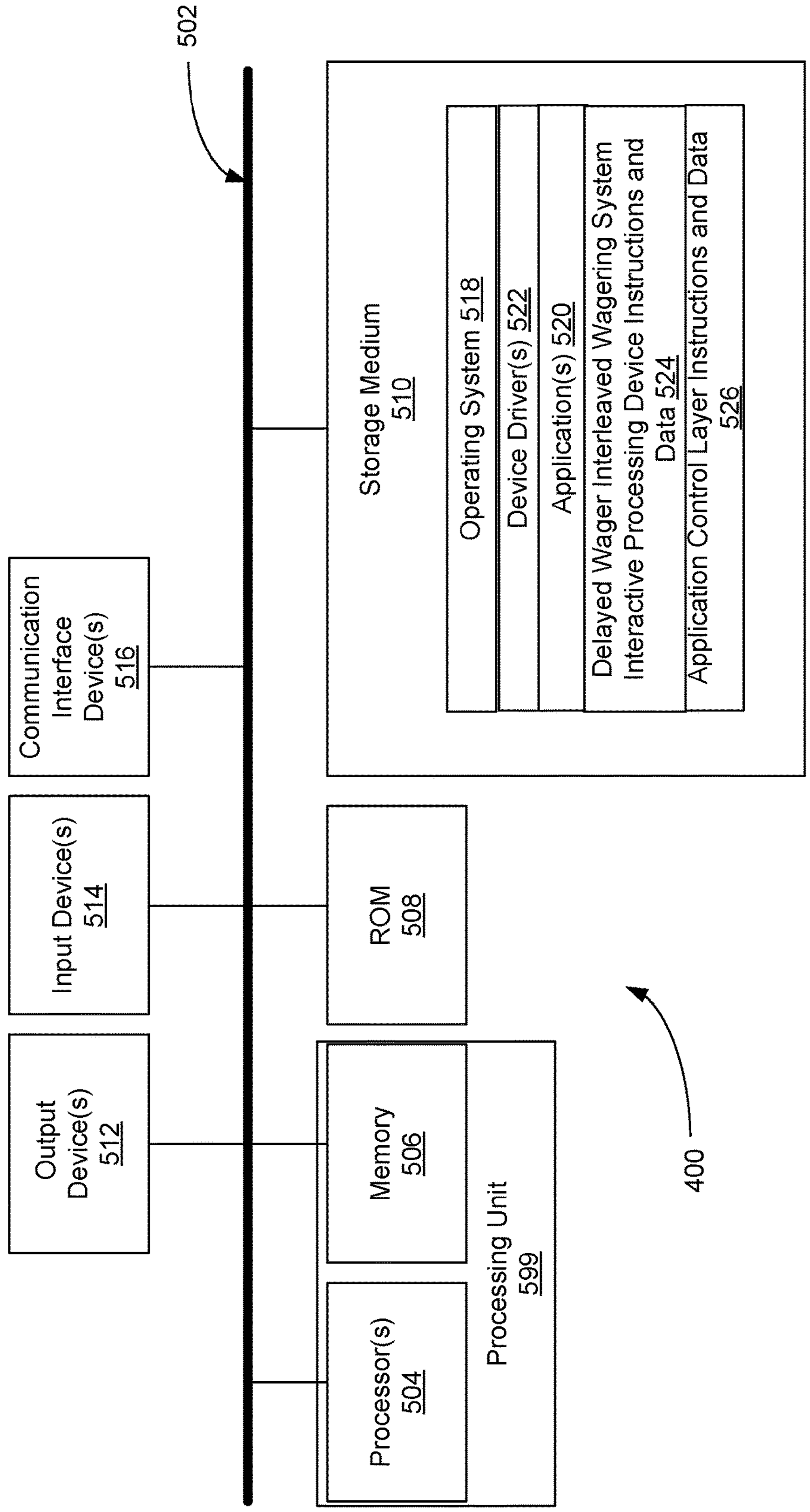

FIGS. 4A and 4B are diagrams of a structure of an interactive processing device of a delayed wager interleaved wagering system in accordance with various embodiments of the invention. An interactive processing device may be constructed from or configured using one or more processing devices configured to perform the operations of the interactive processing device. In many embodiments, an interactive processing device can be constructed from or configured using various types of processing devices including, but not limited to, a mobile device such as a smartphone or the like, a personal digital assistant, a wireless device such as a tablet computer or the like, an electronic gaming machine, a personal computer, a gaming console, a set-top box, a computing device, a controller, or the like.

Referring now to FIG. 4A, an interactive processing device 400, suitable for use as interactive processing device 120 of FIG. 1A, provides an execution environment for an interactive application 402 of a delayed wager interleaved wagering system. In several embodiments, an interactive processing device 400 of a delayed wager interleaved wagering system provides an interactive application 402 that generates an application interface 404 for interaction with by a user. The interactive application 402 generates a user presentation 406 that is presented to the user through the application interface 404. The user presentation 406 may include audio features, visual features or tactile features, or any combination of these features. The application interface 404 further includes one or more human input devices (HIDs) interfaces that communicate with one or more HIDs (e.g., the input devices 514 of FIG. 4*b*) that the user can use to interact with the delayed wager interleaved wagering system. The user's interactions 408 are included by the interactive application 402 in application telemetry data 410 that is communicated by interactive processing device 400 to various other components of a delayed wager interleaved wagering system as described herein. The interactive application 402 receives application commands and resources 412 communicated from various other components of a delayed wager interleaved wagering system as described herein.

In some embodiments, various components of the interactive application 402 can read data from an application state 414 in order to provide one or more features of the interactive application. In various embodiments, components of the interactive application 402 can include, but are not limited to, a physics engine, a rules engine, and/or a graphics engine. The physics engine is used to simulate physical interactions between virtual objects in the interactive application 402. The rules engine implements the rules of the interactive application and a P/RNG that may be used for influencing or determining certain variables and/or outcomes to provide a randomizing influence on the operations of the interactive application. The graphics engine is used to generate a visual representation of the interactive application state to the user. Furthermore, the components may also include an audio engine to generate audio outputs for the user interface.

During operation, the interactive application reads and writes application resources 416 stored on a data store of the interactive processing device host. The application resources 416 may include objects having graphics and/or control logic used to provide application environment objects of the interactive application. In various embodiments, the resources may also include, but are not limited to, video files that are used to generate a portion of the user presentation 406; audio files used to generate music, sound effects, etc. within the interactive application; configuration files used to configure the features of the interactive application; scripts or other types of control code used to provide various features of the interactive application; and graphics resources such as textures, objects, etc. that are used by a graphics engine to render objects displayed in an interactive application.

In operation, components of the interactive application 402 read portions of the application state 414 and generate the user presentation 406 for the user that is presented to the user using the user interface 404. The user perceives the user presentation and provides user interactions 408 using the HIDs. The corresponding user interactions are received as user actions or inputs by various components of the interactive application 402. The interactive application 402 translates the user actions into interactions with the virtual objects of the application environment stored in the application state 414. Components of the interactive application use the user interactions with the virtual objects of the interactive application and the interactive application state 414 to update the application state 414 and update the user presentation 406 presented to the user. The process loops continuously while the user interacts with the interactive application of the delayed wager interleaved wagering system.

The interactive processing device 400 provides one or more interfaces 418 between the interactive processing device 400 and other components of a delayed wager interleaved wagering system, such as, but not limited to, a process controller. The interactive processing device 400 and the other delayed wager interleaved wagering system components communicate with each other using the interfaces. The interface may be used to pass various types of data, and to communicate and receive messages, status data, commands and the like. In certain embodiments, the interactive processing device 400 and a process controller communicate application commands and environment resources 412 and application telemetry data 410. In some embodiments, the communications include requests by the process controller that the interactive processing device 400 update the application state 414 using data provided by the process controller.

In many embodiments, a communication by a process controller includes a request that the interactive processing device 400 update one or more resources 416 using data provided by the process controller. In a number of embodiments, the interactive processing device 400 provides all or a portion of the application state to the process controller. In some embodiments, the interactive processing device 400 may also provide data about one or more of the application resources 416 to the process controller. In some embodiments, the communication includes user interactions that the interactive processing device 400 communicates to the process controller. The user interactions may be low level user interactions with the user interface 404, such as manipulation of a HID, or may be high level interactions with game objects as determined by the interactive application. The user interactions may also include resultant actions such as modifications to the application state 414 or game resources 416 resulting from the user's interactions taken in the delayed wager interleaved wagering system interactive application. In some embodiments, user interactions include, but are not limited to, actions taken by entities such as non-user characters (NPC) of the interactive application that act on behalf of or under the control of the user.

In some embodiments, the interactive processing device 400 includes a wagering interface 420 used to communicate delayed wager interleaved wagering system telemetry data 422 to and from the user. The delayed wager interleaved wagering system telemetry data 422 from the delayed wager interleaved wagering system include, but are not limited to, data used by the user to configure Cr, AC and interactive element wagers, and data about the wagering proposition Cr, AC and interactive element wagers such as, but not limited to, Cr, AC and interactive element balances and Cr, AC and interactive element amounts wagered.

In some embodiments, the interactive processing device includes one or more sensors 424. Such sensors may include, but are not limited to, physiological sensors that monitor the physiology of the user, environmental sensors that monitor the physical environment of the interactive processing device, accelerometers that monitor changes in motion of the interactive processing device, and location sensors that monitor the location of the interactive processing device such as global positioning sensors (GPSs). The interactive processing device 400 communicates sensor telemetry data 426 to one or more components of the delayed wager interleaved wagering system.

Referring now to FIG. 4B, interactive processing device 400 includes a bus 502 that provides an interface for one or more processors 504, random access memory (RAM) 506, read only memory (ROM) 508, machine-readable storage medium 510, one or more user output devices 512, one or more user input devices 514, and one or more communication interface devices 516.

The one or more processors 504 may take many forms, such as, but not limited to: a central processing unit (CPU); a multi-processor unit (MPU); an ARM processor; a controller; a programmable logic device; or the like.

In the example embodiment, the one or more processors 504 and the random access memory (RAM) 506 form an interactive processing device processing unit 599. In some embodiments, the interactive processing device processing unit includes one or more processors operatively connected to one or more of a RAM, ROM, and machine-readable storage medium; the one or more processors of the interactive processing device processing unit receive instructions stored by the one or more of a RAM, ROM, and machine-readable storage medium via a bus; and the one or more processors execute the received instructions. In some embodiments, the interactive processing device processing unit is an ASIC (Application-Specific Integrated Circuit). In some embodiments, the interactive processing device processing unit is a SoC (System-on-Chip).

Examples of output devices 512 include, but are not limited to, display screens; light panels; and/or lighted displays. In accordance with particular embodiments, the one or more processors 504 are operatively connected to audio output devices such as, but not limited to: speakers; and/or sound amplifiers. In accordance with many of these embodiments, the one or more processors 504 are operatively connected to tactile output devices like vibrators, and/or manipulators.

Examples of user input devices 514 include, but are not limited to: tactile devices including but not limited to, keyboards, keypads, foot pads, touch screens, and/or trackballs; non-contact devices such as audio input devices; motion sensors and motion capture devices that the interactive processing device can use to receive inputs from a user when the user interacts with the interactive processing device; physiological sensors that monitor the physiology of the user; environmental sensors that monitor the physical environment of the interactive processing device; accelerometers that monitor changes in motion of the interactive processing device; and location sensors that monitor the location of the interactive processing device such as global positioning sensors.

The one or more communication interface devices 516 provide one or more wired or wireless interfaces for communicating data and commands between the interactive processing device 400 and other devices that may be included in a delayed wager interleaved wagering system. Such wired and wireless interfaces include, but are not limited to: a Universal Serial Bus (USB) interface; a Bluetooth interface; a Wi-Fi interface; an Ethernet interface; a Near Field Communication (NFC) interface; a plain old telephone system (POTS) interface, a cellular or satellite telephone network interface; and the like.

The machine-readable storage medium 510 stores machine-executable instructions for various components of the interactive processing device, such as but not limited to: an operating system 518; one or more device drivers 522; one or more application programs 520 including but not limited to an interactive application; and delayed wager interleaved wagering system interactive processing device instructions and data 524 for use by the one or more processors 504 to provide the features of an interactive processing device as described herein. In some embodiments, the machine-executable instructions further include application control interface/application control interface instructions and data 526 for use by the one or more processors 504 to provide the features of an application control interface/application control interface as described herein.

In various embodiments, the machine-readable storage medium 510 is one of a (or a combination of two or more of) a hard drive, a flash drive, a DVD, a CD, a flash storage, a solid state drive, a ROM, an EIEPROM, and the like.

In operation, the machine-executable instructions are loaded into memory 506 from the machine-readable storage medium 510, the ROM 508 or any other storage location. The respective machine-executable instructions are accessed by the one or more processors 504 via the bus 502, and then executed by the one or more processors 504. Data used by the one or more processors 504 are also stored in memory 506, and the one or more processors 504 access such data during execution of the machine-executable instructions. Execution of the machine-executable instructions causes the one or more processors 504 to control the interactive processing device 400 to provide the features of a delayed wager interleaved wagering system interactive processing device as described herein Although the interactive processing device is described herein as being constructed from or configured using one or more processors and instructions stored and executed by hardware components, the interactive processing device can be constructed from or configured using only hardware components in accordance with other embodiments. In addition, although the storage medium 510 is described as being operatively connected to the one or more processors through a bus, those skilled in the art of interactive processing devices will understand that the storage medium can include removable media such as, but not limited to, a USB memory device, an optical CD ROM, magnetic media such as tape and disks. In some embodiments, the storage medium 510 can be accessed by the one or more processors 504 through one of the communication interface devices 516 or using a communication link. Furthermore, any of the user input devices or user output devices can be operatively connected to the one or more processors 504 via one of the communication interface devices 516 or using a communication link.

In some embodiments, the interactive processing device 400 can be distributed across a plurality of different devices. In many such embodiments, an interactive processing device of a delayed wager interleaved wagering system includes an interactive application server operatively connected to an interactive client using a communication link. The interactive application server and interactive application client cooperate to provide the features of an interactive processing device as described herein.

In various embodiments, the interactive processing device 400 may be used to construct other components of a delayed wager interleaved wagering system as described herein.

In some embodiments, components of an interactive processing device and a process controller of a delayed wager interleaved wagering system may be constructed from or configured using a single device using processes that communicate using an interprocess communication protocol. In other such embodiments, the components of an interactive processing device and a process controller of a delayed wager interleaved wagering system may communicate by passing messages, parameters or the like.

Figure 5A:
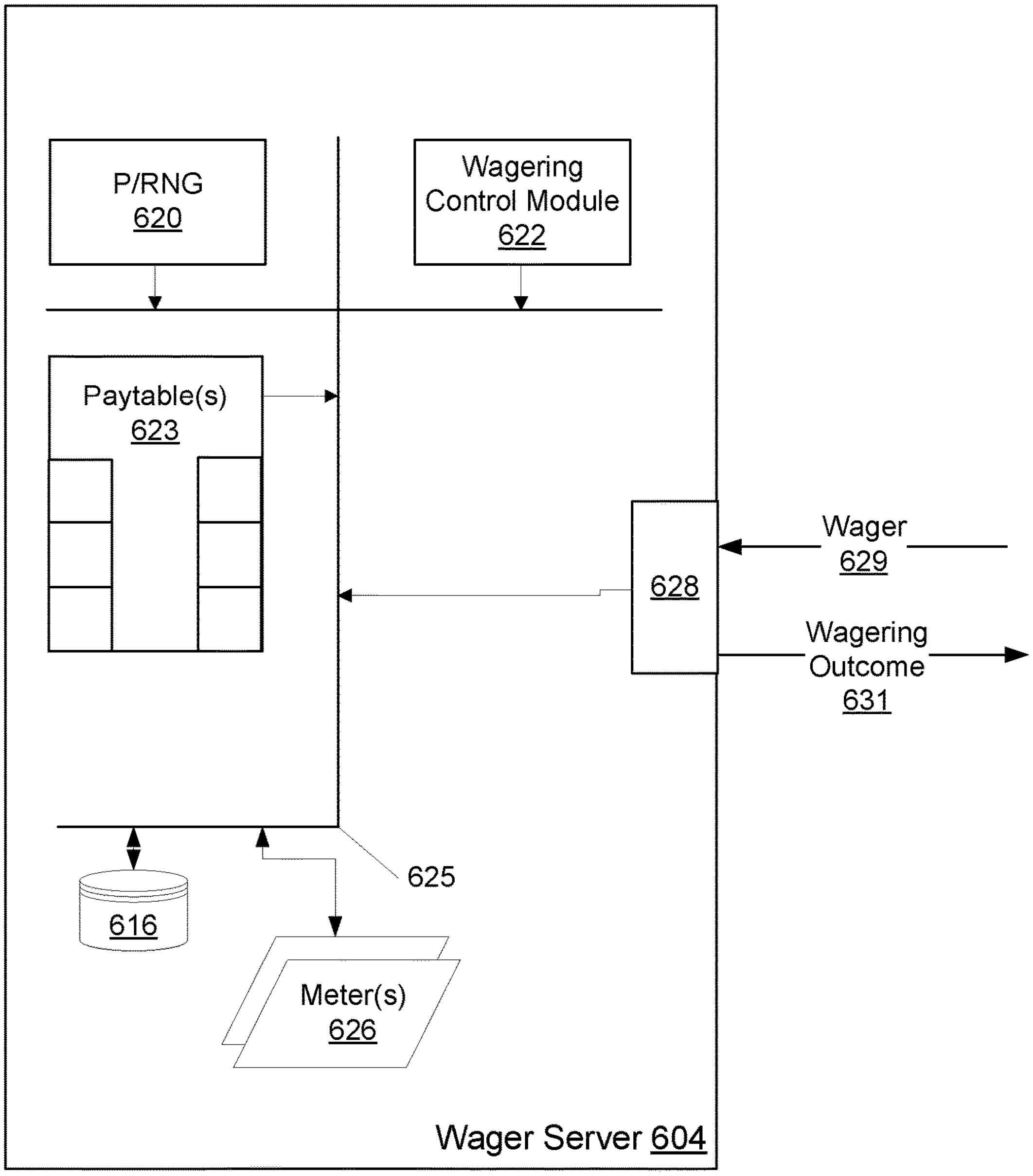
FIGS. 5A and 5B are diagrams of a structure of a wager server of a delayed wager interleaved wagering system in accordance with various embodiments of the invention.
Figure 5B:
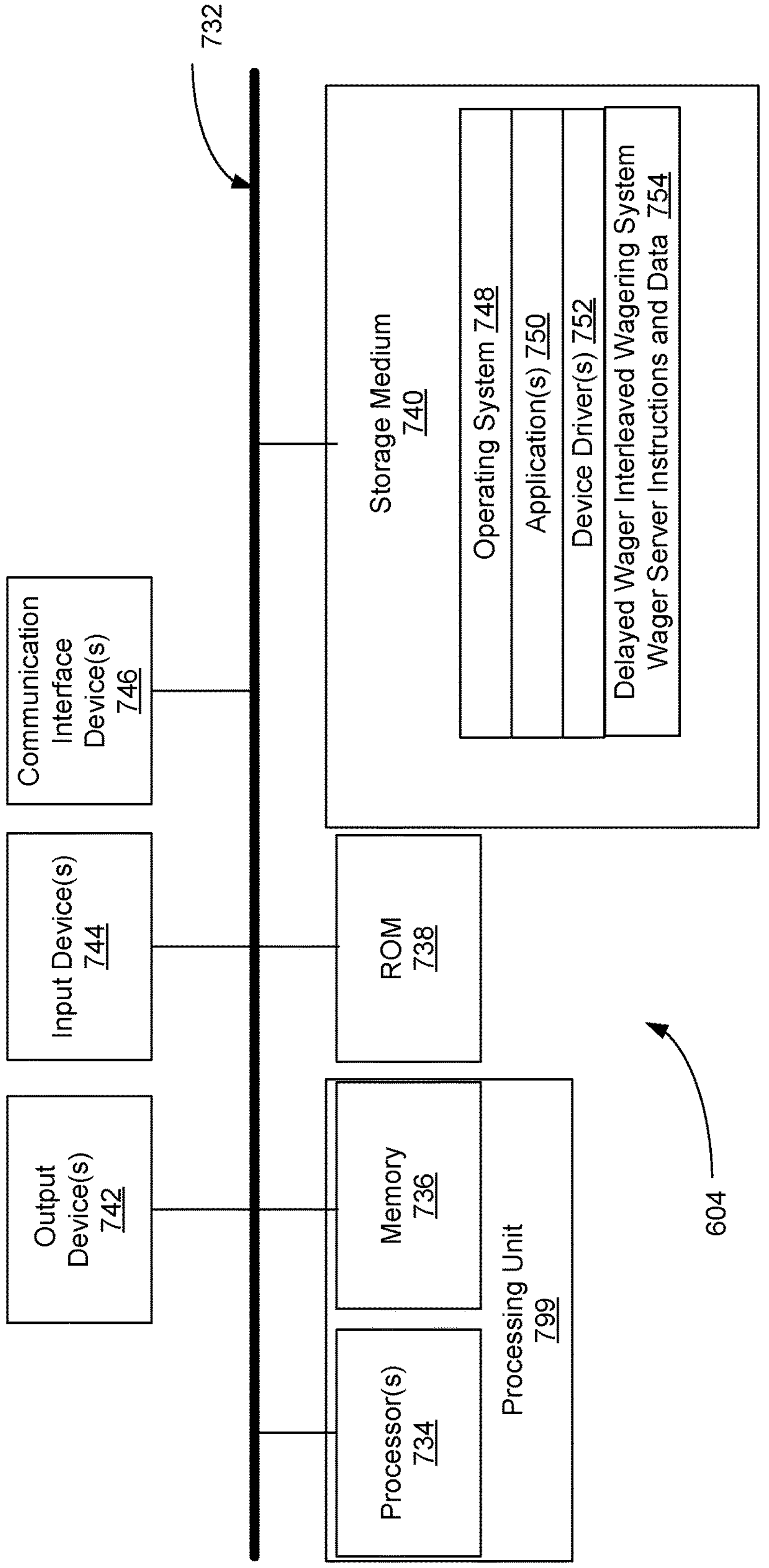

FIGS. 5A and 5B are diagrams of a structure of a wager server of a delayed wager interleaved wagering system in accordance with various embodiments of the invention. A wager server may be constructed from or configured using one or more processing devices configured to perform the operations of the wager server. In many embodiments, a wager server can be constructed from or configured using various types of processing devices including, but not limited to, a mobile device such as a smartphone or the like, a personal digital assistant, a wireless device such as a tablet computer or the like, an electronic gaming machine, a personal computer, a gaming console, a set-top box, a computing device, a controller, or the like.

Referring now to FIG. 5A, in various embodiments, a wager server 604, suitable for use as wager server 102 of FIG. 1A, includes a pseudorandom or random number generator (P/RNG) 620 to produce random results or pseudo random results; one or more paytables 623 which includes a plurality of factors indexed by the random result to be multiplied with an amount of Cr, AC, interactive elements, or objects committed in a wager; and a wagering control module 622 whose processes may include, but are not limited to, generating random results, looking up factors in the paytables, multiplying the factors by an amount of Cr, AC, interactive elements, or objects wagered, and administering one or more Cr, AC, interactive element, or object meters 626. The various wager server components can interface with each other via an internal bus 625 and/or other appropriate communication mechanism.

An interface 628 allows the wager server 604 to operatively connect to an external device, such as one or more process controllers as described herein. The interface 628 provides for communication of wager execution commands 629 from the external device that is used to specify wager parameters and/or trigger execution of a wager by the wager server 604 as described herein. The interface 628 may also provide for communicating wager outcome data 631 to an external device as described herein. In numerous embodiments, the interface between the wager server 604 and other systems/devices may be a wide area network (WAN) such as the Internet. However, other methods of communication may be used including, but not limited to, a local area network (LAN), a universal serial bus (USB) interface, and/or some other method by which two electronic devices could communicate with each other.

In various embodiments, a wager server 604 may use a P/RNG provided by an external system. The external system may be connected to the wager server 604 by a suitable communication network such as a local area network (LAN) or a wide area network (WAN). In some embodiments, the external P/RNG is a central deterministic system that provides random or pseudo random results to one or more connected wager servers.

During operation of the wager server, the external system communicates wager execution commands 629 to the wager server 604. The wager server 604 receives the wager execution commands and uses the wager execution commands to trigger execution of a wager in accordance with a wagering proposition. The wager server 604 executes the wager and determines a wager outcome for the wager. The wager server communicates wager outcome data 631 of the wager outcome to the external system.

In some embodiments, the wager server uses the wager execution commands to select a paytable 628 to use and/or an amount of Cr, AC, interactive elements, or objects to wager.

In some embodiments, the wager outcome data may include, but is not limited to, an amount of Cr, AC, interactive elements, or objects won in the wager.

In various embodiments, the wager outcome data may include, but is not limited to, an amount of Cr, AC, interactive elements, or objects in the one or more meters 626.

In some embodiments, the wager outcome data includes state data for the wagering proposition of the executed wager. The state data may correspond to one or more game states of a wagering proposition that is associated with the wagering proposition. Examples of state data include, but are not limited to, reel strips in an operation state or a final state for a reel-based wagering proposition, one or more dice positions for a dice-based wagering proposition, positions of a roulette wheel and roulette ball, position of a wheel of fortune, or the like.

In various embodiments, the wagering control module 622 determines an amount of a wager and a paytable to use from the one or more paytables 623. In such embodiments, in response to the wager execution commands triggering execution of the wager, the wager control module 622 executes the wager by requesting a P/RNG result from the P/RNG 620; retrieving a paytable from the one or more paytables 623; adjusting the one or more credit meters 626 for an amount of the wager; applying the P/RNG result to the retrieved paytable; multiplying the resultant factor from the paytable by an amount wagered to determine a wager outcome; updating the one or more meters 626 based on the wager outcome; and communicating the wager outcome to the external device.

In various embodiments, an external system communicates a request for a P/RNG result from the wager server 604. In response, the wager server 604 returns a P/RNG result as a function of an internal P/RNG or a P/RNG external to the external system to which the wager server 604 is operatively connected.

In some embodiments, a communication exchange between the wager server 604 and an external system relate to the external system support for coupling a P/RNG result to a particular paytable contained in the wager server 604. In such an exchange, the external system communicates to the wager server 604 as to which of the one or more paytables 623 to use, and requests a result whereby the P/RNG result would be associated with the requested paytable 623. The result of the coupling is returned to the external system. In such an exchange, no actual Cr, AC, interactive element, or object wager is conducted, but might be useful in coupling certain non-value wagering interactive application behaviors and propositions to the same final resultant wagering return which is understood for the delayed wager interleaved wagering system to conduct wagering.

In some embodiments, the wager server 604 may also include storage for statuses, wagers, wager outcomes, meters and other historical events in a storage device 616.

In some embodiments, an authorization access module provides a process to permit access and command exchange with the wager server 604 and access to the one or more credit meters 626 for the amount of Cr, AC, interactive elements, or objects being wagered by the user in the delayed wager interleaved wagering system.

In numerous embodiments, communication occurs between various types of a wager server and an external system 630, such as process controller. In some of these embodiments, the purpose of the wager server is to allocate wagers to pools, detect occurrences of one or more events upon which the wagers were made, and determine the wager outcomes for each individual wager based on the number of winning wagers and the amount paid into the pool.

In some embodiments, the wager server manages accounts for individual users wherein the users make deposits into the accounts, amounts are deducted from the accounts, and amounts are credited to the users' accounts based on the wager outcomes.

In some embodiments a wager server is a pari-mutuel wagering system such as used for wagering on an events such as horse races, greyhound races, sporting events and the like. In a pari-mutuel wagering system, user's wagers on the outcome of an event are allocated to a pool. When the event occurs, wager outcomes are calculated by sharing the pool among all winning wagers.

In various embodiments, a wager server is a central determination system, such as but not limited to a central determination system for a Class II wagering system or a wagering system in support of a "scratch off" style lottery. In such a wagering system, a user plays against other users and competes for a common prize. In a given set of wager outcomes, there are a certain number of wins and losses. Once a certain wager outcome has been determined, the same wager outcome cannot occur again until a new set of wager outcomes is generated.

In numerous embodiments, communication occurs between various components of a wager server 604 and an external system, such as a process controller. In some of these embodiments, the purpose of the wager server 604 is to manage wagering on wagering events and to provide random (or pseudo random) results from a P/RNG.

Referring now to FIG. 5B, wager server 604 includes a bus 732 that provides an interface for one or more processors 734, random access memory (RAM) 736, read only memory (ROM) 738, machine-readable storage medium 740, one or more user output devices 742, one or more user input devices 744, and one or more communication interface and/or network interface devices 746.

The one or more processors 734 may take many forms, such as, but not limited to, a central processing unit (CPU), a multi-processor unit (MPU), an ARM processor, a controller, a programmable logic device, or the like.

In the example embodiment, the one or more processors 734 and the random access memory (RAM) 736 form a wager server processing unit 799. In some embodiments, the wager server processing unit includes one or more processors operatively connected to one or more of a RAM, ROM, and machine-readable storage medium; the one or more processors of the wager server processing unit receive instructions stored by the one or more of a RAM, ROM, and machine-readable storage medium via a bus; and the one or more processors execute the received instructions. In some embodiments, the wager server processing unit is an ASIC (Application-Specific Integrated Circuit). In some embodiments, the wager server processing unit is a SoC (System-on-Chip).

Examples of output devices 742 include, but are not limited to, display screens, light panels, and/or lighted displays. In accordance with particular embodiments, the one or more processors 734 are operatively connected to audio output devices such as, but not limited to speakers, and/or sound amplifiers. In accordance with many of these embodiments, the one or more processors 734 are operatively connected to tactile output devices like vibrators, and/or manipulators.

Examples of user input devices 734 include, but are not limited to, tactile devices including but not limited to, keyboards, keypads, touch screens, and/or trackballs; non-contact devices such as audio input devices; motion sensors and motion capture devices that the wager server can use to receive inputs from a user when the user interacts with the wager server 604.

The one or more communication interface and/or network interface devices 746 provide one or more wired or wireless interfaces for exchanging data and commands between the wager server 604 and other devices that may be included in a delayed wager interleaved wagering system. Such wired and wireless interfaces include, but are not limited to: a Universal Serial Bus (USB) interface; a Bluetooth interface; a Wi-Fi interface; an Ethernet interface; a Near Field Communication (NFC) interface; a plain old telephone system (POTS) interface; a cellular or satellite telephone network interface; and the like.

The machine-readable storage medium 740 stores machine-executable instructions for various components of a wager server, such as but not limited to: an operating system 748; one or more application programs 750; one or more device drivers 752; and delayed wager interleaved wagering system wager server instructions and data 754 for use by the one or more processors 734 to provide the features of a delayed wager interleaved wagering system wager server as described herein.

In various embodiments, the machine-readable storage medium 740 is one of a (or a combination of two or more of) a hard drive, a flash drive, a DVD, a CD, a flash storage, a solid state drive, a ROM, an EIEPROM, and the like.

In operation, the machine-executable instructions are loaded into memory 736 from the machine-readable storage medium 740, the ROM 738 or any other storage location. The respective machine-executable instructions are accessed by the one or more processors 734 via the bus 732, and then executed by the one or more processors 734. Data used by the one or more processors 734 are also stored in memory 736, and the one or more processors 734 access such data during execution of the machine-executable instructions. Execution of the machine-executable instructions causes the one or more processors 734 to control the wager server 604 to provide the features of a delayed wager interleaved wagering system wager server as described herein Although the wager server 604 is described herein as being constructed from or configured using one or more processors and machine-executable instructions stored and executed by hardware components, the wager server can be composed of only hardware components in accordance with other embodiments. In addition, although the storage medium 740 is described as being operatively connected to the one or more processors through a bus, those skilled in the art of processing devices will understand that the storage medium can include removable media such as, but not limited to, a USB memory device, an optical CD ROM, magnetic media such as tape and disks. In some embodiments, the storage medium 740 can be accessed by the one or more processors 734 through one of the interfaces or using a communication link. Furthermore, any of the user input devices or user output devices can be operatively connected to the one or more processors 734 via one of the interfaces or using a communication link.

In various embodiments, the wager server 604 may be used to construct other components of a delayed wager interleaved wagering system as described herein.

In some embodiments, components of a wager server and a process controller of a delayed wager interleaved wagering system may be constructed from or configured using a single device using processes that communicate using an interprocess communication protocol. In other such embodiments, the components of a wager server and a process controller of a delayed wager interleaved wagering system may communicate by passing messages, parameters or the like.

It should be understood that there may be many embodiments of a wager server 604 which could be possible, including forms where many modules and components of the wager server are located in various servers and locations, so the foregoing is not meant to be exhaustive or all inclusive, but rather provide data on various embodiments of a wager server 604.

Figure 6A:
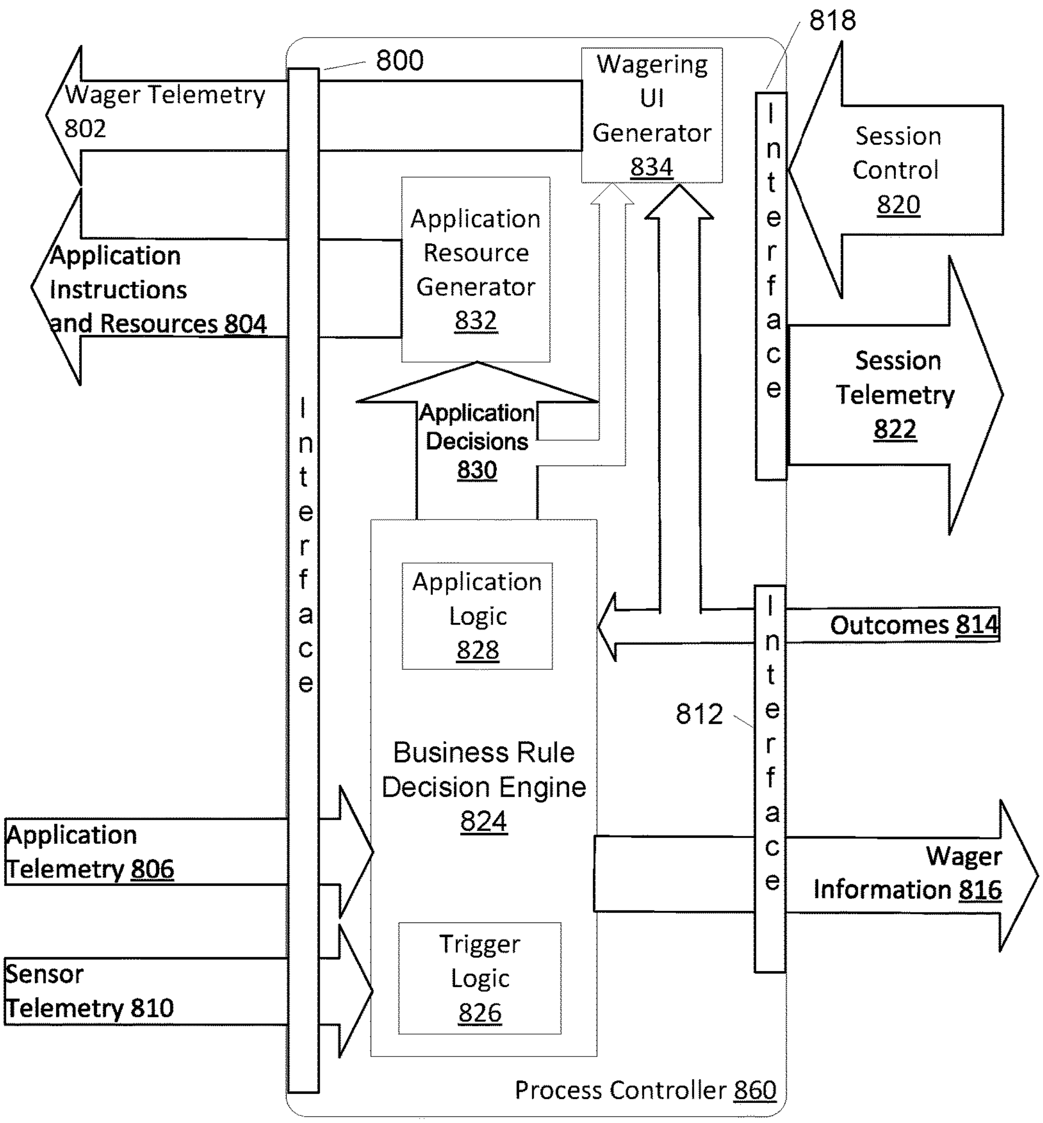
FIGS. 6A and 6B are diagrams of a structure of a process controller of a delayed wager interleaved wagering system in accordance with various embodiments of the invention.
Figure 6B:
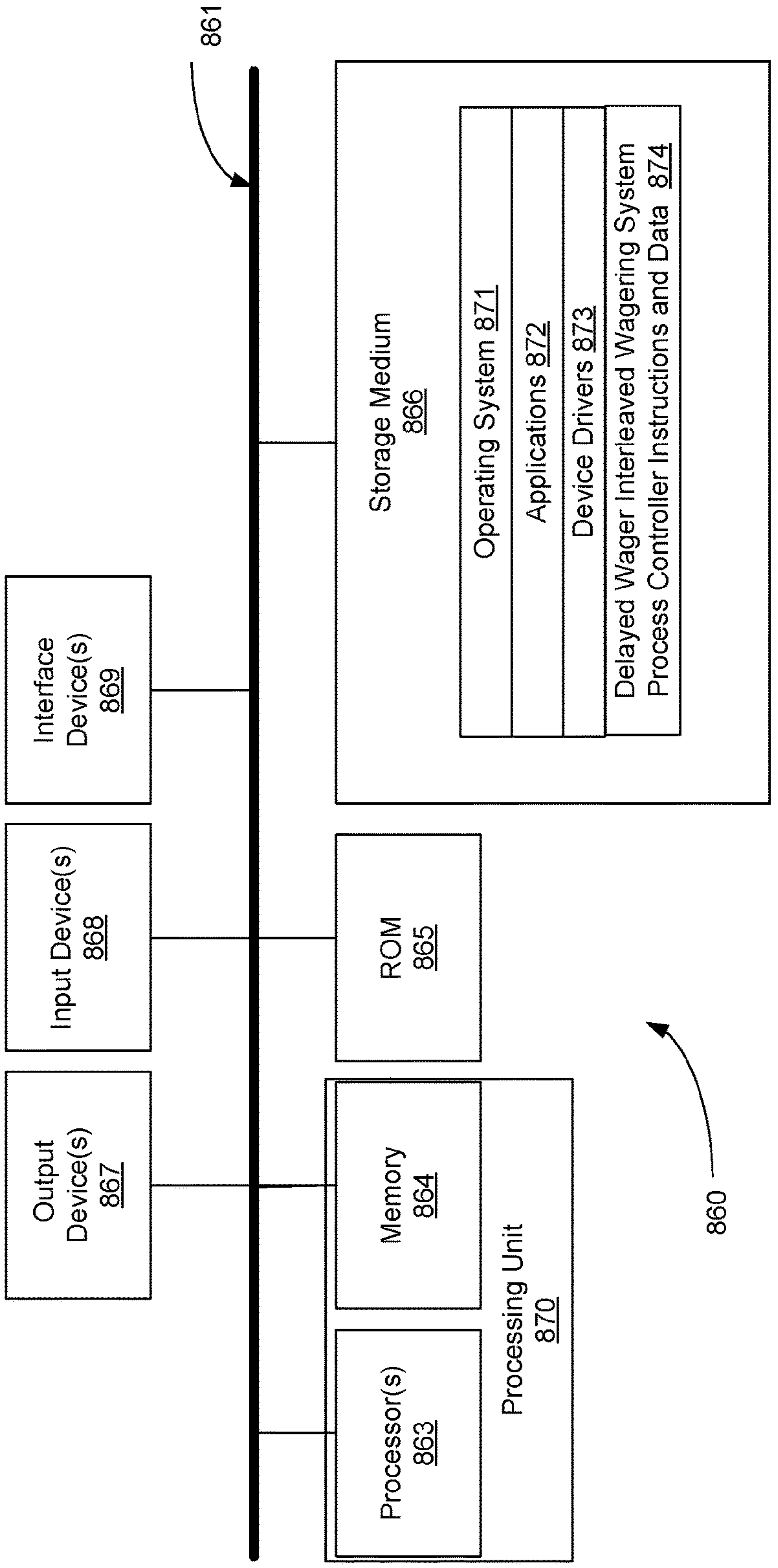

FIGS. 6A and 6B are diagrams of a structure of a process controller of a delayed wager interleaved wagering system in accordance with various embodiments of the invention. A process controller may be constructed from or configured using one or more processing devices configured to perform the operations of the process controller. In many embodiments, a process controller can be constructed from or configured using various types of processing devices including, but not limited to, a mobile device such as a smartphone, a personal digital assistant, a wireless device such as a tablet computer or the like, an electronic gaming machine, a personal computer, a gaming console, a set-top box, a computing device, a controller, or the like.

Referring now to FIG. 6A, in many embodiments, a process controller 860, suitable for use as process controller 112 of FIG. 1A, manages operation of a delayed wager interleaved wagering system, with a wager server and an interactive processing device being support units to the process controller 860. The process controller 860 provides an interface between the interactive application, provided by an interactive processing device, and a wagering proposition, provided by a wager server.

In some embodiments, the process controller 860 includes an interactive processing device interface 800 to an interactive processing device. The interactive processing device interface 800 provides for communication of data between an interactive processing device and the process controller 860, including but not limited to wager telemetry data 802, application instructions and resources 804, application telemetry data 806, and sensor telemetry data 810 as described herein.

In various embodiments, the process controller 860 includes a wager server interface 812 to a wager server. The wager server interface 812 provides for communication of data between the process controller 860 and a wager server, including but not limited to wager outcomes 814 and wager execution commands 816 as described in.

In some embodiments, the process controller 860 includes a session/management server interface 818 to a session/management server. The session/management server interface 818 provides for communication of data between the process controller 860 and a session/management server, including but not limited to session control data 820 and session telemetry data 822 as described herein.

The process controller 860 includes a rule-based decision engine 824 that receives telemetry data, such as application telemetry data and sensor telemetry data, from an interactive processing device. The rule-based decision engine 824 uses the telemetry data, along with wager logic 826 to generate wager execution commands used to trigger a wager in a wager server.

In some embodiments, the application telemetry data includes, but is not limited to, application environment variables that indicate the state of an interactive application being used by a user, interactive processing device data indicating a state of an interactive processing device, and user actions and interactions between a user and an interactive application provided by an interactive processing device. The wagering and/or wager execution commands may include, but are not limited to, an amount and type of the wager, a trigger of the wager, and a selection of a paytable to be used when executing the wager.

In some embodiments, the rule-based decision engine 824 also receives wager outcome data from a wager server. The decision engine 824 uses the wager outcome data, in conjunction with telemetry data and application logic 828 to generate application decisions 830 communicated to an application resource generator 832. The application resource generator 832 receives the application decisions and uses the application decisions to generate application commands and application resources to be communicated to an interactive application.

In many embodiments, the process controller 860 includes a pseudo random or random result generator used to generate random results that are communicated to the application resource generator 832. The application resource generator uses the random results to generate application commands and application resources to be communicated to an interactive processing device for use by an interactive application.

In various embodiments, the rule-based decision engine 824 also determines an amount of AC to award to a user based at least in part on the user's use of an interactive application of the delayed wager interleaved wagering system as determined from application telemetry data. In some embodiments, wager outcome data may also be used to determine the amount of AC that should be awarded to the user.

In numerous embodiments, an interactive application is a skill-based interactive application and the AC is awarded to the user for the user's skillful play of the skill-based interactive application.

In some embodiments, the application decisions and wager outcome data are communicated to a wagering interface generator 834. The wagering interface generator 834 receives the application decisions and wager outcome data and generates wager telemetry data describing the state of wagering and credit accumulation and loss for the delayed wager interleaved wagering system. In some embodiments, the wager telemetry data 146 may include, but is not limited to, amounts of AC and interactive elements earned, lost or accumulated by the user through use of the interactive application as determined from the application decisions, and Cr amounts won, lost or accumulated as determined from the wager outcome data and the one or more credit meters.

In some embodiments, the wager outcome data 814 also includes data about one or more game states of a wagering proposition executed in accordance with a wagering proposition by a wager server. In various such embodiments, the wagering interface generator 834 generates a wagering proposition process display and/or wagering proposition state display using the one or more game states of the wagering proposition. The wagering proposition process display and/or wagering proposition state display is included in wager telemetry data that is communicated to an interactive processing device. The wagering proposition process display and/or a wagering proposition state display is displayed by a wagering interface of the interactive processing device to a user. In other such embodiments, the one or more game states of the wagering proposition are communicated to an interactive processing device and a wagering interface of the interactive processing device generates a wagering proposition process display and/or wagering proposition state display using the one or more game states of the wagering proposition for display to a user.

The process controller 860 can further operatively connect to a wager server to determine an amount of credit or interactive elements available and other wagering metrics of a wagering proposition. Thus, the process controller 860 may potentially affect an amount of Cr in play for participation in the wagering events of a wagering proposition provided by the wager server. The process controller 860 may additionally include various audit logs and activity meters. In some embodiments, the process controller 860 can also couple to a centralized server for exchanging various data related to the user and the activities of the user during game play of a delayed wager interleaved wagering system.

In some embodiments, the operation of the process controller 860 does not affect the provision of a wagering proposition by a wager server except for user choice parameters that are allowable in accordance with the wagering proposition. Examples of user choice parameters include, but are not limited to: wager terms such as but not limited to a wager amount; speed of game play (for example, by pressing a button or pulling a handle of a slot machine); and/or agreement to wager into a bonus round.

In a number of embodiments, communication of wager execution commands between a wager server and the process controller 860 can further be used to communicate various wagering control factors that the wager server uses as input. Examples of wagering control factors include, but are not limited to, an amount of Cr, AC, interactive elements, or objects consumed per wagering event, and/or the user's election to enter a jackpot round.

In some embodiments, the process controller 860 utilizes a wagering interface to communicate certain interactive application data to the user, including but not limited to, club points, user status, control of the selection of user choices, and messages which a user can find useful in order to adjust the interactive application experience or understand the wagering status of the user in accordance with the wagering proposition in the wager server.

In some embodiments, the process controller 860 utilizes a wagering interface to communicate aspects of a wagering proposition to the user including, but not limited to, odds of certain wager outcomes, amount of Cr, AC, interactive elements, or objects in play, and amounts of Cr, AC, interactive elements, or objects available.

In a number of embodiments, a wager server can accept wager proposition factors including, but not limited to, modifications in the amount of Cr, AC, interactive elements, or objects wagered on each individual wagering event, a number of wagering events per minute the wager server can resolve, entrance into a bonus round, and other factors. In several embodiments, the process controller 860 can communicate a number of factors back and forth to the wager server, such that an increase/decrease in a wagered amount can be related to the change in user profile of the user in the interactive application. In this manner, a user can control a wager amount per wagering event in accordance with the wagering proposition with the change mapping to a parameter or component that is applicable to the interactive application experience.

Referring now to FIG. 6B, process controller 860 includes a bus 861 providing an interface for one or more processors 863, random access memory (RAM) 864, read only memory (ROM) 865, machine-readable storage medium 866, one or more user output devices 867, one or more user input devices 868, and one or more communication interface and/or network interface devices 869.

The one or more processors 863 may take many forms, such as, but not limited to: a central processing unit (CPU); a multi-processor unit (MPU); an ARM processor; a programmable logic device; or the like.

Examples of output devices 867 include, include, but are not limited to: display screens; light panels; and/or lighted displays. In accordance with particular embodiments, the one or more processors 863 are operatively connected to audio output devices such as, but not limited to: speakers; and/or sound amplifiers. In accordance with many of these embodiments, the one or more processors 863 are operatively connected to tactile output devices like vibrators, and/or manipulators.

In the example embodiment, the one or more processors 863 and the random access memory (RAM) 864 form a process controller processing unit 870. In some embodiments, the process controller processing unit includes one or more processors operatively connected to one or more of a RAM, ROM, and machine-readable storage medium; the one or more processors of the process controller processing unit receive instructions stored by the one or more of a RAM, ROM, and machine-readable storage medium via a bus; and the one or more processors execute the received instructions. In some embodiments, the process controller processing unit is an ASIC (Application-Specific Integrated Circuit). In some embodiments, the process controller processing unit is a SoC (System-on-Chip).

Examples of user input devices 868 include, but are not limited to: tactile devices including but not limited to, keyboards, keypads, foot pads, touch screens, and/or trackballs; non-contact devices such as audio input devices; motion sensors and motion capture devices that the process controller can use to receive inputs from a user when the user interacts with the process controller 860.

The one or more communication interface and/or network interface devices 869 provide one or more wired or wireless interfaces for exchanging data and commands between the process controller 860 and other devices that may be included in a delayed wager interleaved wagering system. Such wired and wireless interfaces include, but are not limited to: a Universal Serial Bus (USB) interface; a Bluetooth interface; a Wi-Fi interface; an Ethernet interface; a Near Field Communication (NFC) interface; a plain old telephone system (POTS), cellular, or satellite telephone network interface; and the like.

The machine-readable storage medium 866 stores machine-executable instructions for various components of the process controller 860 such as, but not limited to: an operating system 871; one or more applications 872; one or more device drivers 873; and delayed wager interleaved wagering system process controller instructions and data 874 for use by the one or more processors 863 to provide the features of a process controller as described herein.

In various embodiments, the machine-readable storage medium 870 is one of a (or a combination of two or more of) a hard drive, a flash drive, a DVD, a CD, a flash storage, a solid state drive, a ROM, an EIEPROM, and the like.

In operation, the machine-executable instructions are loaded into memory 864 from the machine-readable storage medium 866, the ROM 865 or any other storage location. The respective machine-executable instructions are accessed by the one or more processors 863 via the bus 861, and then executed by the one or more processors 863. Data used by the one or more processors 863 are also stored in memory 864, and the one or more processors 863 access such data during execution of the machine-executable instructions. Execution of the machine-executable instructions causes the one or more processors 863 to control the process controller 860 to provide the features of a delayed wager interleaved wagering system process controller as described herein.

Although the process controller 860 is described herein as being constructed from or configured using one or more processors and instructions stored and executed by hardware components, the process controller can be composed of only hardware components in accordance with other embodiments. In addition, although the storage medium 866 is described as being operatively connected to the one or more processors through a bus, those skilled in the art of process controllers will understand that the storage medium can include removable media such as, but not limited to, a USB memory device, an optical CD ROM, magnetic media such as tape and disks. Also, in some embodiments, the storage medium 866 may be accessed by processor 863 through one of the interfaces or using a communication link. Furthermore, any of the user input devices or user output devices may be operatively connected to the one or more processors 863 via one of the interfaces or using a communication link.

In various embodiments, the process controller 860 may be used to construct other components of a delayed wager interleaved wagering system as described herein.

In some embodiments, components of an interactive processing device and a process controller of a delayed wager interleaved wagering system may be constructed from or configured using a single device using processes that communicate using an interprocess communication protocol. In other such embodiments, the components of an interactive processing device and a process controller of a delayed wager interleaved wagering system may communicate by passing messages, parameters or the like.

Figure 7A:
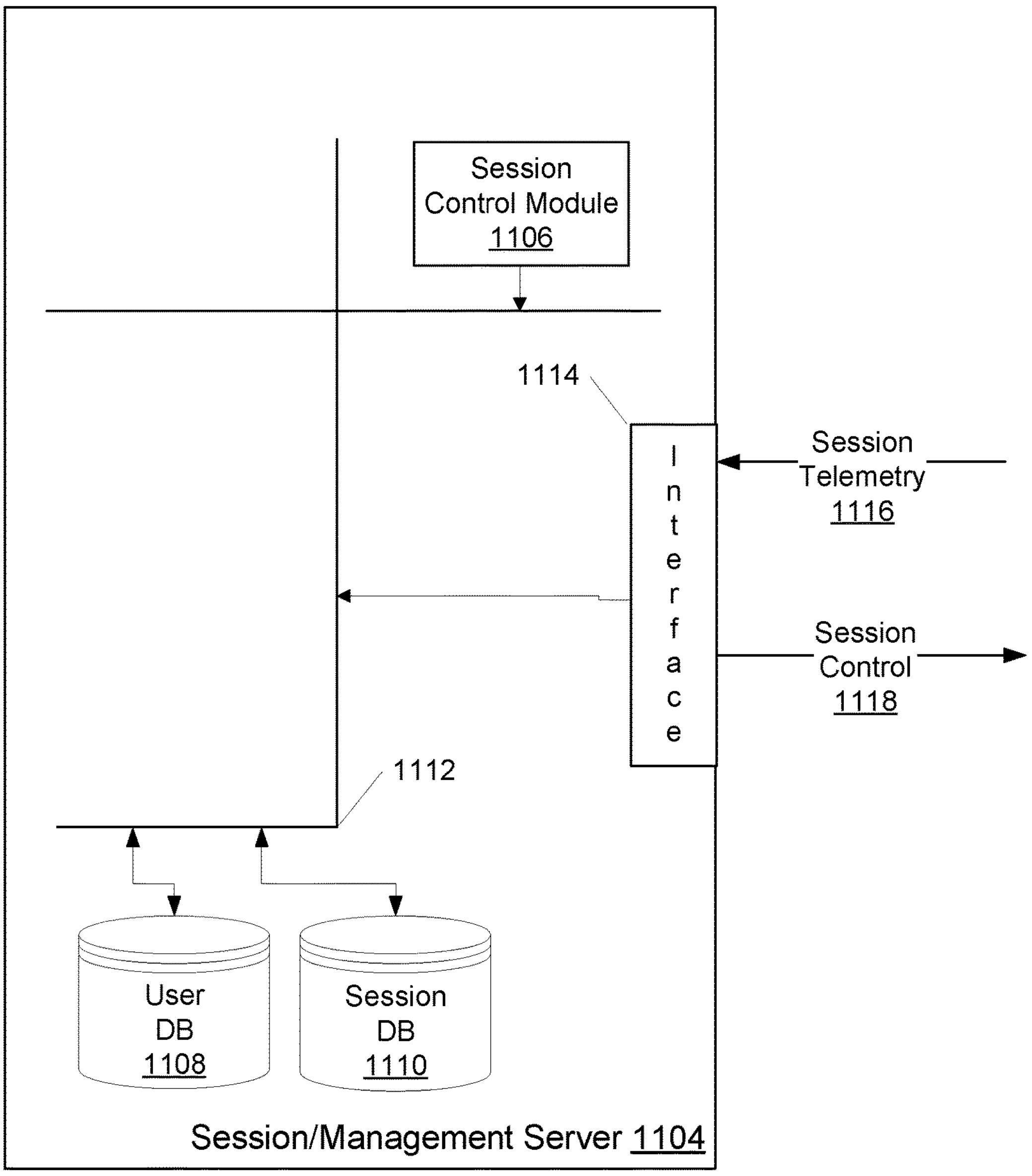
FIGS. 7A and 7B are diagrams of a structure of a session/management server of a delayed wager interleaved wagering system in accordance with various embodiments of the invention.
Figure 7B:
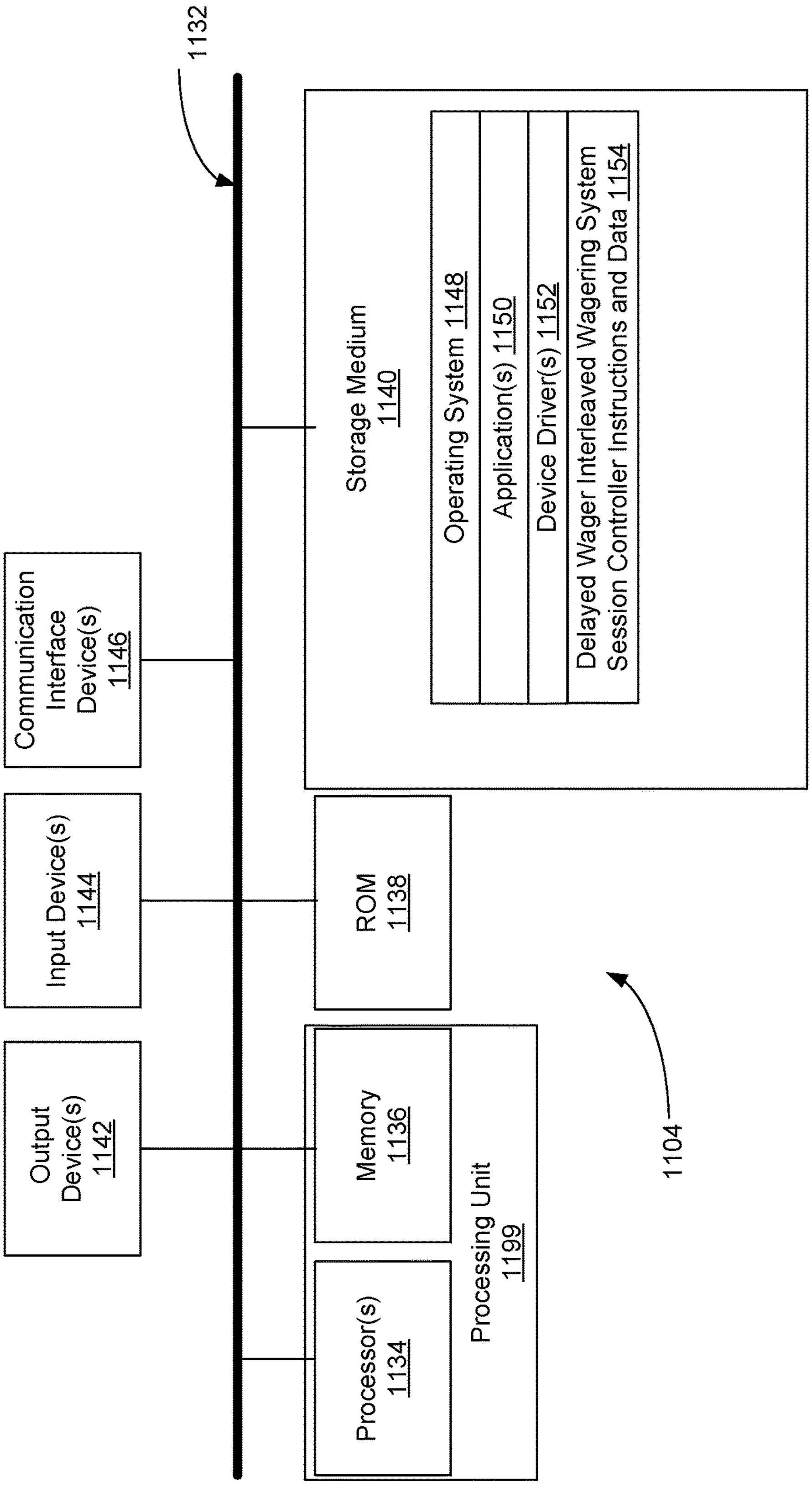

FIGS. 7A and 7B are diagrams of a structure of a session/management server of a delayed wager interleaved wagering system in accordance with various embodiments of the invention. A session/management server may be constructed from or configured using one or more processing devices configured to perform the operations of the session/management server. In many embodiments, a wager session can be constructed from or configured using various types of processing devices including, but not limited to, a mobile device such as a smartphone or the like, a personal digital assistant, a wireless device such as a tablet computer or the like, an electronic gaming machine, a personal computer, a gaming console, a set-top box, a computing device, a controller, a server, or the like.

Referring now to FIG. 7A, in various embodiments, a session/management server 1104, suitable for use as session/management server 150 of FIG. 1A, includes a user management and session control module 1106 whose processes may include, but are not limited to, registering users of a delayed wager interleaved wagering system, validating users of a delayed wager interleaved wagering system using user registration data, managing various types of sessions for users of the delayed wager interleaved wagering system, and the like.

The session/management server 1104 may further include a datastore 1108 storing user data used to manage user registration and validation. The session/management server 1104 may further include a datastore 1110 storing session data used to manage one or more sessions.

The various session/management server components can interface with each other via an internal bus 1112 and/or other appropriate communication mechanism.

An interface 1114 allows the session/management server 1104 to operatively connect to one or more external devices, such as one or more process controllers, wager servers and/or interactive processing devices as described herein. The interface provides for receiving session telemetry data 1116 from the one more external devices as described herein. The session telemetry data includes, but is not limited to, amounts of AC earned by one or more users, requests for entering into a session as described herein, and telemetry data regarding the progress of one or more users during a session. The interface 1114 may also provide for communicating secession control data 1118 used to manage a session as described herein.

In numerous embodiments, the interface between the session/management server and other systems/devices may be a wide area network (WAN) such as the Internet. However, other methods of communication may be used including, but not limited to, a local area network (LAN), a universal serial bus (USB) interface, and/or some other method by which two electronic devices could communicate with each other.

During operation of the session/management server, the external system communicates session telemetry data to the session/management server. The session/management server receives the session telemetry data and uses the session telemetry data to generate session control data as described herein. The session/management server communicates the session control data to the external system.

Referring now to FIG. 7B, session/management server 1104 includes a bus 1132 that provides an interface for one or more processors 1134, random access memory (RAM) 1136, read only memory (ROM) 1138, machine-readable storage medium 1140, one or more user output devices 1142, one or more user input devices 1144, and one or more communication interface and/or network interface devices 1146.

The one or more processors 1134 may take many forms, such as, but not limited to, a central processing unit (CPU), a multi-processor unit (MPU), an ARM processor, a controller, a programmable logic device, or the like.

In the example embodiment, the one or more processors 1134 and the random access memory (RAM) 1136 form a session/management server processing unit 1199. In some embodiments, the session/management server processing unit includes one or more processors operatively connected to one or more of a RAM, ROM, and machine-readable storage medium; the one or more processors of the session/management server processing unit receive instructions stored by the one or more of a RAM, ROM, and machine-readable storage medium via a bus; and the one or more processors execute the received instructions. In some embodiments, the session/management server processing unit is an ASIC (Application-Specific Integrated Circuit). In some embodiments, the session/management server processing unit is a SoC (System-on-Chip).

Examples of output devices 1142 include, but are not limited to, display screens, light panels, and/or lighted displays. In accordance with particular embodiments, the one or more processors 1134 are operatively connected to audio output devices such as, but not limited to speakers, and/or sound amplifiers. In accordance with many of these embodiments, the one or more processors 1134 are operatively connected to tactile output devices like vibrators, and/or manipulators.

Examples of user input devices 1144 include, but are not limited to, tactile devices including but not limited to, keyboards, keypads, touch screens, and/or trackballs; non-contact devices such as audio input devices; motion sensors and motion capture devices that the session/management server can use to receive inputs from a user when the user interacts with the session/management server 1104.

The one or more communication interface and/or network interface devices 1146 provide one or more wired or wireless interfaces for exchanging data and commands between the session/management server 1104 and other devices that may be included in a delayed wager interleaved wagering system. Such wired and wireless interfaces include, but are not limited to: a Universal Serial Bus (USB) interface; a Bluetooth interface; a Wi-Fi interface; an Ethernet interface; a Near Field Communication (NFC) interface; a plain old telephone system (POTS) interface; a cellular or satellite telephone network interface; and the like.

The machine-readable storage medium 1140 stores machine-executable instructions for various components of a session/management server, such as but not limited to: an operating system 1148; one or more application programs 1150; one or more device drivers 1152; and delayed wager interleaved wagering system session/management server instructions and data 1154 for use by the one or more processors 1134 to provide the features of a delayed wager interleaved wagering system session/management server as described herein.

In various embodiments, the machine-readable storage medium 1140 is one of a (or a combination of two or more of) a hard drive, a flash drive, a DVD, a CD, a flash storage, a solid state drive, a ROM, an EIEPROM, and the like.

In operation, the machine-executable instructions are loaded into memory 736 from the machine-readable storage medium 1140, the ROM 1138 or any other storage location. The respective machine-executable instructions are accessed by the one or more processors 1134 via the bus 1132, and then executed by the one or more processors 1134. Data used by the one or more processors 1134 are also stored in memory 1136, and the one or more processors 1134 access such data during execution of the machine-executable instructions. Execution of the machine-executable instructions causes the one or more processors 1134 to control the session/management server 1104 to provide the features of a delayed wager interleaved wagering system session/management server as described herein Although the session/management server 1104 is described herein as being constructed from or configured using one or more processors and machine-executable instructions stored and executed by hardware components, the session/management server can be composed of only hardware components in accordance with other embodiments. In addition, although the storage medium 1140 is described as being operatively connected to the one or more processors through a bus, those skilled in the art of processing devices will understand that the storage medium can include removable media such as, but not limited to, a USB memory device, an optical CD ROM, magnetic media such as tape and disks. In some embodiments, the storage medium 1140 can be accessed by the one or more processors 1134 through one of the interfaces or using a communication link. Furthermore, any of the user input devices or user output devices can be operatively connected to the one or more processors 1134 via one of the interfaces or using a communication link.

In various embodiments, the session/management server 1104 may be used to construct other components of a delayed wager interleaved wagering system as described herein.

In some embodiments, components of a session/management server and a process controller of a delayed wager interleaved wagering system may be constructed from or configured using a single device using processes that communicate using an interprocess communication protocol. In other such embodiments, the components of a session/management server and a process controller of a delayed wager interleaved wagering system may communicate by passing messages, parameters or the like.

In some embodiments, components of a session/management server and a wager server of a delayed wager interleaved wagering system may be constructed from or configured using a single device using processes that communicate using an interprocess communication protocol. In other such embodiments, the components of a session/management server and a process controller of a delayed wager interleaved wagering system may communicate by passing messages, parameters or the like.

It should be understood that there may be many embodiments of a session/management server 1104 which could be possible, including forms where many modules and components of the session/management server are located in various servers and locations, so the foregoing is not meant to be exhaustive or all inclusive, but rather provide data on various embodiments of a session/management server 1104.

In numerous embodiments, any of a wager server, a process controller, an interactive processing device, or a session/management server as described herein can be constructed from or configured using multiple processing devices, whether dedicated, shared, or distributed in any combination thereof, or can be constructed from or configured using a single processing device. In addition, while certain aspects and features of delayed wager interleaved wagering system processes described herein have been attributed to a wager server, a process controller, an interactive processing device, or a session/management server, these aspects and features can be provided in a distributed form where any of the features or aspects can be provided by any of a session/management server, a wager server, a process controller, and/or an interactive processing device within a delayed wager interleaved wagering system without deviating from the spirit of the invention.

Although various components of delayed wager interleaved wagering systems are discussed herein, delayed wager interleaved wagering systems can be configured with any component as appropriate to the specification of a specific application in accordance with embodiments of the invention. In certain embodiments, components of a delayed wager interleaved wagering system, such as a session/management server, a process controller, a wager server, and/or an interactive processing device, can be configured in different ways for a specific delayed wager interleaved wagering system.

In some embodiments, components of a session/management server, an interactive processing device, a process controller, and/or a wager server of a delayed wager interleaved wagering system may be constructed from or configured using a single device using processes that communicate using an interprocess communication protocol. In many embodiments, the components of a session/management server, an interactive processing device, a process controller and a wager server of a delayed wager interleaved wagering system may communicate by passing messages, parameters or the like.

In addition, while certain aspects and features of delayed wager interleaved wagering system processes described herein have been attributed to a session/management server, a wager server, a process controller, or an interactive processing device, these aspects and features can be provided in a distributed form where any of the features or aspects can be provided by any of a session/management server, a wager server, a process controller, and/or an interactive processing device within a delayed wager interleaved wagering system.

Operation of Delayed Wager Interleaved Wagering Systems

Figure 8:
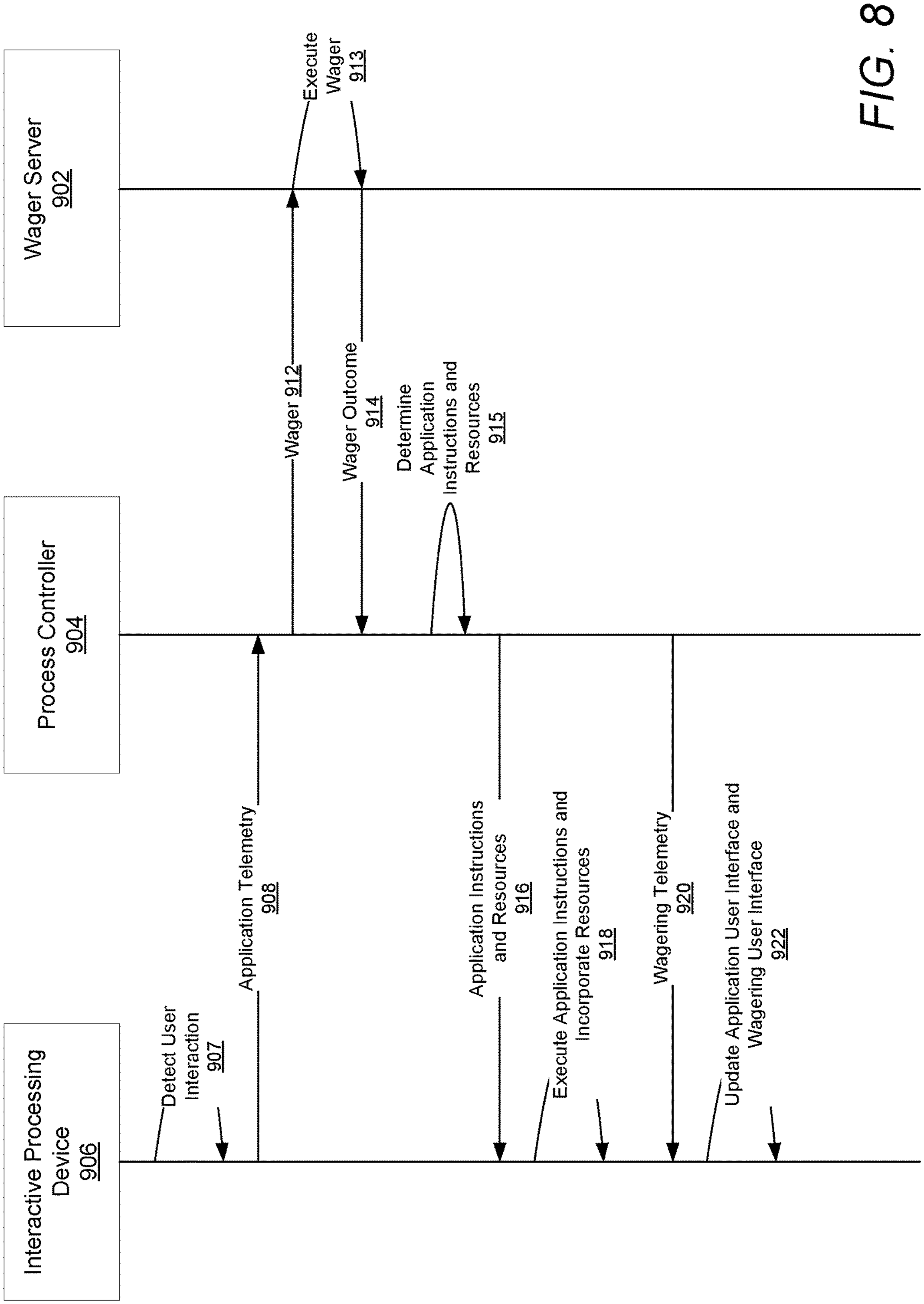
FIG. 8 is a sequence diagram of interactions between components of a delayed wager interleaved wagering system in accordance with various embodiments of the invention.

FIG. 8 is a sequence diagram of interactions between components of a delayed wager interleaved wagering system in accordance with various embodiments of the invention. The components of the delayed wager interleaved wagering system include a wager server 902, such as wager server 102 of FIG. 1A, a process controller 904, such as process controller 112 of FIG. 1A, and an interactive processing device 906, such as interactive processing device 120 of FIG. 1A. The process begins with the interactive processing device 906 detecting a user performing a user interaction in an application interface of an interactive application provided by the interactive processing device 906. The interactive processing device 906 communicates application telemetry data 908 to the process controller 904. The application telemetry data includes, but is not limited to, the user interaction detected by the interactive processing device 906.

The process controller 904 receives the application telemetry data 908. Upon determination by the process controller 904 that the user interaction indicates a wagering event, the process controller 904 generates wager execution commands including a wager request 912 that the process controller 904 uses to command the wager server 902 to execute a wager. The request for a wager event may include wager terms associated with a wagering proposition. The process controller 904 communicates the wager execution commands to the wager server 902.

The wager server 902 receives the wager execution commands 912 and uses the wager execution commands to execute (913) a wager in accordance with a wagering proposition. The wager server 902 communicates a wager outcome 914 of the executed wager to the process controller 904.

The process controller 904 receives the wager outcome and generates (915) interactive application instruction and resource data 916 for the interactive application. The process controller 904 uses the interactive application instruction and resource data 916 to command the interactive processing device. The process controller communicates the interactive application instruction and resource data 916 to the interactive processing device 906. The process controller also communicates wagering telemetry data 920 including the wager outcome to the interactive processing device 906.

The interactive processing device 906 receives the interactive application instruction and resource data 916 and wagering telemetry data 918. The interactive processing device 906 incorporates the received interactive application resources and executes the received interactive application commands (918). The interactive processing device updates (922) an application interface of the interactive application provided by the interactive processing device using the interactive application commands and the resources, and updates (922) a wagering interface using the wagering telemetry data.

In several embodiments, a user can interact with a delayed wager interleaved wagering system by using Cr for wagering in accordance with a wagering proposition along with AC and interactive elements in interactions with an interactive application. Wagering can be executed by a wager server while an interactive application can be executed by an interactive processing device and managed with a process controller.

Figure 9:
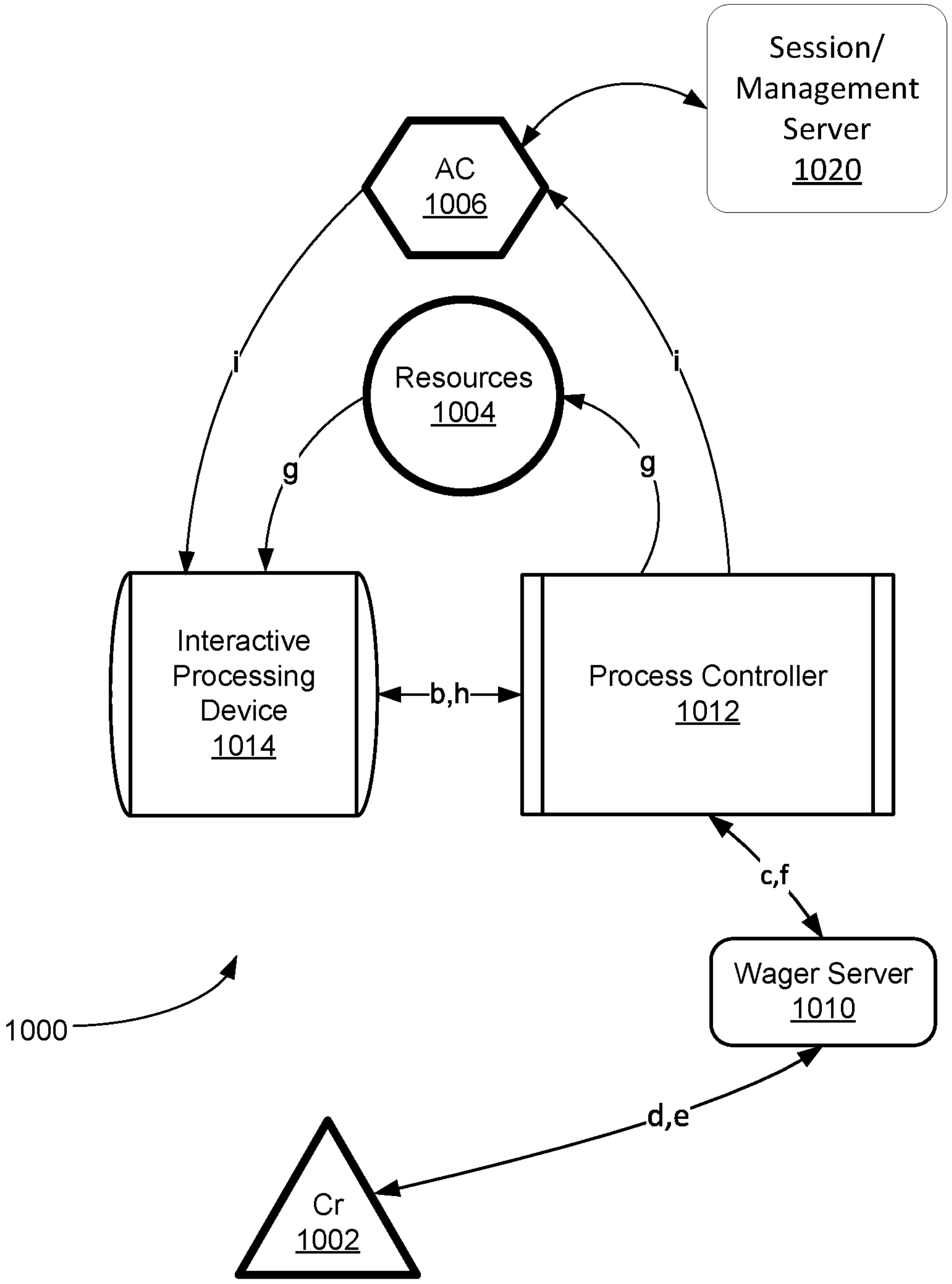
FIG. 9 is a collaboration diagram for components of a delayed wager interleaved wagering system in accordance with various embodiments of the invention.

FIG. 9 is a collaboration diagram that illustrates how resources such as AC, Cr, interactive elements, and objects are utilized in a delayed wager interleaved wagering system in accordance with various embodiments of the invention. The collaboration diagram 1000 illustrates that Cr 1002, interactive application resources including interactive elements and objects 1004 and AC 1006 can be utilized by a user 1008 in interactions with a wager server 1010, such as wager server 102 of FIG. 1A, a process controller 1012, such as wager server 112 of FIG. 1, and an interactive processing device 1014, such as interactive processing device 120 of FIG. 1A, of a delayed wager interleaved wagering system. The contribution of interactive elements and objects such as included in resources 1004, can be linked to a user's access to credits, such as Cr 1002 and/or AC 1006. Electronic receipt of these credits can come via a smart card, voucher or other portable media, or as received using a communication link from a server. In some embodiments, these credits can be drawn on demand from a user profile located in a database locally on a delayed wager interleaved wagering system or in a remote server.

A user's actions and/or decisions can affect an interactive application of interactive processing device 1014 that consume and/or accumulate AC 1004 and/or resources 1004 in an interactive application executed by an interactive processing device 1014, a wager server 101 and a process controller 1012. The process controller 1012 can monitor the activities taking place within an interactive application executed by an interactive processing device 1014 for wagering event occurrences. The process controller 1012 can also communicate the wagering event occurrences to the wager server 1010 that triggers a wager of Cr 1002 in accordance with a wagering proposition executed by the wager server 1010.

In several embodiments, the user commences interaction with the delayed wager interleaved wagering system by contributing credit to a delayed wager interleaved wagering system such as, but not limited to, Cr 1002 that may be credit in a real currency or may be credit in a virtual currency that is not fungible with a real currency, AC 1006 that may be application environment credits, and specified types of interactive application interactive elements and/or objects 1004. One or more of these contributions may be provided directly as currency and/or transferred in electronically. Electronic transfer may come via a smart card, voucher or other portable media, or as transferred in using a communication link from a user data server or delayed wager interleaved wagering system session/management server. In many embodiments, contributions may be drawn on demand from user accounts located in servers residing on the network or in the cloud on a real time basis as the credits, interactive elements and/or object are committed or consumed by the delayed wager interleaved wagering system. Generally, Cr is utilized and accounted for by the wager server 1010; and the resources 1004 and AC 1006 are utilized and accounted for by the process controller 1012 and/or the interactive processing device 1014.

The user interacts (a) with an interactive application provided by the interactive processing device 1014 with the interaction representing an action by the user within the context of the interactive application. The interactive processing device 1014 receives the user interaction and communicates (b) the interaction to the process controller 1012. The process controller 1012 receives the interaction and determines from the interaction whether or not a wager should be triggered. If a wager should be triggered, the process controller 1012 commands (c) the wager server 1010 to execute a wager in accordance with a wagering proposition associated with the interaction and thereby triggers a wager. The wager server receives the wager execution commands and executes the wager in accordance with the wagering proposition, and consumes (d) an appropriate amount of Cr 1002 for the wager. The wager server 1010 adjusts (e) the Cr 1002 based upon a wager outcome of the wager and communicates (f) the wager outcome to the process controller 1012 as to the outcome of the wager triggered by the process controller 1012. The process controller 1012 receives the wager outcome. The process controller determines what resources 1004 should be provided to the interactive processing device, generates the resources 1004 and application commands and commands (g) the interactive processing device 1014 using the resources 1004 and application commands. The interactive processing device receives the resources 1004 and application commands from the process controller 1012 and integrates them into the execution of the interactive application provided by the interactive processing device 1014.

In some embodiments, the process controller 1012 communicates (h) data about the wager outcome to the interactive processing device. The interactive processing device receives the wager outcome and displays the wager outcome to the user 1008.

In some embodiments, the process controller 1012 determines what resources and commands to provide to the interactive processing device 1014 for use by the interactive application provided by the interactive processing device 1014 partially on the basis of the wager outcome. In some such embodiments, resources are provided in a case that the wager was a winning wager for the user. In other such embodiments, fewer or no resources are provided in a case of a losing wager.

In some embodiments, the process controller 1012 determines what resources to provide based on internal logic of the process controller 1012. In some such embodiments, the process controller 1012 employs a random result generator, such as a P/RNG, to generate a random result and the random result is used to determine what resources are provided to the interactive processing device 1014.

In several embodiments, the process controller 1012 determines an increment or a decrement of an amount of AC 1006 using the interactions received from the interactive processing device. The increment or decremented amount is communicated (i) to the interactive processing device for display to the user.

In some embodiments, the process controller 1012 executes a wager of Cr as a virtual currency, AC, interactive elements or objects. In some such embodiments, the process controller 1012 employs a random result generator, such as a P/RNG, to generate a random result and the random result is used to determine a wager outcome in Cr as a virtual currency, AC, interactive elements or objects.

The following is description of an embodiment of the described collaboration where an interactive application provided by an interactive processing device of a delayed wager interleaved wagering system is a first person shooter game. The process begins by a user selecting a machine gun to use in the game and then fires a burst of bullets at an opponent. The interactive processing device can communicate to the process controller of the user's choice of weapon, that a burst of bullets was fired, and/or the outcome of the burst. The process controller communicates to the wager server that 3 credits (Cr) are to be wagered on the outcome of a wagering event to match the three bullets consumed. The wager server then performs the wagering event and determines the result of the wager and may determine the winnings from a paytable. The wager server consumes 3 credits of Cr for the wager and executes the specified wager. By way of example, the wager server may determine that the user hit a jackpot of 6 credits and returns the 6 credits to the Cr and communicates to the process controller that 3 net credits were won by the user.

The process controller communicates to the interactive processing device to add 3 bullets to an ammunition clip. The interactive processing device adds 3 bullets back to the ammo clip. The ammunition may be added by directly adding the ammunition to the clip or by allowing the user to find extra ammunition during use. The process controller logs the new user score (AC) in the game (as a function of the successful hit on the opponent) based on the interactive processing device communication, and adds 2 extra points to the user score since a jackpot has been won. The process controller then adds 10 points to the user score (AC) given the success of the hit which in this example is worth 8 points, plus the 2 extra point. Note that this example is only intended to provide an illustration of how credits flow in a delayed wager interleaved wagering system, but is not intended to be exhaustive and only lists only one of numerous possibilities of how a delayed wager interleaved wagering system may be configured to manage its fundamental credits.

In many embodiments, session/management server 1020, such as user account controller 150 of FIG. 1A, of a delayed wager interleaved wagering system is used to store AC for use of the user. In such an embodiment, AC is generated by the process controller based on the user's use of the delayed wager interleaved wagering system and an amount of the AC is communicated to the session/management server 1020. The session/management server stores the amount of AC between sessions. In some embodiments, the session/management server communicates an amount of AC to the process controller at the start of a session for use by the user during a session.

Figure 10:
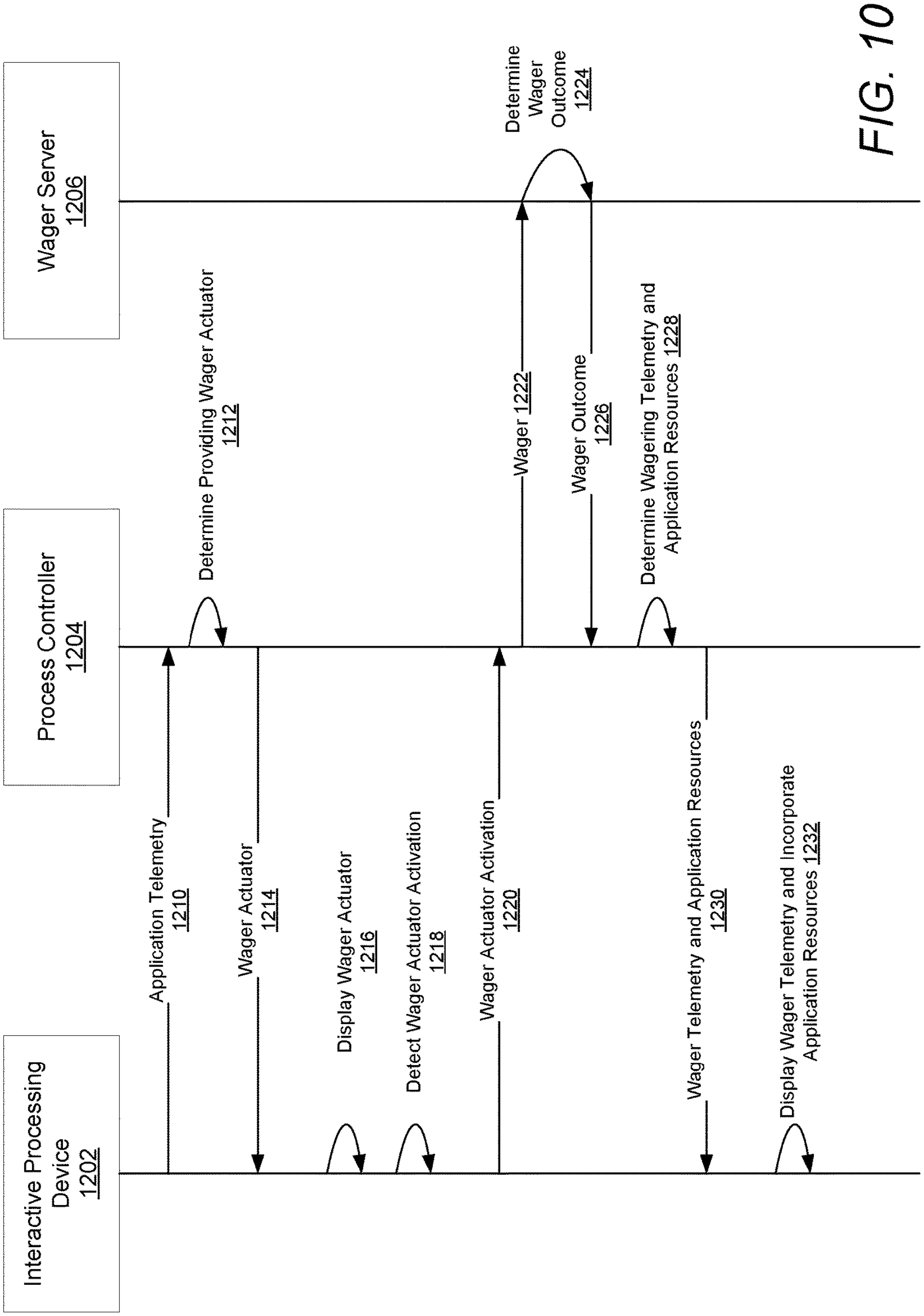
FIG. 10 is a sequence diagram of a delayed wager interleaved wagering system illustrating processes in accordance with embodiments of the invention.

FIG. 10 is a sequence diagram of a delayed wager interleaved wagering system illustrating processes in accordance with embodiments of the invention. In some embodiments, the system includes an interactive processing device 1202, an process controller 1204, and a wager server 1206, each as described herein.

In various embodiments, communication of outgoing data between a controller and another controller is achieved by the controller encoding data to be communicated into a signal and transmitting the signal to the another controller. Communication of incoming data is achieved by the controller receiving from the another controller signals encoding the incoming data. The controller decodes the signals to obtain the incoming data.

In some such embodiments, two or more controllers implement a controller-to-controller communication protocol as an interdevice communication protocol so that the two or more controllers may be implemented on different processing devices. The interdevice communication protocol may utilize a wired communication bus or wireless connection as a physical layer. In yet other such embodiments, the controller-to-controller communication protocol is implemented as a networking protocol so that the two or more controllers may be implemented on different devices operatively connected by a network. The networking protocol may utilize a wired communication bus or wireless connection as a physical layer. In many such embodiments, the network includes a cellular telephone network or the like and one or more of the controllers is a mobile device such as a smartphone or other device capable of using the cellular telephone network.

In some embodiments, communication is achieved by two or more of the controllers implementing a controller-to-controller communication protocol as an interprocess communication protocol so that the two or more controllers may be implemented on the same device.

In some embodiments, the interactive processing device 1202 provides an interactive application. In some embodiments, the interactive application is an interactive game. In some embodiments, the interactive game is a skill-based game. In some embodiments, the interactive game is a chance-based game.

In some embodiments, the interactive processing device 1202, the process controller 1204, and the wager server 1206 are separated into different components in order to distribute computing responsibilities to provide improved latency results. In some embodiments, the interactive processing device 1202 dedicates its resources toward providing the interactive application, and may be unable to perform the additional processing performed by the process controller 1204 without sacrificing latency.

During operation, in various embodiments, the interactive processing device 1202 is constructed to provide an interactive application display associated with an interactive application provided by the interactive processing device 1202. The interactive processing device 1202 communicates, to the process controller 1204, application telemetry data (1210). In some embodiments, the application telemetry data includes, but is not limited to, interactions and events that occur in the interactive application as executed by the interactive processing device 1202. In some embodiments, the interactive processing device 1202 is constructed to continuously generate and communicate the application telemetry data associated with the interactive application.

In some embodiments, the application telemetry data follows an application telemetry data protocol. In some embodiments, the application telemetry data protocol comprises an account identification. In some embodiments, the application telemetry protocol includes an identification of the interactive application. In some embodiments, the application telemetry data protocol includes an action or event occurring in the interactive application. In some embodiments, the application telemetry data protocol includes application telemetry data encoded as a string. In some embodiments, the application telemetry data protocol includes application telemetry data encoded as an array of the elements making up the application telemetry data. In some embodiments, the application telemetry protocol includes application telemetry data formatted as a concatenation of data of elements making up the application telemetry data.

The process controller 1204 receives, from the interactive processing device 1202, the application telemetry data (1210). In some embodiments, the process controller 1204 is constructed to continuously monitor the interactive processing device 1202 for the application telemetry data.

The process controller 1204 scans the application telemetry data to determine whether to provide a wager actuator to the interactive processing device (1212). In some embodiments, the process controller 1204 determines whether to provide the wager actuator by parsing the application telemetry data into elements; matching each element to a table of elements that trigger providing the wager actuator; and when an element of the application telemetry data is present in the table, determine that the wager actuator should be provided. In some embodiments, a wager actuator is provided when a target is destroyed in the interactive application.

When the wager actuator providing is triggered, the process controller 1204 generates wager actuator data and commands the interactive processing device 1202 by communicating the wager actuator data to the interactive processing device 1202 (1214). In some embodiments, the wager actuator data follows a wager actuator protocol. In some embodiments, the wager actuator protocol includes an account identification. In some embodiments, the wager actuator protocol includes an identification of the interactive application. In some embodiments, the wager actuator protocol includes a wager amount. In some embodiments, the wager actuator protocol includes a paytable and/or wagering mechanic. In some embodiments, data encoded in accordance with the wager actuator protocol is formatted as a string. In some embodiments, data encoded in accordance with the wager actuator protocol is formatted as an array of the elements making up the wager actuator data. In some embodiments, data encoded in accordance with the wager actuator protocol is formatted as a concatenation of the data of elements making up the wager actuator data.

The interactive processing device 1202 receives, from the process controller 1204, the wager actuator data (1214). In some embodiments, the interactive processing device 1202 is constructed to continuously monitor for the wager actuator data.

The interactive processing device 1202, responsive to receiving the wager actuator data, configures the display to provide a wager actuator (1216). In some embodiments, the interactive processing device 1202 detects an indication to engage the provided wager actuator on the display (1218). The interactive processing device 1202 communicates, to the process controller 1204, wager actuator activation data (1220). In some embodiments, the process controller 1204 continuously monitors the interactive processing device 1202 for the wager actuator activation data.

In some embodiments, wager actuators may be accumulated and activated at the end of a session, as the wager actuators remain usable until the end of the session. Alternatively, the wager actuators may activated, resulting in the wager request, as soon as the wager actuator is generated.

The process controller 1204 receives, from the interactive processing device 1202, the wager actuator activation data (1220). The process controller 1204 scans the wager actuator activation data to determine whether to trigger a wager. In some embodiments, the process controller 1204 determines whether to trigger the wager by parsing the wager actuator activation data into elements; matching each element to a table of elements that contain valid wager actuator identifiers; and when an element of the wager actuator activation data is present in the table, determine that the wager should be triggered. In some embodiments, a wager amount is associated with the wager actuator identifier, and when the wager actuator identifier is matched in the table of elements, the wager amount is retrieved from the table of elements. In some embodiments, the wager amount is communicated in the wager actuator activation data, and each element of the wager actuator activation data is matched to a table of elements that contain wager amounts; and when an element of the wager actuator activation data is present in the table, determine a wager amount associated with the wager request.

When the wager request is triggered, the process controller 1204 generates wager request data and commands the wager server 1206 by communicating the wager request data to the wager server 1206 (1222). In some embodiments, the wager request data follows a wager request protocol. In some embodiments, the wager request protocol includes an account identification. In some embodiments, the wager request protocol includes an identification of the interactive application. In some embodiments, the wager request protocol includes a wager amount. In some embodiments, the wager request protocol includes a paytable and/or wagering mechanic. In some embodiments, data encoded in accordance with the wager request protocol is formatted as a string. In some embodiments, data encoded in accordance with the wager request protocol is formatted as an array of the elements making up the wager request data. In some embodiments, data encoded in accordance with the wager request protocol is formatted as a concatenation of the data of elements making up the wager request data.

The wager server 1206 receives, from the process controller 1204, the wager request data (1222). In some embodiments, the wager server 1206 is constructed to continuously monitor the process controller for communication of the wager request data.

The wager server 1206, in response to receiving the wager request data, automatically determines a wager outcome based on the wager request data (1224).

The wager server 1206 communicates the wager outcome data to the process controller 1204 (1226). The process controller 1204 receives, from the wager server 1206, the wager outcome data (1226).

In response to receiving the data, the process controller 1204 scans the wager outcome data and automatically determines wagering telemetry data based on the wager outcome data (1228). In response to receiving the data, the process controller 1204 scans the wager outcome data and also automatically determines application resource data based on the wager outcome data (1228). The process controller 1204 commands the interactive processing device 1202 by communicating wagering telemetry data and the application resource data to the interactive processing device 1202 (1230).

The interactive processing device 1202 receives, from the process controller 1204, the wagering telemetry data and the application resource data (1230). In response to receiving the wagering telemetry data, the interactive processing device 1202 automatically configures a wagering user interface using the wagering telemetry data as described herein (1232). In some embodiments, the wagering user interface is a part of the display provided by the interactive processing device 1202. The interactive processing device 1202 also automatically incorporates the application resource data into the interactive application as described herein, thus affecting the interactive application (1232). In some embodiments, the interactive processing device 1202 receives, from the process controller 1204, an application resource display signal associated with the application resource awarded based on the application telemetry. In some embodiments, the interactive processing device 1202 displays the application resource based on the application resource signal. In some embodiments, the interactive processing device 1202 automatically configures the interactive application display based on the application resource signal.

In some embodiments, the process controller 1204 and the wager server 1206 are in a regulated environment, and the interactive processing device 1202 is in an unregulated environment. In some embodiments, the wager server 1206 is in the regulated environment and the process controller 1204 and the interactive processing device 1202 are in the unregulated environment. In some embodiments the regulated environment is a regulated gambling environment.

The distribution of the responsibilities between the interactive processing device 1202, the process controller 1204, and the wager server 1206 allow the components of the system to provide lower latency interactions. In some embodiments, the processing requirements of the interactive application do not allow the interactive processing device 1202 to perform the responsibilities of the process controller 1204 and/or the wager server 1206. In addition, because the interactive processing device 1202 is outside of the regulated environment, the interactive processing device 1202 may not have access to wager outcome determinations. That is, the wager server 1206 is responsible for determining the wager outcome.

Figure 11:
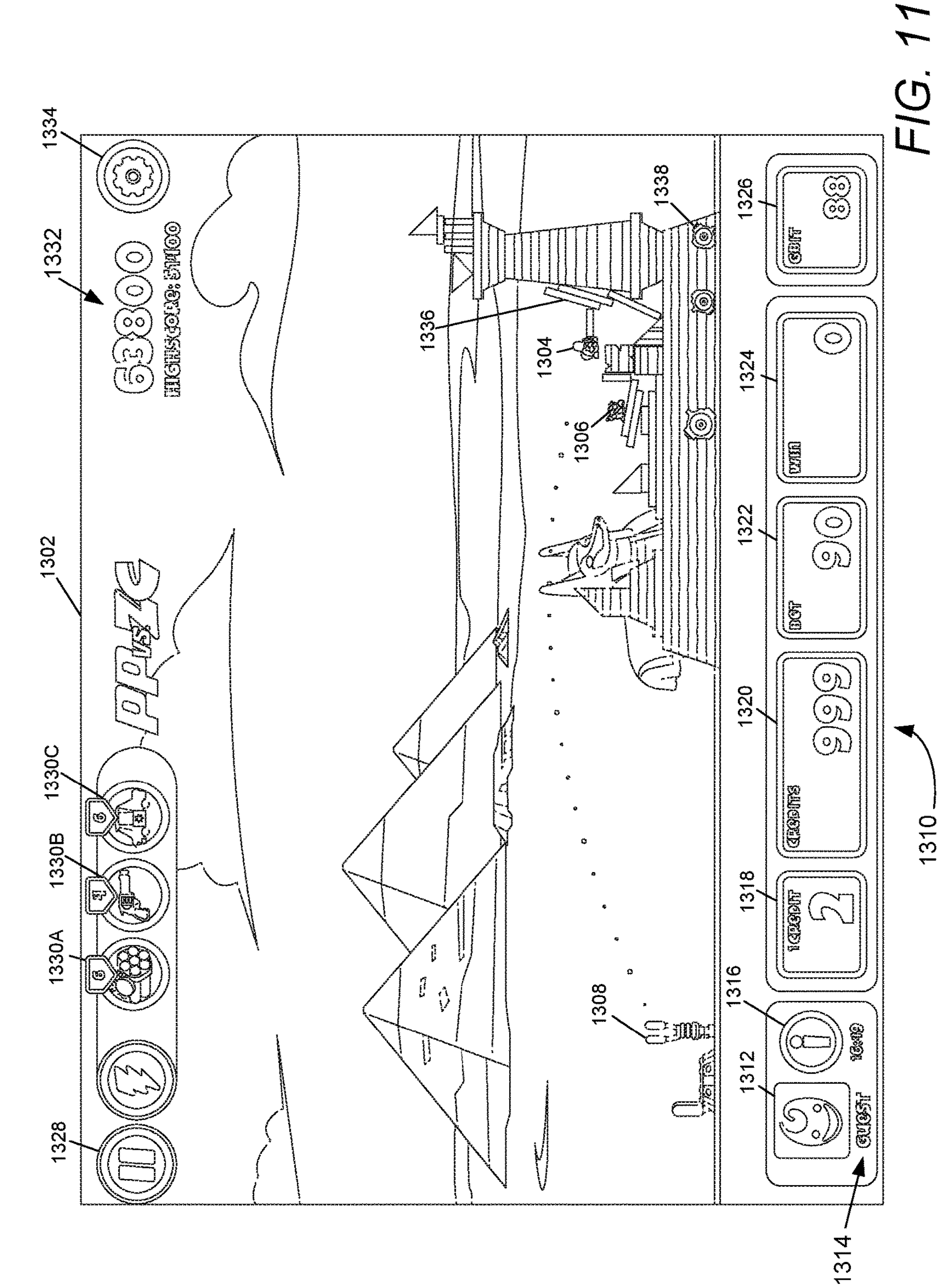
FIG. 11 illustrates an instance of an interactive application provided by an interactive processing device, implemented using one or more processing devices, in accordance with some embodiments of the invention.

FIG. 11 illustrates an instance of an interactive application provided by an interactive processing device, implemented using one or more processing devices, in accordance with some embodiments of the invention. The interactive processing device provides a display 1302 of an interactive application. As illustrated, a user begins a session of the interactive application with an assortment of ballistic objects 1304 (in this embodiment, represented by a dog), with which the user attempts to eliminate one or more targets 1306 (in this embodiment, represented by a cat), and the targets' accompanying thematically appropriate environment. The user selects the ballistic object 1304, placed in an interactable launching element 1308, and pulls back on the ballistic object 1304, thereby assigning both an initial magnitude for the ballistic object's velocity and an initial launch vector with which the interactive processing device calculates a parabolic path for the ballistic object 1304 to take when the ballistic object 1304 is launched. The user does this with the goal of eliminating the targets 1306 and their environment arrayed on the right side of the display 1302.

At the bottom of the display 1302, a credit bar 1310 is displayed, including: a logo 1312, information identifying the user 1314, a selectable option to display information regarding the interactive application 1316, a current denomination selection presented as a value of a credit 1318, a total number of credits the user possesses 1320, a recent wager amount 1322, a recent win amount 1324, and a number of application credits that the user has accumulated 1326. At the top of the display 1302, the user is presented with the interactive application's menus and information bars, displaying: a selectable icon by which the user may access the pause menu 1328; an in-application item bar illustrating an array of various gameplay altering items 1330A-1330C (in this embodiment represented by a stick of dynamite, a revolver, and a police car); the interactive application's title and logo; the current user's in-application score 1332; and a selectable icon through which the user may access a settings menu 1334.

The user's ballistic object inventory is displayed on the left side of the display 1320. Next to the inventory is the launching element 1308 (in this embodiment, represented by a stylized slingshot), from which the user interacts with the ballistic objects 1304, assigning their velocity magnitude and initial direction vector. To the right of the objects are the targets 1306 and their destroyable environment. The targets 1306 vary in attributes and point value; these discrete targets 1306 are intuitively distinguishable by their variation in design and size. The destroyable environment is constructed using various geometric shapes, which are thematically stylized to be complementary to the interactive application's level design and assembled in various structures to support, shelter, or otherwise contribute to the targets' positioning. Behind the main stage of play is a background, thematically setting the tone for the interactive application's stage of play.

In the example embodiment, there exist different ballistic objects 1304 with different abilities and attributes to be launched at the targets 1306. The variation ranges from different sizes and weights to different latent abilities able to be performed while the ballistic object 1304 is traveling. The inclusion of an array of various ballistic objects 1304 for the user to use adds to the strategic component of the resource management aspect of the interactive application, and contributes to varied gameplay possibilities.

In the example embodiment, the user interacts with the interactive application with the goal of destroying targets 1306 and their environment. The various destroyable elements 1336 in the interactive application have varying attributes related to the energy value with which they must be hit to be destroyed and the accompanying actions that happen when they are destroyed. The different elements 1336 (in this embodiment, represented by blocks of wood, blocks of cement, and panes of glass), not only require different magnitudes of force to be destroyed, but possess different values of mass and inertia. The targets 1306 require a minimum magnitude of force to be destroyed as well. The different targets 1306, represented to the user visually via different design aesthetics and size, possess different magnitudes of force thresholds needed to be destroyed. This information is conveyed to the user intuitively by having the larger of the targets require more force to be destroyed. Having the destructions triggered by a force magnitude allows for the targets 1306 to be destroyed via various methods, ranging from causing the target to fall to the ground, directly striking the target 1306 with a ballistic object 1304, and eliminating the target 1306 via an impact with an environment element 1336. The combination of different values needed to destroy targets with different resistance to breaking and inertia attributes of the environment elements allows for varying and interesting application options for the user to accomplish the goal of the interactive application; the interactive application presents the option to the user to indirectly eliminate targets through the creative and varied use of environment elements 1336 and the efficient management of their ballistic object resources 1304. However, due to the inherently different attributes of the different elements, the interactive application presents many possible results for an element's colliding with a target 1306. In some embodiments, a wood element falling on a target may not destroy it, but an equivalently sized cement element may; however, a wood element may be able to move farther than the cement element, allowing for more range of possible contact. The possible combinations and gameplay results in a possible embodiment of the interactive application are enough to present many opportunities of discovery and creativity for the user.

When the user succeeds in destroying a target 1306, an actuator 1338 for the wagering event (in this embodiment, represented by a chronometer), is spawned. The size of the wager is determined by the type of target destroyed, that is the larger and more difficultly destroyed targets award the user with the opportunity of wagering two or three credits while the smaller, common, and easily destroyed targets only award the user with the opportunity of wagering one credit. The actuators 1338 can be activated at any point during interaction with the interactive application by the user's selecting them. In this fashion, the user can also choose a denomination by only activating the denomination that the user wants.

Upon activating an actuator 1338, the user is presented with a confirmation screen, relating the size of the wager and presenting the option for the user to back out from the wager in the event that the user reconsiders or possibly activated the actuator 1338 by accident.

The user is given the option to activate the wager sequence actuator at any time during gameplay. The wager sequence, by virtue of granting in-application, session-altering rewards, becomes a dynamic and integral mechanic for the user's strategy. The user may simply accumulate the actuators and activate them all at the end of the stage, as the actuators remain usable until the user continues to the next stage. However, the user may activate an actuator, engaging in the wager event, as soon as the actuator is spawned by eliminating a target. In some embodiments, the interactive application is a game of resource management, and as such the user is tasked with the problem of using the user's resources (e.g., ballistic objects and items that can be earned via wagering events), in the most efficient way possible to successfully eliminate all of a stage's targets. In an example embodiment, the user may encounter a situation where the supply of ballistic objects is diminishing, yet a substantial number of targets remain to be eliminated. The user then faces the decision to either engage in an earned wager event, with the high probability of being awarded an in-application reward, in the hopes of gaining an item to facilitate completion of the level or opt to continue on without wagering, a wager in itself where the user risks losing progress and score in that level. This intertwining of risk management, resource management, skill, and chance-based wager propositions in a single and cohesive application creates a unique experience previously unoffered for the user. Similarly, it is entirely at the discretion of the user whether or not the user gambles. If the user is truly skilled, the user may be able to proceed without ever having to gamble. Thus, not only is the opportunity to gamble earned, but the opportunity can be denied by the user as well.

Gameplay continues in this fashion, with the user launching ballistic objects at the targets with the goal of destroying them, until all of the targets are destroyed or the user has exhausted the resource pool of ballistic objects. Upon successful elimination of all targets, the user is presented with the option of either continuing to the interactive processing device's next level or to activate the user's remaining wager actuators. If the user continues without activating the user's remaining wager actuators, those wager actuators and their accompanying wager event opportunities are forfeited and do not carry over to the next round of interaction with the interactive application. If the user has failed to eliminate all targets before exhausting the user's ballistic objects, the user may either terminate interaction with the interactive application or retry the level and is not allowed to continue onwards until the requirements of the level are satisfied. Continuation or resetting, depending on the success of the level, is achieved via the user's selection of a corresponding icon on the display.

Upon finishing a level, the user receives a rating based on the relationship of the user's score and the maximum score possible for that level. Throughout gameplay, the user is awarded points for the elimination of targets, the destruction of environment elements, and any ballistic objects that remain after all targets have been eliminated. There exists a maximum score for each level, calculated at the level's initiation. The closer the user's score is to the maximum possible score, the more the user is rewarded. In some embodiments, the user's rating and reward are presented as a number of stars out of a possible three, three corresponding to the highest score threshold that the interactive processing device will reward for. Each star earned by the user rewards the user with application credit redeemable for the chance of winning real currency credits or real item rewards outside of the interactive application. The number of application credits a user possesses is reflected in the bottom right corner of the application display. The user is also presented with three menu options: the reset option, the level select option, and the continue to the next level option.

Figure 12:
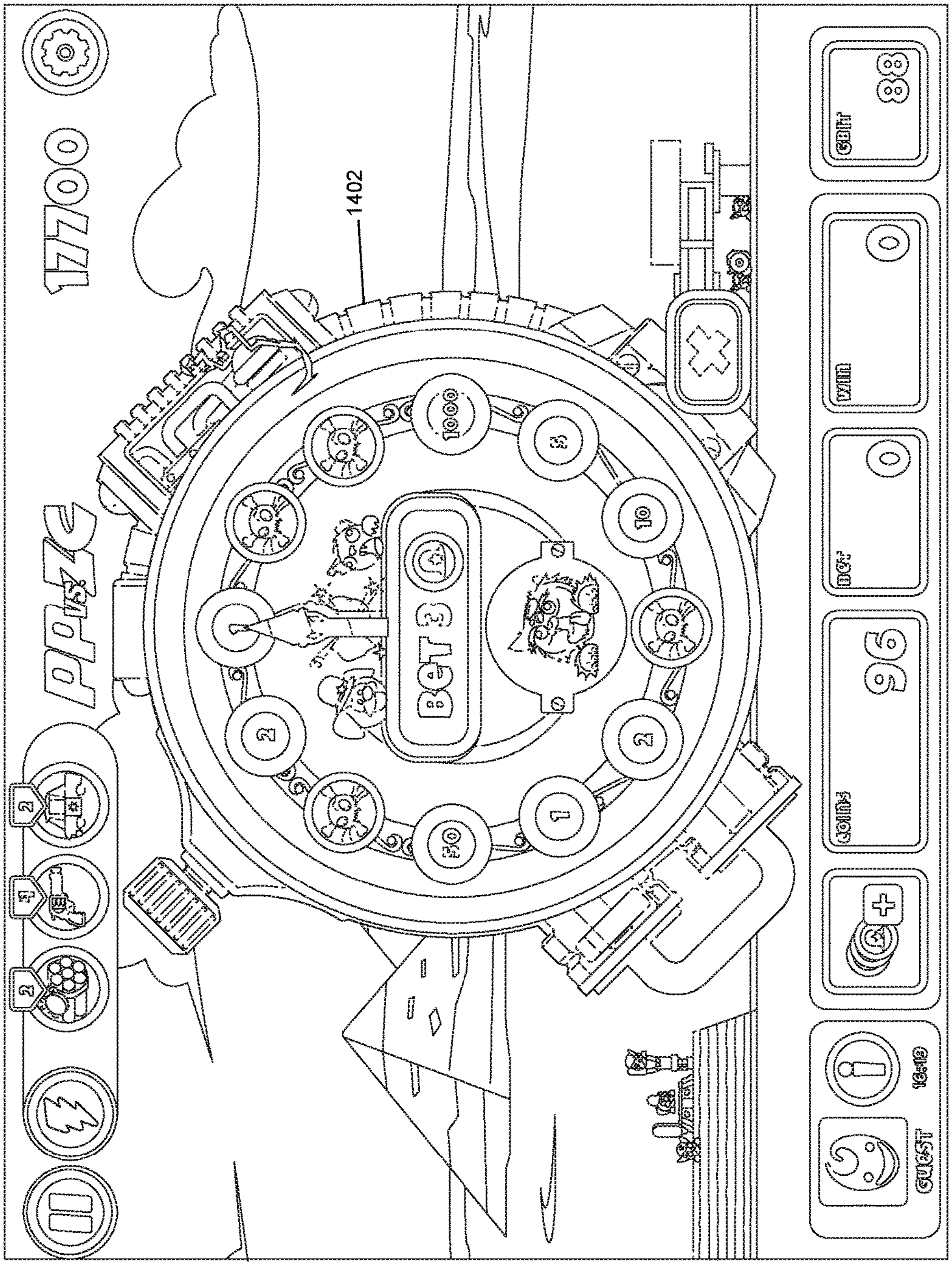
FIG. 12 illustrates an instance of an interactive application provided by an interactive processing device, implemented using one or more processing devices, in accordance with some embodiments of the invention.

FIG. 12 illustrates an instance of an interactive application provided by an interactive processing device, implemented using one or more processing devices, in accordance with some embodiments of the invention. Upon acceptance of a wager by the user, the wager server determines a wager outcome and the user's credit return. Simultaneously, a separate random number generation is executed by the process controller to calculate the user's in-application reward. In this embodiment, the user's in-application reward takes the form of items to facilitate the interaction with the interactive application. In an example embodiment, if the user does not win an in-application reward, there is a 5% chance that the user wins a bonus spin and earns another chance at winning an in-application reward. The process controller then presents a wager process display and the result of the wager to the user. In some embodiments, the display of the wager outcome is embodied by a dual-wheel spinning wheel display. In some embodiments, the spinning wheel is presented in the style of a chronometer 1402 with a large spinning hand used to relate a real currency credit or virtual credit return and an inner spinning wheel that displays the in-application reward through a window similar to a date window of a chronometer. The interactive processing device configures the display based on the real currency or virtual currency credit reward and the in-application reward to the user before the user is presented with the core interactive application interface.

Figure 13:
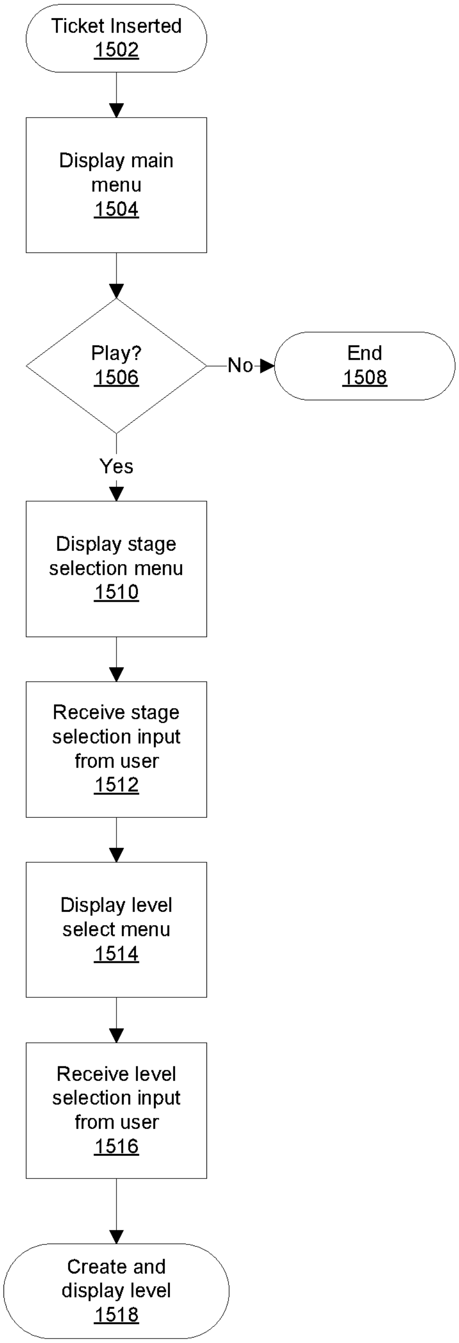
FIG. 13 illustrates a process of a delayed wager interleaved wagering system in accordance with various embodiments of the invention.

FIG. 13 illustrates a process of a delayed wager interleaved wagering system in accordance with various embodiments of the invention. Upon insertion of a ticket (1502), the main menu is displayed (1504). In some embodiments, a ticket insertion is detected by the wager server and ticket insertion detection data is communicated from the wager server to the interactive processing device. In some embodiments, the interactive processing device displays the main menu of the interactive application upon receiving the ticket insertion detection data. The user may choose to either play or not (1506). When an indication to not play is received, the process ends (1508). Upon confirmation of desire to play, the stage selection menu is displayed (1510). In some embodiments, the interactive processing device detects the indication to proceed and automatically configures the display to provide the stage selection menu. After receiving the stage selection input (1512), the level select menu is presented (1514). In some embodiments, the interactive processing device detects the stage selection input and automatically configures the display to provide the level select menu. Upon receiving the level selection input (1516), the level is created and displayed (1518). In some embodiments, the interactive processing device detects the level selection input and automatically configures the display to provide the level created by the interactive processing device.

Figure 14:
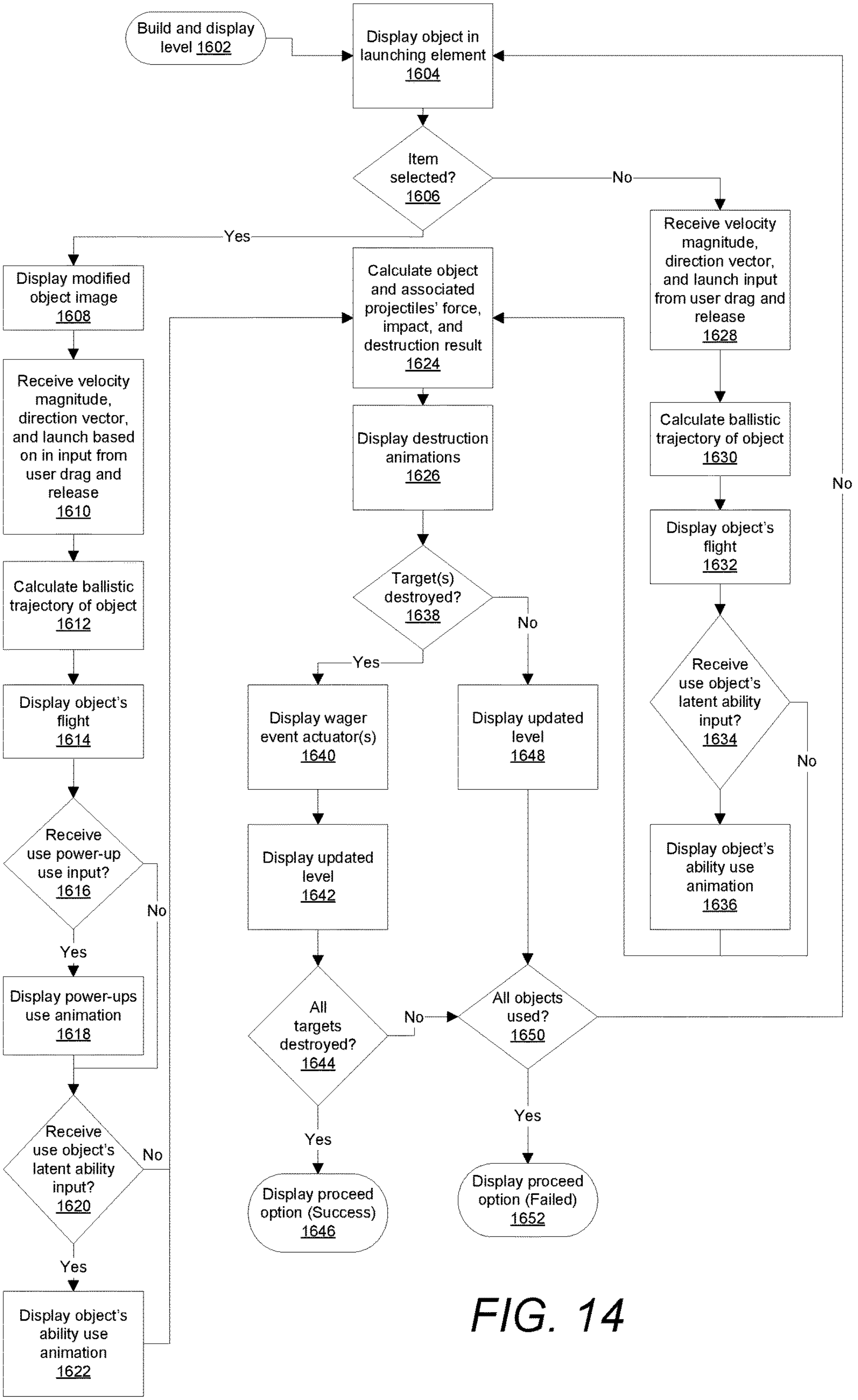
FIG. 14 illustrates a process of a delayed wager interleaved wagering system in accordance with various embodiments of the invention.

FIG. 14 illustrates a process of a delayed wager interleaved wagering system in accordance with various embodiments of the invention. After building and displaying a level of an interactive application provided by an interactive processing device (1602), the ballistic object to be launched is displayed in the launching element (1604). In some embodiments, the interactive processing device configures a display to provide the level and configures the display to provide the ballistic object in the launching element.

It is determined if an in-application item is selected (1606). In some embodiments, the interactive processing device detects whether an item is selected. If an in-application item is selected for use, the ballistic object image is then changed to a modified ballistic object image to reflect that the in-application item has been used (1608). In some embodiments, the interactive processing device configures the display to provide the modified ballistic object image.

The velocity magnitude, direction vector, and launch begin input are all automatically determined based on the user's input (1610). In some embodiments, the velocity magnitude, direction vector, and launch begin inputs are determined by the interactive processing device based on a user input of a drag and release input on a device capable of detecting touch from the user. The ballistic trajectory of the ballistic object is automatically calculated using these values (1612). In some embodiments, the interactive processing device automatically determines the values.

Once the path is calculated, the ballistic object's flight and accompanying animations are displayed by the interactive processing device (1614). It is determined by the interactive processing device if an item input is received (1616). If an in-application item was initially selected for use and the use in-application item input is received, the in-application item's use animation is displayed (1618). It is determined by the interactive processing device if an indication to use the ballistic object's latent ability is received (1620). If input is received to use the ballistic object's latent ability, if it possesses one, the ballistic object's ability use animation is displayed (1622).

The ballistic object and its associated projectiles' force, impact, and destruction result is calculated by the interactive processing device and the corresponding destruction animations and results are displayed by the interactive processing device (1624). If a target is successfully destroyed, wager event actuators corresponding to the value of the target destroyed are displayed along with the updated level (1626).

The interactive processing device determines if one or more targets are destroyed (1638). If one or more targets are destroyed, wager event actuators are displayed (1640). In some embodiments, the interactive processing device configures the display to provide the one or more wager actuators. An updated level display is provided by the interactive processing device (1642). The interactive processing device determines if all targets are destroyed (1644). If all targets were destroyed, a dialogue corresponding to the successful completion of a level is displayed (1646).

If no targets were destroyed, the updated level is displayed by the interactive processing device (1648). If targets remain, whether or not all ballistic objects have been exhausted is determined (1650). If no ballistic objects remain, a dialogue corresponding to a failed level is displayed (1652). However, if ballistic objects remain, the next ballistic object is displayed in the launching element and the session continues in this fashion until either all ballistic objects are exhausted or all targets are destroyed.

If the interactive processing device determines (1606) that no items are selected, the velocity magnitude, direction vector, and launch begin input are all automatically determined based on the user's input (1628). In some embodiments, the velocity magnitude, direction vector, and launch begin inputs are determined by the interactive processing device based on a user input of a drag and release input on a device capable of detecting touch from the user. The ballistic trajectory of the ballistic object is automatically calculated using these values (1630). In some embodiments, the interactive processing device automatically determines the values.

Once the path is calculated, the ballistic object's flight and accompanying animations are displayed by the interactive processing device (1632). It is determined by the interactive processing device if an indication to use the ballistic object's latent ability is received (1634). If input is received to use the ballistic object's latent ability, if it possesses one, the ballistic object's ability use animation is displayed (1636).

Figure 15:
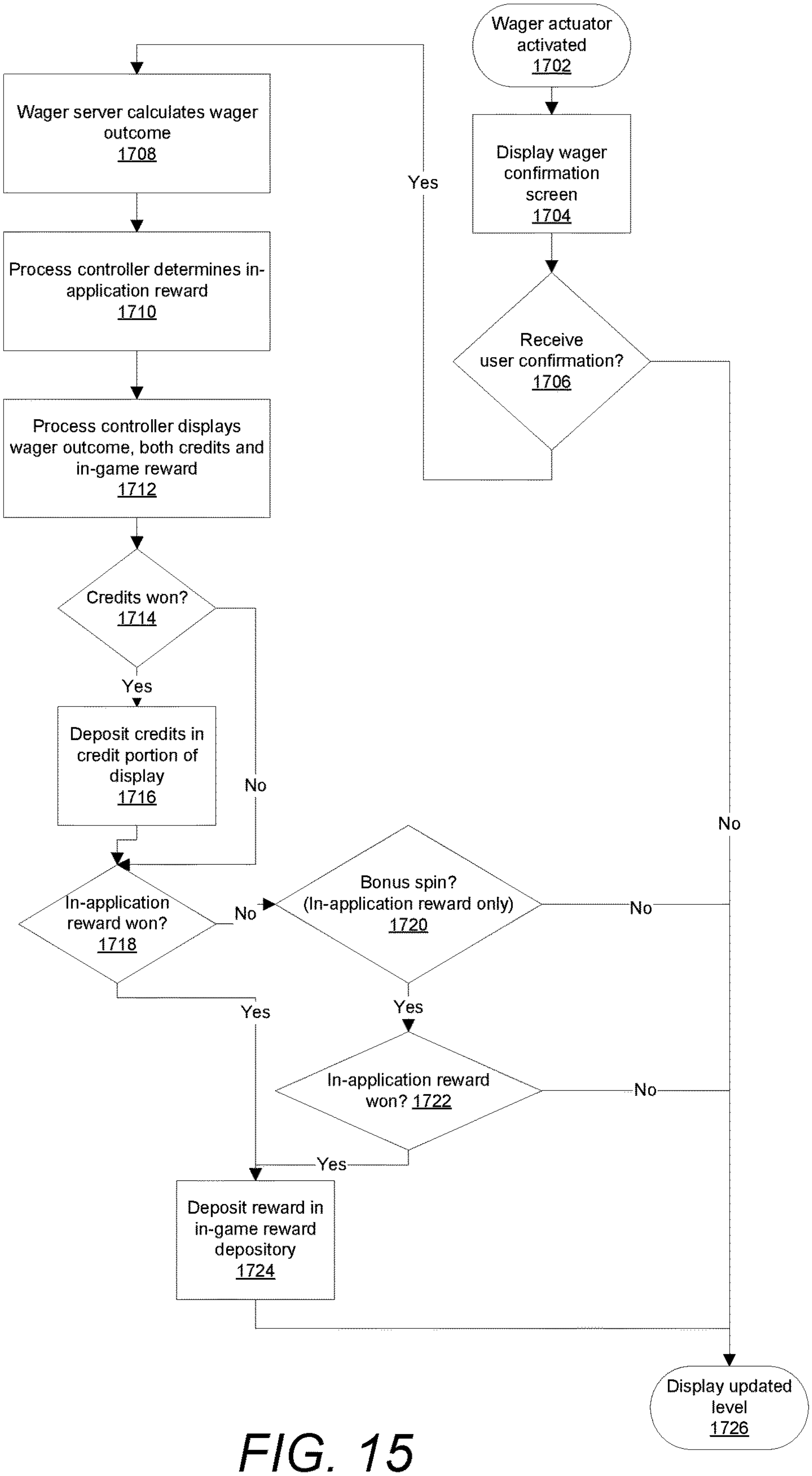
FIG. 15 illustrates a process of a delayed wager interleaved wagering system in accordance with various embodiments of the invention.

FIG. 15 illustrates a process of a delayed wager interleaved wagering system in accordance with various embodiments of the invention. Upon the receiving of the wager actuator input (1702), a wager confirmation screen is displayed (1704). In some embodiments, the interactive processing device receives an indication of activation of a wager actuator and automatically configures a display to provide the wager confirmation. If an input of no is received, the user effectively backs out of the wager and the interactive processing device displays an updated level (1726). If an input of yes is received, the wager server determines a wager outcome and communicates the wager outcome data to the interactive processing device via the process controller (1708).

The process controller determine the user's in-application reward (1710). In some embodiments, the process controller uses an RNG to determine the in-application reward. Once the wagers are calculated, the process controller displays the wager outcome, both credits and in-application reward (1712). In some embodiments, the process controller communicates the wager outcome and in-application reward data to the interactive processing device, and the interactive processing device automatically configures the display to provide the wager outcome and in-application reward data.

The interactive processing device determines if credits are awarded (1714). If credits are won, the display is configured based on the wager outcome. The interactive processing device determines if in-application rewards are awarded (1718). If an in-application reward is awarded, the display is configured based on the in-application reward (1724). If an in-application reward is not initially won, there is a chance that the user is awarded a bonus spin for the in-application item reward wager (1720). If the bonus spin is awarded, the user process controller re-runs its process (in some embodiments using an RNG) to give the user another opportunity to win an in-application reward (1722). If the user is successful the second time, the in-application reward is deposited in its depository (1724). The updated level is then displayed, reflecting one fewer wager event actuator (1726).

Figure 16:
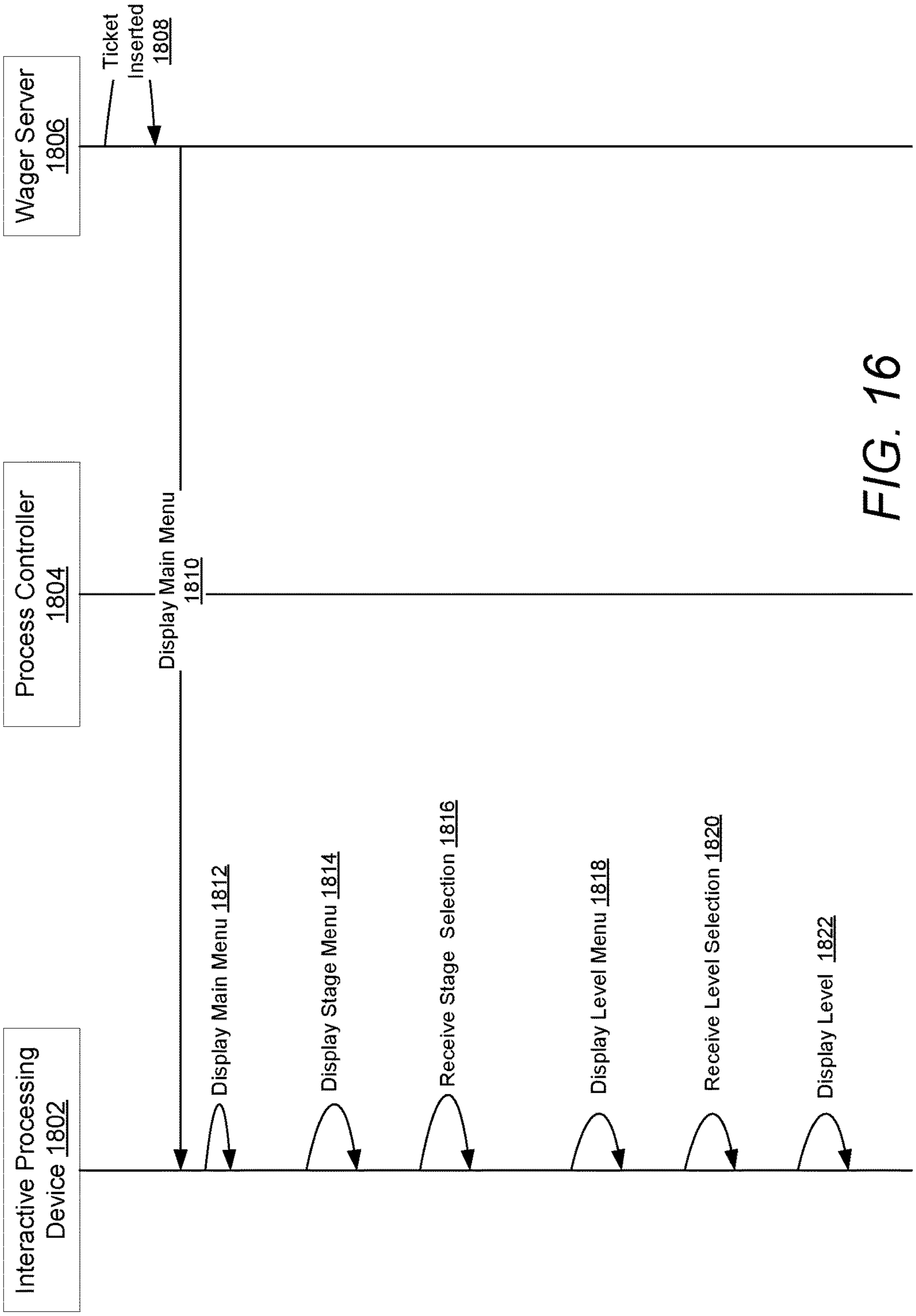
FIG. 16 is a sequence diagram of interactions between components of a delayed wager interleaved wagering system in accordance with various embodiments of the invention.

FIG. 16 is a sequence diagram of interactions between components of a delayed wager interleaved wagering system in accordance with various embodiments of the invention. In some embodiments, the delayed wager interleaved wagering system includes an interactive processing device 1802, a process controller 1804, and a wager server 1806. When the wager server 1806 detects that a ticket has been inserted (1808), it communicates main menu display command data to the interactive processing device 1802, prompting the interactive processing device to automatically display a main menu (1812). The interactive processing device 1802 detects a play confirmation indication, and after detecting the play confirmation indication, the interactive processing device automatically configures the display to provide the stage menu (1814). Following the receiving of the stage selection (1816), the interactive processing device displays the level menu (1818). After receiving the level selection (1820), the interactive processing device displays the level (1822).

While the above description may include many specific embodiments of the invention, these should not be construed as limitations on the scope of the invention, but rather as examples of embodiments thereof. It is therefore to be understood that the present invention can be practiced otherwise than specifically described, without departing from the scope and spirit of the present invention. Thus, embodiments of the present invention described herein should be considered in all respects as illustrative and not restrictive.

What is claimed:

1. A delayed wager interleaved wagering system, comprising:

an interactive processing device constructed to:

provide an interactive application display associated with an interactive application provided by the interactive processing device;

request, from the process controller, wager actuator data;

responsive to receiving the wager actuator data, automatically configure the display to provide a wager actuator;

communicate, to the process controller, wager actuator activation data based on detection of an indication to activate the wager actuator;

receive, from the process controller, wagering telemetry data and application resource data;

responsive to receiving the wagering telemetry data, automatically configure the display based on the wagering telemetry data; and automatically incorporate the application resource data into the interactive application;

a wager server constructed to:

continuously monitor the process controller for wager request data;

responsive to receiving the wager request data, automatically determine a wager outcome based on the wager request data; and communicate, to the process controller, wager outcome data; and the process controller operatively connecting the interactive processing device and the wager server, the process controller constructed to:

receive, from the interactive processing device, the wager actuator activation data;

generate the wager actuator data;

scan the wager actuator activation data to determine whether to trigger a wager request;

when the wager request is triggered, generate wager request data;

receive, from the wager server, the wager outcome data;

responsive to receiving the data, scan the wager outcome data;

automatically determine the wagering telemetry data and the application resource data based on the wager outcome data; and communicate, to the interactive processing device, the wagering telemetry data and the application resource data.

2. The delayed wager interleaved wagering system of claim 1, wherein the interactive processing device and the process controller are constructed from the same device, and wherein the process controller is operatively connected to the wager server using a communication link.

3. The delayed wager interleaved wagering system of claim 1, wherein the wager server and the process controller are constructed from the same device, and wherein the process controller is operatively connected to the interactive processing device using a communication link.

4. The delayed wager interleaved wagering system of claim 1, wherein the interactive processing device is further constructed to detect an indication to activate the wager actuator.

5. The delayed wager interleaved wagering system of claim 1, wherein the wager actuator is displayed with one or more other previously generated wager actuators.

6. The delayed wager interleaved wagering system of claim 1, wherein the wager actuator data comprises a wager amount, and a size of the wager actuator displayed is based on the wager amount.

7. The delayed wager interleaved wagering system of claim 1, wherein the process controller continuously monitors for application telemetry data.

8. The delayed wager interleaved wagering system of claim 1, further comprising:

a credit processing controller; and an enclosure constructed to mount:

a user input device operatively connected to the interactive controller;

a user output device operatively connected to the interactive controller;

a credit input device operatively connected to the credit processing controller; and a credit output device operatively connected to the credit processing controller.

9. A delayed wager interleaved wagering system, comprising:

a wager server of the delayed wager interleaved wagering system, the wager server constructed to:

continuously monitor the process controller for wager request data;

responsive to receiving the wager request data, automatically determine a wager outcome based on the wager request data; and communicate, to the process controller, wager outcome data; and the process controller of the delayed wager interleaved wagering system operatively connecting the wager server to an interactive processing device using a communication link, the process controller constructed to:

receive, from the interactive processing device, wager actuator activation data;

generate wager actuator data;

scan the wager actuator activation data to determine whether to trigger a wager request;

when the wager request is triggered, generate wager request data;

receive, from the wager server, the wager outcome data;

responsive to receiving the data, scan the wager outcome data;

automatically determine the wagering telemetry data and the application resource data based on the wager outcome data; and communicate, to the interactive processing device, the wagering telemetry data and the application resource data.

10. The delayed wager interleaved wagering system of claim 9, wherein the interactive processing device is further constructed to detect an indication to activate the wager actuator.

11. The delayed wager interleaved wagering system of claim 9, wherein the wager actuator is displayed with one or more other previously generated wager actuators.

12. The delayed wager interleaved wagering system of claim 9, wherein the wager actuator data comprises a wager amount, and a size of the wager actuator displayed is based on the wager amount.

13. The delayed wager interleaved wagering system of claim 9, wherein the process controller continuously monitors for application telemetry data.

14. The delayed wager interleaved wagering system of claim 9, further comprising:

a credit processing controller; and an enclosure constructed to mount:

a user input device operatively connected to the interactive controller;

a user output device operatively connected to the interactive controller;

a credit input device operatively connected to the credit processing controller; and a credit output device operatively connected to the credit processing controller.

15. A delayed wager interleaved wagering system, comprising:

an interactive processing device of the delayed wager interleaved wagering system, the interactive processing device constructed to:

provide an interactive application display associated with an interactive application provided by the interactive processing device;

request, from the process controller, wager actuator data;

responsive to receiving the wager actuator data, automatically configure the display to provide a wager actuator;

communicate, to the process controller, wager actuator activation data based on detection of an indication to activate the wager actuator;

receive, from the process controller, wagering telemetry data and application resource data;

responsive to receiving the wagering telemetry data, automatically configure the display using the wagering telemetry data; and automatically incorporate the application resource data into the interactive application; and the process controller of the delayed wager interleaved wagering system operatively connecting the interactive processing device to a wager server, the process controller constructed to:

receive, from the interactive processing device, the request for the wager actuator data;

generate the wager actuator data;

communicate, to the interactive processing device, the wager actuator data;

receive, from the interactive processing device, the wager actuator activation data;

scan the wager actuator activation data to determine whether to trigger a wager request;

when the wager request is triggered, generate wager request data;

receive, from the wager server, the wager outcome data;

responsive to receiving the data, scan the wager outcome data;

automatically determine the wagering telemetry data and the application resource data based on the wager outcome data; and communicate, to the interactive processing device, the wagering telemetry data and the application resource data.

16. The delayed wager interleaved wagering system of claim 15, wherein the interactive processing device is further constructed to detect an indication to activate the wager actuator.

17. The delayed wager interleaved wagering system of claim 15, wherein the wager actuator is displayed with one or more other previously generated wager actuators.

18. The delayed wager interleaved wagering system of claim 15, wherein the wager actuator data comprises a wager amount, and a size of the wager actuator displayed is based on the wager amount.

19. The delayed wager interleaved wagering system of claim 15, wherein the process controller continuously monitors for application telemetry data.

20. The delayed wager interleaved wagering system of claim 15, further comprising:

a credit processing controller; and an enclosure constructed to mount:

a user input device operatively connected to the interactive controller;

a user output device operatively connected to the interactive controller;

a credit input device operatively connected to the credit processing controller; and a credit output device operatively connected to the credit processing controller.

* * * * *